US011987799B2

(12) United States Patent
Vriezen et al.

(10) Patent No.: US 11,987,799 B2
(45) Date of Patent: May 21, 2024

(54) **DOWNY MILDEW RESISTANCE IN *CUCURBITACEAE* PLANTS**

(71) Applicant: Nunhems B.V., Nunhem (NL)

(72) Inventors: Wim Vriezen, Nunhem (NL); Frank Beenders, Nunhem (NL); Lieke Mertens, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 86 days.

(21) Appl. No.: 17/613,401

(22) PCT Filed: May 18, 2020

(86) PCT No.: PCT/EP2020/063809
§ 371 (c)(1),
(2) Date: Nov. 22, 2021

(87) PCT Pub. No.: WO2020/239496
PCT Pub. Date: Dec. 3, 2020

(65) Prior Publication Data

US 2022/0275393 A1 Sep. 1, 2022

(30) Foreign Application Priority Data

May 24, 2019 (EP) .................................... 19176547

(51) Int. Cl.
*C12N 15/82* (2006.01)

(52) U.S. Cl.
CPC ............................... *C12N 15/8282* (2013.01)

(58) Field of Classification Search
None
See application file for complete search history.

(56) References Cited

FOREIGN PATENT DOCUMENTS

| | | |
|---|---|---|
| WO | 2009/012314 A1 | 1/2009 |
| WO | 2011/050296 A1 | 4/2011 |
| WO | 2012/069539 A1 | 5/2012 |

OTHER PUBLICATIONS

Somkuwar et al. Cucurbit Genetics Cooperative Report (1993)16:40-41.*

Cheng Hong et al. Horticultural Plant Journal (2015), 1(3):165-171.*

"Development of potyvirus resistance in melon using CRISPR/Cas9 technology", Research Project, Seed Improvement and Propagation Station, COA Executive Yuan, 2020, 4 pages.

"Implementation of CRISPR/Cas9 technology in melon to edit fruit ripening and CMV resistant genes", Grant agreement ID: 793090, MeloCRISP, Cordis—European Union, last updated on Jul. 27, 2021, 4 pages. URL: https://cordis.europa.eu/project/id/793090/reporting.

Berg, et al., "A transposable element insertion in the susceptibility gene CsaMLO8 results in hypocotyl resistance to powdery mildew in cucumber", BMC Plant Biology, vol. 15, Issue 1, Article No. 243, Oct. 9, 2015, pp. 1-17.

Burger, et al., "Development of sweet melon (*Cucumis melo*) genotypes combining high sucrose and organic acid content", Journal of the American Society for Horticultural Science, vol. 128, Issue 4, Jul. 2003, pp. 537-540.

C. E. Thomas, "Additional Evaluations of *Cucumis melo* L. Germplasm for Resistance to Downy Mildew", Hortscience, vol. 34, Issue 5, Aug. 1999, pp. 920-921.

Cao, et al., "The Power of CRISPR-Cas9-Induced Genome Editing to Speed Up Plant Breeding", International Journal of Genomics , vol. 2016, Article No. 5078796, Dec. 20, 2016, pp. 1-10.

Dhillon, et al., "Diversity among landraces of Indian snapmelon (*Cucumis melo* var. momordica)", Genetic Resources and Crop Evolution, vol. 54, Issue 6, Sep. 2007, pp. 1267-1283.

European Search Report for EP Patent Application No. 19176547.8, dated Jul. 24, 2019, 3 pages.

Guner, et al., "The genes of watermelon", HortScience, vol. 39, Issue 6, Oct. 2004, pp. 1175-1182.

Henikoff, et al., "Amino acid substitution matrices from protein blocks", Proceedings of the National Academy of Sciences of the United States of America, vol. 89, Issue 22, Nov. 15, 1992, pp. 10915-10919.

International Search Report for PCT Patent Application No. PCT/EP2020/063809, dated Jul. 20, 2020, 4 pages.

Lebeda, et al., "Response of Cucumis melo accessions to isolates of Pseudoperonospora cubensis with different levels of virulence", Scientia Horticulturae, vol. 200, Issue 8, Mar. 8, 2016, pp. 45-54.

Li, et al., "QTL Analysis for Downy Mildew Resistance in Cucumber Inbred Line PI 197088", Plant Disease, vol. 102, Issue 7, Apr. 27, 2018, pp. 1240-1245.

McCallum, et al., "Targeting Induced LocalLesions IN Genomes (Tilling) for plant functional genomics", Plant Physiology, vol. 123, Issue 2, Jun. 2000, pp. 439-442.

Michael J. Thomson, "High-Throughput SNP Genotyping to Accelerate Crop Improvement", Plant Breeding and Biotechnology, vol. 2, Issue 3, Sep. 30, 2014, pp. 195-212.

Perchepied, et al., "Relationship Between Loci Conferring Downy Mildew and Powdery Mildew Resistance in Melon Assessed by Quantitative Trait Loci Mapping", Phytopathology, vol. 95, Issue 5, May 2005, pp. 556-565.

Rodriguez-Leal, et al., "Engineering Quantitative Trait Variation for Crop Improvement by Genome Editing", Cell, vol. 171, Issue 2, Oct. 5, 2017, pp. 470-480.

Taler, et al., "Plant eR Genes That Encode Photorespiratory Enzymes Confer Resistance against Disease", Plant Cell, vol. 16, Issue 1, Jan. 1, 2004, pp. 172-184.

Thomas, et al., "Evaluation of Melon Germplasm for Resistance to Downy Mildew", Hortscience, vol. 27, Issue 5, 1992, pp. 434-436.

(Continued)

*Primary Examiner* — Medina A Ibrahim
(74) *Attorney, Agent, or Firm* — ArentFox Schiff LLP

(57) ABSTRACT

The present invention is directed to Cucurbitaceae plants comprising reduced susceptibility to downy mildew due to the modification of a susceptibility gene of the plant.

21 Claims, 4 Drawing Sheets

Specification includes a Sequence Listing.

(56) References Cited

OTHER PUBLICATIONS

Tian, et al., "Efficient CRISPR/Cas9-based gene knockout in watermelon", Plant Cell Reports, vol. 36, Issue 3, Dec. 19, 2016, pp. 399-406.

Tian, et al., "Engineering herbicide-resistant watermelon variety through CRISPR/Cas9-mediated base-editing", Plant Cell Reports, vol. 37, Issue 9, May 24, 2018, pp. 1353-1356.

Wang, et al., "QTL mapping of downy and powdery mildew resistances in PI 197088 cucumber with genotyping-by-sequencing in RIL population", Theoretical and Applied Genetics, vol. 131, Nov. 20, 2017, pp. 597-611.

Yoshioka, et al., "Identification of quantitative trait loci for downy mildew resistance in cucumber (*Cucumis sativus* L.)", Euphytica, vol. 198, Issue 2, 2014, pp. 265-276.

Zhang, et al., "Tissue Culture-Induced Heritable Genomic Variation in Rice, and Their Phenotypic Implications", PLoS One, vol. 9, Issue 5, May 7, 2014, pp. 1-10.

* cited by examiner

Figure 1

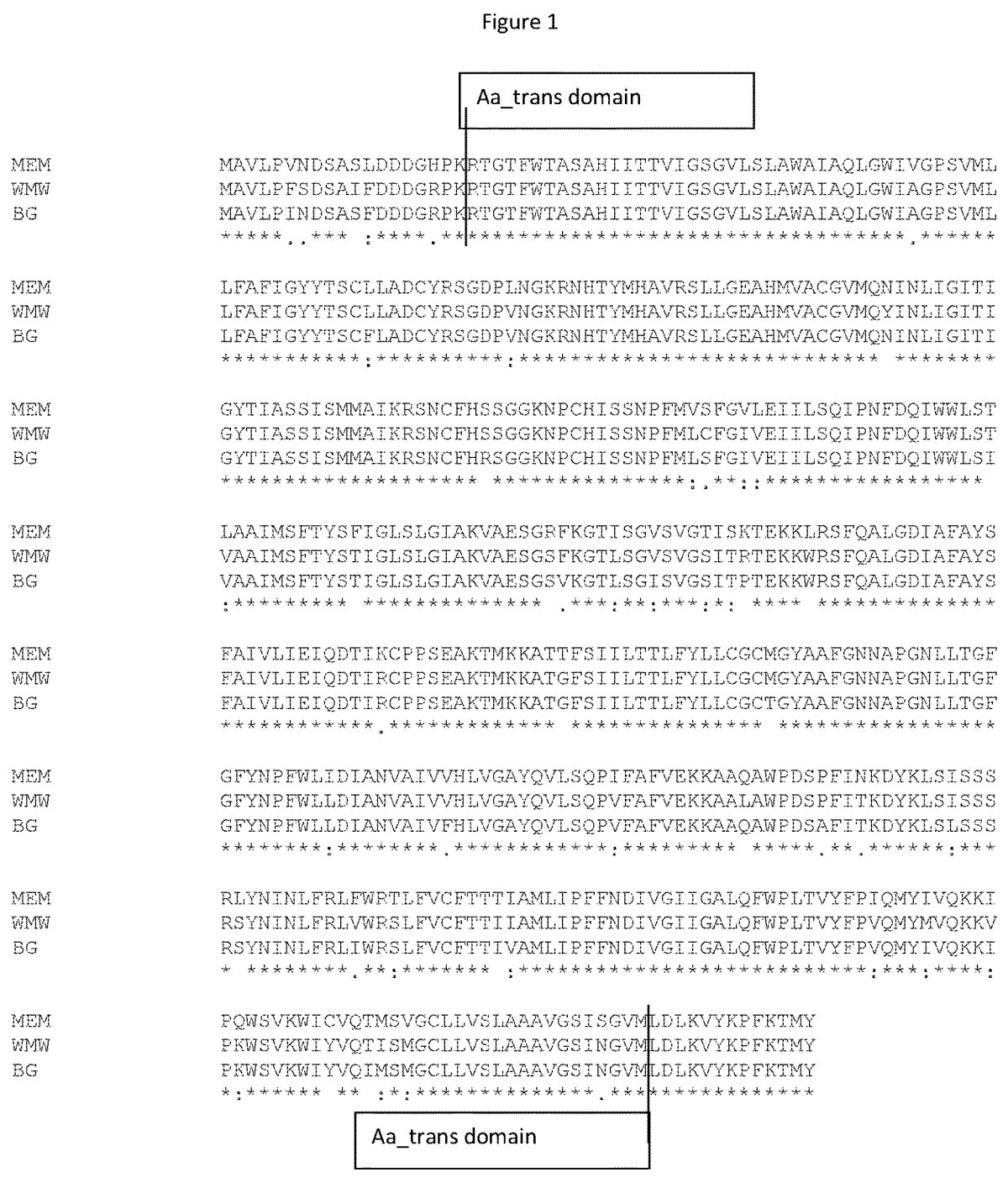

Aa_trans domain

```
MEM        MAVLPVNDSASLDDDGHPKRTGTFWTASAHIITTVIGSGVLSLAWAIAQLGWIVGPSVML
WMW        MAVLPFSDSAIFDDDGRPKRTGTFWTASAHIITTVIGSGVLSLAWAIAQLGWIAGPSVML
BG         MAVLPINDSASFDDDGRPKRTGTFWTASAHIITTVIGSGVLSLAWAIAQLGWIAGPSVML
           *****..*** :****.**********************************.******

MEM        LFAFIGYYTSCLLADCYRSGDPLNGKRNHTYMHAVRSLLGEAHMVACGVMQNINLIGITI
WMW        LFAFIGYYTSCLLADCYRSGDPVNGKRNHTYMHAVRSLLGEAHMVACGVMQYINLIGITI
BG         LFAFIGYYTSCFLADCYRSGDPVNGKRNHTYMHAVRSLLGEAHMVACGVMQNINLIGITI
           ***********:**********:**************************** ********

MEM        GYTIASSISMMAIKRSNCFHSSGGKNPCHISSNPFMVSFGVLEIILSQIPNFDQIWWLST
WMW        GYTIASSISMMAIKRSNCFHSSGGKNPCHISSNPFMLCFGIVEIILSQIPNFDQIWWLST
BG         GYTIASSISMMAIKRSNCFHRSGGKNPCHISSNPFMLSFGIVEIILSQIPNFDQIWWLSI
           ******************** ***************:.**::*****************

MEM        LAAIMSFTYSFIGLSLGIAKVAESGRFKGTISGVSVGTISKTEKKLRSFQALGDIAFAYS
WMW        VAAIMSFTYSTIGLSLGIAKVAESGSFKGTLSGVSVGSITRTEKKWRSFQALGDIAFAYS
BG         VAAIMSFTYSTIGLSLGIAKVAESGSVKGTLSGISVGSITPTEKKWRSFQALGDIAFAYS
           :********* ************** .***:**:***:*: **** **************

MEM        FAIVLIEIQDTIKCPPSEAKTMKKATTFSIILTTLFYLLCGCMGYAAFGNNAPGNLLTGF
WMW        FAIVLIEIQDTIRCPPSEAKTMKKATGFSIILTTLFYLLCGCMGYAAFGNNAPGNLLTGF
BG         FAIVLIEIQDTIRCPPSEAKTMKKATGFSIILTTLFYLLCGCTGYAAFGNNAPGNLLTGF
           ************.************* *************** *****************

MEM        GFYNPFWLIDIANVAIVVHLVGAYQVLSQPIFAFVEKKAAQAWPDSPFINKDYKLSISSS
WMW        GFYNPFWLLDIANVAIVVHLVGAYQVLSQPVFAFVEKKAALAWPDSPFITKDYKLSISSS
BG         GFYNPFWLLDIANVAIVFHLVGAYQVLSQPVFAFVEKKAAQAWPDSAFITKDYKLSLSSS
           ********:********.************:********* *****.**.******:***

MEM        RLYNINLFRLFWRTLFVCFTTTIAMLIPFFNDIVGIIGALQFWPLTVYFPIQMYIVQKKI
WMW        RSYNINLFRLVWRSLFVCFTTIIAMLIPFFNDIVGIIGALQFWPLTVYFPVQMYMVQKKV
BG         RSYNINLFRLIWRSLFVCFTTIVAMLIPFFNDIVGIIGALQFWPLTVYFPVQMYIVQKKI
           * ********.**:******* :***************************:***:****:

MEM        PQWSVKWICVQTMSVGCLLVSLAAAVGSISGVMLDLKVYKPFKTMY
WMW        PKWSVKWIYVQTISMGCLLVSLAAAVGSINGVMLDLKVYKPFKTMY
BG         PKWSVKWIYVQIMSMGCLLVSLAAAVGSINGVMLDLKVYKPFKTMY
           *:****** ** :*:**************.****************
```

Aa_trans domain

Figure 2

Aa_trans domain

```
MEM     MAVLPVNDSASFDDDGRPKRTGTFWTASAHIITAVIGSGVLSLAWAIAQLGWIAGPSVML
WMW     MAVLPINDSASFDDDGRPKRTGTFWTASAHIITAVIGSGVLSLAWAIAQLGWIAGPFVML
BG      MAVLPINDSASFDDDGRPKRTGTFWTASAHIITAVIGSGVLSLAWAIAQLGWVAGPFVML
        *****:**********************************************:*** ***

MEM     LFSFIGYYTSCLLADCYRSGDPVSGKRNPTYMHAVRSLLGETHMVACGIMQYINLIGITI
WMW     LFAFIGYYTSCLLADCYRSGDPVNGKRNHTYMHAVRSLLGEAHMVACGVMQYINLIGITI
BG      LFAFIGYYTSCLLADCYRSGDPVSGKRNYTYMHAVRSLLGEAHMVACGVMQHINLIGITI
        **:********************.**** ************:******:**:********

MEM     GYTIASSISMMAIKRSNCFHSSGGKNPCHISSNPFMLSFGIVEIILSQIPNFDQIWWLSI
WMW     GYTIASSISMMAIKRSNCFHSSGGKNPCHISSNPFMLCFGIVEIILSQIPNFDQIWWLST
BG      GYTIASSISMMAIKRSNCFHSSGGKNPCHISSNPFMLSFGIVEIILSQIPNFDQIWWLSI
        *************************************.*********************

MEM     VAAIMSFTYSSIGLTLGIAKVAESGVFKGTLSGITVGTVTQSEKIWRSFQALGDIAFAYS
WMW     VAAIMSFTYSTIGLSLGIAKVAESGSFKGTLSVISVGTITQTEKIWRSFQALGDIAFAYS
BG      VAAIMSFTYSTIGLSLGIAKVAESGSFKGTLSGVSVGTINETEKIWRSFQALGDIAFAYS
        **********:***:********** ****** ::***:.::******************

MEM     FAIVLIEVQDTIRCPPSEAKTMKKAAGFSITLTTIFYILCGCMGYAAFGNTAPGNLLTGF
WMW     FAIVLIEVQDTITCPPSEAKTMKKATGFSIALTTVFYLLCGSMGYAAFGNTAPGNLLTGF
BG      FAIVLIEVQDTIRCPPSEAKTMKKATGFSITLTTIFYMLCGTMGYAAFGNTAPGNLLTGF
        ************ ************:****:***:**:*** ******************

MEM     GFYNPFWLLDIANVSIVVHLVGAYQVFSQPVYAFVEKKVVQTWPDTPFFTKEYKLSLFSS
WMW     GFYNPFWLLDIANIAIVIHLVGAYQVFSQPVFAFVEKKATQAWPDSAVITKDHKLSLFSS
BG      GFYNPFWLLDIANVAIVVHLVGAYQVFSQPVYAFVEKKAAQAWPDSAFITKDYKLSLFSS
        *************::**:*************:******..*:***:..:**::*******

MEM     RFYNINLFRLVWRTLFVCFTTIVAMLLPFFNDIVGIIGALQFWPMTVYFPVQMYVVQKKV
WMW     HSYNINLFRLVWRSLFVCFTTIVAMLLPFFNDIVGIIGALQFWPLTVYFPVQMYIVQKKV
BG      RSYNINFFRLVWRSLFVCFTTIVAMLLPFFNDIVGIIGALQFWPLTVYFPVQMYIVQKKV
        . ****:******:******************************:*********:*****

MEM     PKWSVKWICVQTMSMGCLLISLAAAVGSISGVMLDLKVYKPFKTMY
WMW     PKWSVKWICVQTMSMGCLLISLAAVVGSVNGVMLDLKVYKPFKTMY
BG      PKWSVKWICVQTMSMGCLLISLAAVVGSINGVMLDLKVYKPFKTMY
        ************************.***:.****************
```

Aa_trans domain

Figure 3

```
                                   Aa_trans domain

CpAAP2B    MAVLPINDSSSSDDDGRPKRTGTFWTASAHIITAVIGSGVLSLAWAIAQLGWIAGPIVML
CpAAP2A    MAVLPINDAASFDDDGRPKRTGTFWTASAHIITAVIGSGVLSLAWAIAQLGWVAGPSVML
McAAP      MAMLPINDSAILDDDGRLKRTGTFWTASAHIITAVIGSGVLSLAWAIAQLGWVAGPAVML
           **:*****::  ***** **********************************:*** ***

CpAAP2B    LFAFISYYTSCLLTDCYRSNDSVNAKRNYTYMHAVRSFLGRGQTVVCGVIQYMDLIGVAI
CpAAP2A    LFAFIGYYTSCLLADCYRSSDPVNGKRNYTYMHAVRSLLGRSQTTACGVLQYVNLIGISI
McAAP      LFAFIGYYTSCLLADCYRSGDPINGKRNYTYMHAVRSLLGGAQTTACGIMQYMNLIGIAI
           *****.*******:*****.*.:*.***********:**  .**..**::**::***::*

CpAAP2B    GYTIASSISMMAVKRSNCFHKSGGKSPCRMSSNPFMVSFGVVEIILSQIPKFDQIWWLST
CpAAP2A    GYTIASAISMMAVKRSNCFHSSGGKNPCHMSSNPFMVSFGVMEIILSQIPDFDQIWWLSS
McAAP      GYTIASSISMMAIKRSNCFHSSGGKNPCHMSSNPFMISFGVMEIFLSQIPDFDQIWWLST
           ******:*****:*******.****.**.*******:****:**:*****.********:

CpAAP2B    VAAIMSFTYSTIGLALGIAKVAENGSFK--------GTVTETQKIWRTFQALGDIAFAYS
CpAAP2A    VAAVMSFTYSTIGLGLGIAKVAETGSFKGTVSGISVGTINQSQKIWRTFQALGDIAFAYS
McAAP      VAAIMSFTYSTIGLGLGIAKVAESGSFKGTLSGIGVGTVTQSQKIWRTFQALGDIAFAYS
           ***:**********.********.****        **:.:*******************

CpAAP2B    FSVILIEIQDTIRCPPSEAKTMKKASGFSIAVTTIFYLLCGCMGYAAFGNNAPGNLLTGF
CpAAP2A    FSIILIEIQDTIRCPPSEAKTMKKATGFSIALTTIFYMLCGCMGYAAFGNDAPGNLLTGF
McAAP      FSIILIEIQDTIRCPPSEAKTMKKATGLSIAVTTTFYLLCGCMGYAAFGNSAPGNLLTGF
           **:**********************:*:***:**  **:************.*********

CpAAP2B    GFYNPYWLLDIANVAIVVHLVGAYQVFCQPVFAFVEKTAAQTWPDSAFITKHYRLSLSSS
CpAAP2A    GFYNPFWLLDIANIAIVVHLVGAYQVFSQPVFAFVEKKAAQAWPDSPFITKHHKLSISSS
McAAP      GFYNPFWLLDIANVAIVVHLVGAYQVFCQPVFAFVEKKAAQAWPDSTFITKEHKLSL-FR
           *****:*******:*************.*********.***:****.****  :.**:

CpAAP2B    RSYNINFFRLVWRTLFVCFTTVVAMLLPFFNDIVGIMGAFQFWPLSVYFPVQMYIVQKKI
CpAAP2A    RSYNVNLFRLVWRSLFVCFTTVVAMLLPFFNDVVGIIGALQFWPLTVYFPVQMYIVQKKI
McAAP      RSYNVNMFRLVWRSLFVCFTTVVAMLLPFFNDVVGIIGALQFWPLTVYFPVQMYIVQKKI
           ****:*:******:******************:***:**:*****:**************

CpAAP2B    AKWSVKWVCVQTMSMGCLLISIAAGVGSLIGVVLDLKVYKPFITRY
CpAAP2A    PKWSLKWVCVQTMSMGCLLISFAAVVGSVIGVMLDLKVYKPFKTTY
McAAP      PKWSVKWVCVQTMSMGCLLISVAAAVGSVIGVMLDLKVYKPFKTRY
           .***:****************.**  ***:***:*********  *  *

                        Aa_trans domain
```

Figure 4

```
# Aligned_sequences: 2
# 1: CsAAP2A (SEQ ID NO: 19)
# 2: CmAAP2A (SEQ ID NO: 1)
# Matrix: EBLOSUM62
# Gap_penalty: 10.0
# Extend_penalty: 0.5
#
# Length: 466
# Identity:     442/466 (94.8%)
# Similarity:   454/466 (97.4%)
# Gaps:           0/466 ( 0.0%)
# Score: 2313.0


CsAAP2A SEQID19     1 MAVLPLNDSSSFDDDGHPKRTGTLWTASAHIITTVIGSGVLSLAWAIAQL     50
                        |||||:|||:|.|||||||||||.||||||||||||||||||||||||||
CmAAP2A SEQID 1     1 MAVLPVNDSASLDDDGHPKRTGTFWTASAHIITTVIGSGVLSLAWAIAQL     50

CsAAP2A            51 GWIVGPSVMLLFAFIGHYTSCLLADCYRSGDPLTGKRNPTYMHAVRSLLG    100
                        |||||||||||||||:|||||||||||||||||.||||.|||||||||||
CmAAP2A            51 GWIVGPSVMLLFAFIGYYTSCLLADCYRSGDPLNGKRNHTYMHAVRSLLG    100

CsAAP2A           101 EAHMVACGVMQNINLMGITIGYQIASSISMMAIKRSNCFHSSGGKNPCHI    150
                        |||||||||||||||:||||||.|||||||||||||||||||||||||||
CmAAP2A           101 EAHMVACGVMQNINLIGITIGYTIASSISMMAIKRSNCFHSSGGKNPCHI    150

CsAAP2A           151 SSNPFMMSFGVVEIILSQIPNFDQIWWLSTLAAIMSFTYSFIGLSLGIAK    200
                        ||||||:||||:||||||||||||||||||||||||||||||||||||||
CmAAP2A           151 SSNPFMVSFGVLEIILSQIPNFDQIWWLSTLAAIMSFTYSFIGLSLGIAK    200

CsAAP2A           201 VAESGRFKGTISGVSVGSISKTEKKLRSFQALGDIAFAYSFAIVLIEIQD    250
                        ||||||||||||||||:|||||||||||||||||||||||||||||||||
CmAAP2A           201 VAESGRFKGTISGVSVGTISKTEKKLRSFQALGDIAFAYSFAIVLIEIQD    250

CsAAP2A           251 TIKCPPSEAKTMKKATRFSIILTTLFYILCGCSGYAAFGNNAPGNLLTGF    300
                        |||||||||||||||.|||||||||||:||||.|||||||||||||||||
CmAAP2A           251 TIKCPPSEAKTMKKATTFSIILTTLFYLLCGCMGYAAFGNNAPGNLLTGF    300

CsAAP2A           301 GFYNPFWLIDIANVAIVVHLVGAYQVLSQPIFAFVEKKAAQAWPESPFIT    350
                        |||||||||||||||||||||||||||||||||||||||||||:|||||.
CmAAP2A           301 GFYNPFWLIDIANVAIVVHLVGAYQVLSQPIFAFVEKKAAQAWPDSPFIN    350

CsAAP2A           351 KEYKLSISSSHSYNINLFRLIWRSLFVCFTTTIAMLIPFFNDIVGIIGAL    400
                        |:|||||||..||||||||.||:|||||||||||||||||||||||||||
CmAAP2A           351 KDYKLSISSSRLYNINLFRLFWRTLFVCFTTTIAMLIPFFNDIVGIIGAL    400

CsAAP2A           401 QFWPLTVYFPIQMYIVQKKIRQWSVKWICVQTMSMGCLLVSLAAAVGSIS    450
                        |||||||||||||||||||||.|||||||||||||:||||||||||||||
CmAAP2A           401 QFWPLTVYFPIQMYIVQKKIPQWSVKWICVQTMSVGCLLVSLAAAVGSIS    450

CsAAP2A           451 GVMLDLKVYKPFKTMY     466
                        ||||||||||||||||
CmAAP2A           451 GVMLDLKVYKPFKTMY     466
```

DOWNY MILDEW RESISTANCE IN *CUCURBITACEAE* PLANTS

CROSS-REFERENCE TO RELATED APPLICATIONS

This application is a National Stage Entry of PCT/EP2020/063809, filed May 18, 2020, which claims priority to EP application No. 19176547.8, filed May 24, 2019, the disclosures of each of which are hereby incorporated by reference in their entirety.

FIELD

The present invention is directed to plants and plant parts of the family Cucurbitaceae, especially of the species *Cucumis melo* (melon) and *Citrullus lanatus* (watermelon) and *Lagenaria siceraria* (Bottle Gourd), but also *Cucurbita pepo* (e.g. pumpkin, squash, courgette) and *Momordica charantia* (Bitter Gourd), comprising enhanced resistance against downy mildew, caused by the Oomycete *Pseudoperonospora cubensis.*

BACKGROUND

Downy mildew of Cucurbits is caused by the Oomycete pathogen *Pseudoperonospora cubensis* (Berk. et Curt.) and is one of the most destructive diseases on Cucurbitaceae. *P. cubensis* is an obligate pathogen, which is spread through dispersal of sporangia by wind and rain. Symptoms first appear on adaxial surfaces of leaves as light green or yellow lesions restricted by the leaf veins. Later, the lesions become chlorotic and necrotic, which causes a severe reduction in photosynthesis and eventually the leaf dies. Light greyish-blue sporangiophores develop on the infected leaves. Each sporangiophore terminates with a sporangium, in which zoospores are produced, which can enter leaf tissue through stomata and establish infection. Plants which are severely infected produce small and misshapen fruits, which are not marketable. Late season infection results in fruits having a reduced sugar content, reducing fruit prices. Disease symptoms become visible about 4 to 12 days after infection.

Control of downy mildew is primarily through use of resistant varieties and/or fungicide spray programs. Fungicides are most effective when they are sprayed prior to the first symptoms appearing. In cucumber a single recessive gene named dm-1, derived from the Indian accession PI197087, has been used to develop downy mildew resistant cucumber varieties. Recently a missense mutation in the gene CsSGR (Staygreen gene) was found to be causal for the dm-1 resistance. As new strains of *P. cubensis* developed since 2004, which have partially overcome the dm-1 resistance, new sources of downy mildew resistance were sought after. Chen and Wang (2008, Plant Pathology Bulletin 17, 1, p 76) found the accession PI197088 to contain high resistance against downy mildew and powdery mildew. Several groups discovered that downy mildew resistance in PI197088 is polygenic, as multiple QTLs (Quantitative trait loci) contribute to the resistance. However, different groups reached different conclusions regarding the number and chromosomal locations of QTLs which contribute to the overall resistance of PI197088.

Yoshioka et al. (Euphytica, 2014, 198: 265-276) mapped seven QTLs for downy mildew resistance from PI197088 on chromosomes 1, 3 and 5. Li et al. (Plant Dis. 2017, 102:1-6) mapped 5 QTLs for downy mildew resistance from PI197088 on chromosomes 1, 3, 4 and 5.

Wang et al. (Theor Appl Genetic 2018, 131: 597-611) identified 11 QTLs for downy mildew resistance from PI197088 on chromosomes 1 to 6.

WO200912314 describes a QTL for downy mildew resistance from PI197088 on chromosome 5.

WO2011050296 describes QTLs for downy mildew resistance from PI197088 on chromosomes 2, 4 and 5.

In melon resistance to downy mildew was found to be present in PI124111 and PI124112. The resistance in PI124111 was attributed to a 45 kD protein present in the resistant line, but absent in the susceptible line, and two aminotransferase encoding genes At1 and At2 were identified, which were responsible for the downy mildew resistance (Taler et al. 2004, Plant Cell 16: 172-184).

Apart from the problem that breeding for quantitative resistance requires the combination of multiple QTLs, using wild accessions or landraces in breeding for resistance poses the additional problem that large chromosome regions are introgressed into the cultivated material, thereby introducing undesirable traits in the form of what is referred to as linkage drag. Knowing causal genes, underlying QTLs, would enable the direct modification of those genes in elite, cultivated lines and would also overcome the problem of linkage drag. In addition, while introgression is species limited, knowledge of the resistance underlying genes enables identification of the orthologs in other species and modification of those orthologs to generate downy mildew resistance.

There is, thus, a need to identify genes which, when modified in cultivated plants, enhance resistance to downy mildew.

FIGURES

FIG. 1—alignment of melon (abbreviated MEM; SEQ ID NO: 1) and watermelon (abbreviated WMW; SEQ ID NO: 2) and Bottle Gourd (abbreviated BG; SEQ ID NO: 3) AAP2A proteins. The Aa_trans domain is indicated, starting at amino acid 20 and ending at amino acid 453.

FIG. 2—alignment of melon (abbreviated MEM; SEQ ID NO: 4) and watermelon (abbreviated WMW; SEQ ID NO: 5) and Bottle Gourd (abbreviated BG; SEQ ID NO: 6) AAP2B proteins. The Aa_trans domain is indicated, starting at amino acid 20 and ending at amino acid 453.

FIG. 3—alignment of *C. pepo* AAP2A (CpAAP2A, SEQ ID NO: 14) and AAP2B (CpAAP2B, SEQ ID NO: 15) and Bitter Gourd (McAAP, SEQ ID NO: 13) AAP proteins. The Aa_trans domain is indicated. For SEQ ID NO: 13 it is from amino acid 20 to 452; for SEQ ID NO: 14 it is from amino acid 20 to 453 and SEQ ID NO: 15 it is from amino acid 20 to 445.

FIG. 4—pairwise alignment of CsAAP2A protein (SEQ ID NO: 19) and CmAAP2A protein (SEQ ID NO: 1)

GENERAL DEFINITIONS

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells, plants, etc. Similarly, "a fruit" or "a plant" also refers to a plurality of fruits and plants.

A "plant line" or "breeding line" refers to a plant and its progeny. As used herein, the term "inbred line" refers to a plant line which has been repeatedly selfed, as a result of this selfing, plants of an inbred line are nearly identical to each other in genotype and phenotype.

As used herein, the term "mutant allele of a gene" refers to a mutant allele of a gene, said mutant allele either encodes a protein which, compared to the protein encoded by the wild type allele of the gene, comprises one or more amino acids replaced, deleted or inserted, whereby the mutant allele produces a mutant protein which has a "reduced-function" or "loss-of-function", or said mutant allele of the gene has a reduced gene expression or even no expression compared to the gene expression of the wild type (non-mutated) allele of the gene.

"Susceptibility gene" or "S-gene" of a plant refers to an endogenous, dominant gene of a plant, which plays a role in disease symptom development following pathogen infection. Consequently, when such a gene is mutated, the susceptibility of the plant is reduced (or, in other words, the resistance is increased) and less symptoms develop at least when the mutated recessive allele is in homozygous form compared to the plant comprising the wild type allele of the S-gene.

As used herein, "resistance against *Pseudoperonospora cubensis*" or "resistance against downy mildew" refers to a plant line or variety comprising (statistically significant) reduced symptoms after infection or inoculation with *P. cubensis* compared to a susceptible control plant line or variety. "Resistance against *P. cubensis*" encompasses also in one aspect "partial resistance against *P. cubensis*" or "reduced susceptibility to *P. cubensis*", whereby e.g. leaf yellowing (chlorosis) and/or sporulation is significantly less in the partial resistant/less susceptible line or variety compared to a susceptible control plant line or variety. A disease assays to measure resistance against *P. cubensis* is described in the Examples.

As used herein, the term "plant" includes the whole plant or any parts or derivatives thereof, preferably having the same genetic makeup as the plant from which it is obtained, such as plant organs (e.g. harvested or non-harvested fruits, leaves, etc.), plant cells, plant protoplasts, plant cell- or tissue-cultures from which whole plants can be regenerated, plant calli, plant cell clumps, plant transplants, seeds from which the plant can be grown and seeds produced by the plant, seedlings, plant cells that are intact in plants, plant clones or micropropagations, or parts of plants, such as plant cuttings, embryos, pollen, ovules, fruits (e.g. harvested tissues or organs), flowers, leaves, clonally propagated plants, roots, stems, root tips, grafts (scions and/or root stocks) and the like. Also any developmental stage is included, such as seedlings, cuttings prior or after rooting, etc. As used herein, the term plant includes plant and plant parts comprising one or more of the mutant alleles of the invention.

In one aspect, the term plant part refers to plant cells, or plant tissues or plant organs that comprise one or more of the mutant alleles of the invention. In one aspect a plant part can grow into a plant and/or live on photosynthesis (i.e. synthesizing carbohydrate and protein from the inorganic substance, such as water, carbon dioxide and mineral salt). In another aspect, a plant part cannot grow into a plant and/or live on photosynthesis (i.e. synthesizing carbohydrate and protein from the inorganic substance, such as water, carbon dioxide and mineral salt). Thus, a plant part can be propagating or non-propagating.

As used herein, the term "variety" or "cultivar" or "plant variety" means a plant grouping within a single botanical taxon of the lowest known rank, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one locus or gene or two loci or genes, but which can otherwise differ from one another enormously as regards the other loci or genes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Vegetative propagation" refers to propagation of plants from vegetative tissue, e.g. by in vitro propagation or grafting methods (using scions).

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 8, 9, 10, 15, 20, 30, 40, 50 or more plants (or plant parts) are measured, preferably in randomized experimental designs with several replicates and suitable control plants grown under the same conditions in the same experiment.

"Statistically significant" or "statistically significantly" different or "significantly" different refers to a characteristic of a plant line or variety that, when compared to a suitable control (e.g. the genetic control) show a statistically significant difference in that characteristic (e.g. the p-value is less than 0.05, $p<0.05$, using ANOVA) from the mean of the control.

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA or an RNAi molecule) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. A gene may be an endogenous gene (in the species of origin) or a chimeric gene (e.g. a transgene or cis-gene).

"Expression of a gene" refers to the process wherein a DNA region, which is operably linked to appropriate regulatory regions, particularly a promoter, is transcribed into an RNA.

An "active protein" or "functional protein" is a protein which has protein activity as measurable in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation(s) results in (the mutant allele encoding) a "reduced-function" or "loss-of-function" protein, as e.g. measurable in vivo, e.g. by the phenotype conferred by the mutant allele (in homozygous form).

A "reduced function AAP2A or AAP2B protein" or "reduced activity AAP2A or AAP2B protein" refers to a mutant protein which has a reduced activity and confers *P. cubensis* resistance or at least partial resistance in a plant comprising such reduced function protein at least when the allele encoding the mutant protein is present in homozygous form compared to a control plant comprising the wild type allele in homozygous form. Likewise a loss-of-function AAP2A or AAP2B protein refers to a protein which has no activity and confers *P. cubensis* resistance or at least partial resistance in a plant comprising such loss-of-function protein at least when the allele encoding the mutant protein is present in homozygous form compared to a control plant comprising the wild type allele in homozygous form.

"Induced mutant alleles" are mutant alleles in which the mutation(s) is/are/have been induced by human intervention, e.g. by mutagenesis via physical or chemical mutagenesis methods, or via e.g. tissue culture (as described in e.g. Zhang et al, Plos 9(5) e96879), including also genome editing techniques.

"Natural mutant alleles" are mutant alleles in which the mutation(s) have evolved in wild plants or wild relatives of a species or landraces. Such natural mutant alleles can be introgressed into cultivated plants by crossing and selection. For example an allele comprising a transposable element (TE) insertion is a natural mutant allele, or an allele encoding a truncated protein compared to the wild type protein may be a natural mutant allele.

A "mutation" in a nucleic acid molecule coding for a protein is a change of one or more nucleotides compared to the wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "point mutation" is the replacement of a single nucleotide, or the insertion or deletion of a single nucleotide.

A "nonsense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "missense" or non-synonymous mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation in a nucleic acid sequence encoding a protein by which the reading frame of the mRNA is changed, resulting in a different amino acid sequence. The resulting protein may have reduced function or loss of function.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made. In one aspect a mutation in a regulatory sequence of a protein includes a lower level of wild type protein (e.g. due to a lower expression of the allele) or no wild type protein being made (no expression of the allele). Mutations in regulatory elements, such as promoters, can be generated by e.g. CRISPR/Cas. Rodriguez-Leal et al., 2017, Cell 171, 470-480 describe for example mutating cis-regulatory elements to create a continuum of mutant alleles with different expression.

A "mutation" in a protein is a change of one or more amino acid residues compared to the wild type sequence, e.g. by replacement, deletion or insertion of one or more amino acid residues.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpin RNA capable of silencing the endogenous target gene expression). In mutagenesis or targeted genome editing approaches, a target gene is the endogenous gene which is to be mutated (and/or in which mutations are selected by e.g. TILLING) or edited, leading to a change in (reduction or loss of) gene expression or a change in (reduction or loss of) function of the encoded protein.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

The term “heterozygous” refers to a plant or plant cell having dissimilar pairs of alleles of a gene for any hereditary characteristic. The term “homozygous” or in “homozygous form” refers to a plant or plant cell or plant part (e.g. a fruit) having identical alleles of a gene for any hereditary characteristic, e.g. a diploid plant or plant part homozygous for the mutant AAP2A and/or AAP2B allele comprises two copies of the allele in its genome.

It is understood that comparisons between different plant lines involves growing a number of plants of a line (e.g. at least 8 plants, preferably at least 10 plants per line) under the same conditions as the plants of one or more control plant lines (e.g. plants comprising the wild type allele or plants having the same genetics as the line it is compared with except that the wild type allele is present in homozygous form instead of the mutant allele) and the determination of statistically significant differences between the plant lines when grown under the same environmental conditions and when treated in the same way, e.g. inoculated leaves with *P. cubensis* in a disease assay and assessing the disease symptoms after a certain number of says, e.g. when the susceptible control shows prominent symptoms.

“Stringent hybridization conditions” can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions.

“Sequence identity” and “sequence similarity” can be determined by alignment of two peptide or two nucleotide sequences using global or local alignment algorithms. Sequences may then be referred to as “substantially identical” or “essentially similar” when they are optimally aligned by for example the programs GAP or BESTFIT or the Emboss program “Needle” (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, accessible at world wide web under ebi.ac.uk/Tools/emboss/. Alternatively sequence identity may be determined by searching against databases such as FASTA, BLAST, etc., but hits should be retrieved and aligned pairwise to compare sequence identity. Two proteins or two protein domains, or two nucleic acid sequences have “substantial sequence identity” if the percentage sequence identity is at least 90%, 91%, 93%, 94%, 95%, 96%, 97%, 98% or 99% or more (as determined by Emboss “needle” using default parameters, i.e. gap creation penalty=10, gap extension penalty=0.5, using scoring matrix DNAFULL for nucleic acids an Blosum62 for proteins). Such sequences are also referred to as ‘variants’ herein, e.g. other allelic variants of the AAP2A or AAP2B alleles and AAP2A or AAP2B proteins than the specific nucleic acid and protein sequences disclosed herein can be identified. Mutations in such allelic variants have the same effect on resistance to *P. cubensis* in plants comprising such variants and cultivated plants comprising mutations in such variants are embodiments of the invention.

“AAP2A allele” refers to an allele encoding an amino acid permease protein. The two letter code preceding AAP2A may be used to indicate the species comprising the allele (Cm—*Cucumis melo*; Cl—*Citrullus lanatus*, Ls—*Lagenaria siceraria*; Cp—*Cucurbita pepo*; Mc—*Momordica charantia*).

“AAP2B allele” refers to an allele encoding an amino acid permease protein. The two letter code preceding AAP2B may be used to indicate the species comprising the allele (Cm—*Cucumis melo*; Cl—*Citrullus lanatus*, Ls—*Lagenaria siceraria*; Cp—*Cucurbita pepo*; Mc—*Momordica charantia*).

“Wild type CmAAP2A allele” (WT) refers herein to a version of a gene encoding a fully functional melon CmAAP2A protein (wild type CmAAP2A protein). A sequence encoding a fully functional CmAAP2A protein of SEQ ID NO: 1 is for example the wild type CmAAP2A cDNA (mRNA) sequence depicted in SEQ ID NO: 7, or the wild type CmAAP2A genomic sequence encoding the mRNA/cDNA sequence of SEQ ID NO: 7. The protein sequence encoded by this wild type CmAAP2A mRNA is depicted in SEQ ID NO: 1. It consists of 466 amino acids. Other fully functional CmAAP2A protein-encoding alleles (i.e. variant alleles, or allelic variants) may exist in other melon plants or wild melon or wild relatives of melon and may comprise substantial sequence identity with SEQ ID NO: 1, i.e. at least about 90%, 91%, 93%, 94%, 95%, 96%, 97%, 98% or 99% sequence identity with SEQ ID NO: 1. Such fully functional wild type CmAAP2A proteins are herein referred to as “variants” of SEQ ID NO: 1.

“Wild type CmAAP2B allele” (WT) refers herein to a version of a gene encoding a fully functional melon AAP2B protein (wild type CmAAP2B protein). Such a sequence encoding a fully functional CmAAP2B protein of SEQ ID NO: 4 is for example the wild type CmAAP2B cDNA (mRNA) sequence depicted in SEQ ID NO: 8, or the wild type CmAAP2B genomic sequence encoding the mRNA/cDNA sequence of SEQ ID NO: 8. The protein sequence encoded by this wild type CmAAP2B mRNA is depicted in SEQ ID NO: 4. It consists of 466 amino acids. Other fully functional CmAAP2B protein-encoding alleles (i.e. variant alleles, or allelic variants) may exist in other melon plants or wild melon or wild relatives of melon and may comprise substantial sequence identity with SEQ ID NO: 4, i.e. at least about 90%, 91%, 93%, 94%, 95%, 96%, 97%, 98% or 99% sequence identity with SEQ ID NO: 4. Such fully functional wild type CmAAP2B proteins are herein referred to as "variants" of SEQ ID NO: 4.

"Wild type ClAAP2A allele" (WT) refers herein to a version of a gene encoding a fully functional watermelon ClAAP2A protein (wild type ClAAP2A protein). A sequence encoding a fully functional ClAAP2A protein of SEQ ID NO: 2 is for example the wild type ClAAP2A cDNA (mRNA) sequence depicted in SEQ ID NO: 9, or the wild type ClAAP 2A genomic sequence encoding the mRNA/cDNA sequence of SEQ ID NO: 9. The protein sequence encoded by this wild type ClAAP2A mRNA is depicted in SEQ ID NO: 2. It consists of 466 amino acids. Other fully functional ClAAP2A protein-encoding alleles (i.e. variant alleles, or allelic variants) may exist in other watermelon plants or wild watermelon or wild relatives of watermelon and may comprise substantial sequence identity with SEQ ID NO: 2, i.e. at least about 90%, 91%, 93%, 94%, 95%, 96%, 97%, 98% or 99% sequence identity with SEQ ID NO: 2. Such fully functional wild type ClAAP2A proteins are herein referred to as "variants" of SEQ ID NO: 2.

"Wild type ClAAP2B allele" (WT) refers herein to a version of a gene encoding a fully functional watermelon AAP2B protein (wild type ClAAP2B protein). Such a sequence encoding a fully functional ClAAP2B protein of SEQ ID NO: 5 is for example the wild type ClAAP2B cDNA (mRNA) sequence depicted in SEQ ID NO: 10, or the wild type ClAAP2B genomic sequence encoding the mRNA/cDNA sequence of SEQ ID NO: 10. The protein sequence encoded by this wild type ClAAP2B mRNA is depicted in SEQ ID NO: 5. It consists of 466 amino acids. Other fully functional ClAAP2B protein-encoding alleles (i.e. variant alleles, or allelic variants) may exist in other watermelon plants or wild watermelon or wild relatives of watermelon and may comprise substantial sequence identity with SEQ ID NO: 5, i.e. at least about 90%, 91%, 93%, 94%, 95%, 96%, 97%, 98% or 99% sequence identity with SEQ ID NO: 5. Such fully functional wild type ClAAP2B proteins are herein referred to as "variants" of SEQ ID NO: 5.

"Wild type LsAAP2A allele" (WT) refers herein to a version of a gene encoding a fully functional bottle gourd LsAAP2A protein (wild type LsAAP2A protein). A sequence encoding a fully functional LsAAP2A protein of SEQ ID NO: 3 is for example the wild type LsAAP2A cDNA (mRNA) sequence depicted in SEQ ID NO: 11, or the wild type LsAAP2A genomic sequence encoding the mRNA/cDNA sequence of SEQ ID NO: 11. The protein sequence encoded by this wild type LsAAP2A mRNA is depicted in SEQ ID NO: 3. It consists of 466 amino acids. Other fully functional LsAAP2A protein-encoding alleles (i.e. variant alleles, or allelic variants) may exist in other bottle gourd plants or wild bottle gourd or wild relatives of bottle gourd and may comprise substantial sequence identity with SEQ ID NO: 3, i.e. at least about 90%, 91%, 93%, 94%, 95%, 96%, 97%, 98% or 99% sequence identity with SEQ ID NO: 3. Such fully functional wild type LsAAP2A proteins are herein referred to as "variants" of SEQ ID NO: 3.

"Wild type LsAAP2B allele" (WT) refers herein to a version of a gene encoding a fully functional bottle gourd AAP2B protein (wild type LsAAP2B protein). Such a sequence encoding a fully functional LsAAP2B protein of SEQ ID NO: 6 is for example the wild type LsAAP2B cDNA (mRNA) sequence depicted in SEQ ID NO: 12, or the wild type LsAAP2B genomic sequence encoding the mRNA/cDNA sequence of SEQ ID NO: 12. The protein sequence encoded by this wild type LsAAP2B mRNA is depicted in SEQ ID NO: 6. It consists of 466 amino acids.

Other fully functional LsAAP2B protein-encoding alleles (i.e. variant alleles, or allelic variants) may exist in other bottle gourd plants or wild bottle gourd or wild relatives of bottle gourd and may comprise substantial sequence identity with SEQ ID NO: 6, i.e. at least about 90%, 91%, 93%, 94%, 95%, 96%, 97%, 98% or 99% sequence identity with SEQ ID NO: 6. Such fully functional wild type LsAAP2B proteins are herein referred to as "variants" of SEQ ID NO: 6.

"Wild type CpAAP2A allele" (WT) refers herein to a version of a gene encoding a fully functional *Cucurbita pepo* CpAAP2A protein (wild type CpAAP2A protein). A sequence encoding a fully functional CpAAP2A protein of SEQ ID NO: 14 is for example the wild type CpAAP2A cDNA (mRNA) sequence depicted in SEQ ID NO: 17, or the wild type CpAAP2A genomic sequence encoding the mRNA/cDNA sequence of SEQ ID NO: 17. The protein sequence encoded by this wild type CpAAP2A mRNA is depicted in SEQ ID NO: 14. It consists of 466 amino acids. Other fully functional CpAAP2A protein-encoding alleles (i.e. variant alleles, or allelic variants) may exist in other *C. pepo* plants or wild *C. pepo* or wild relatives of *C. pepo* and may comprise substantial sequence identity with SEQ ID NO: 14, i.e. at least about 90%, 91%, 93%, 94%, 95%, 96%, 97%, 98% or 99% sequence identity with SEQ ID NO: 14. Such fully functional wild type CpAAP2A proteins are herein referred to as "variants" of SEQ ID NO: 14.

"Wild type CpAAP2B allele" (WT) refers herein to a version of a gene encoding a fully functional *C. pepo* AAP2B protein (wild type CpAAP2B protein). Such a sequence encoding a fully functional CpAAP2B protein of SEQ ID NO: 15 is for example the wild type CpAAP2B cDNA (mRNA) sequence depicted in SEQ ID NO: 18, or the wild type CpAAP2B genomic sequence encoding the mRNA/cDNA sequence of SEQ ID NO: 18. The protein sequence encoded by this wild type CpAAP2B mRNA is depicted in SEQ ID NO: 15. It consists of 458 amino acids. Other fully functional CpAAP2B protein-encoding alleles (i.e. variant alleles, or allelic variants) may exist in other *C. pepo* plants or wild *C. pepo* or wild relatives of *C. pepo* and may comprise substantial sequence identity with SEQ ID NO: 15, i.e. at least about 90%, 91%, 93%, 94%, 95%, 96%, 97%, 98% or 99% sequence identity with SEQ ID NO: 15. Such fully functional wild type CpAAP2B proteins are herein referred to as "variants" of SEQ ID NO: 15.

"Wild type McAAP allele" (WT) refers herein to a version of a gene encoding a fully functional *Momordica charantia* (bitter gourd) AAP protein (wild type McAAP protein). Such a sequence encoding a fully functional McAAP protein of SEQ ID NO: 13 is for example the wild type McAAP cDNA (mRNA) sequence depicted in SEQ ID NO: 16, or the wild type McAAP genomic sequence encoding the mRNA/cDNA sequence of SEQ ID NO: 16. The protein sequence encoded by this wild type McAAP mRNA is depicted in SEQ ID NO: 13. It consists of 465 amino acids. Other fully functional McAAP protein-encoding alleles (i.e. variant alleles, or allelic variants) may exist in other bitter gourd plants or wild bitter gourd or wild relatives of bitter gourd and may comprise substantial sequence identity with SEQ ID NO: 13, i.e. at least about 90%, 91%, 93%, 94%, 95%, 96%, 97%, 98% or 99% sequence identity with SEQ ID NO: 13. Such fully functional wild type McAAP proteins are herein referred to as "variants" of SEQ ID NO: 13.

"A_trans domain" or "Amino Acid Transporter Domain" is a conserved protein domain which is involved in transmembrane amino acid transport. The protein is thus a transmembrane protein, i.e. it spans a membrane to transport amino acids across the membrane. It can be identified by having high sequence identity with the Pfam domain PF01490, e.g. by doing a sequence analysis on the world wide web at pfam.xfam.org or by analysing the sequence in InterPro, on the www site ebi.ac.uk/interpro/search/sequence-search. The proteins CmAAP2A (SEQ ID NO: 1), ClAAP2A (SEQ ID NO: 2), LsAAP2A (SEQ ID NO:3), CmAAP2B (SEQ ID NO: 4), ClAAP2B (SEQ ID NO: 5), LsAAP2B (SEQ ID NO: 6) and CpAAP2A (SEQ ID NO: 14) contain an Aa_trans domain starting at amino acid 20 and ending at amino acid 453. The CpAAP2B protein (SEQ ID NO: 15) comprises an Aa_trans domain starting at amino acid 20 and ending at amino acid 445, because this protein comprises 8 amino acids less than the melon, watermelon and bottle gourd AAP2B proteins (see FIG. 3). The McAAP protein (SEQ ID NO: 13) comprises an Aa_trans domain starting at amino acid 20 and ending at amino acid 452. See FIGS. 1, 2 and 3. In 3-D structure, the Aa_trans domain contains largely helices. For example the above proteins all have a predicted 3-D structure that is 66%, 67% or 68% helix, 0% beta sheet and 31%, 32% or 33% loop/coil (raptorx.uchicago.edu).

"Melon plant" or "cultivated melon" or "domesticated melon" refers to plants of *Cucumis melo* L. i.e. varieties, breeding lines or cultivars, cultivated by humans and having good agronomic characteristics, especially producing edible and marketable fruits of good size and quality and uniformity; such cultivated melon plants may for example be further classified as *C. melo* var. cantalupensis, *C. melo* var. inodorous and *C. melo* var. reticulatus; such plants are not "wild melon" or "primitive melon" plants, i.e. plants which generally have much poorer yields and poorer agronomic characteristics than cultivated plants and are less uniform genetically and in their physiological and/or morphological characteristics. "Wild plants" or "wild melon" include for example ecotypes, landraces or wild accessions or wild relatives of a species, such as for example accessions of *Cucumis melo* ssp. agrestis, *C. melo* ssp. melo, *C. melo* ssp. acidulous, C. callosus, C. trigonus, C. picrocarpus, *Cucumis melo* var. *momordica*, or other wild melon or wild relative of melon producing e.g. fruits of poor quality and/or poor uniformity.

"Watermelon plant" or "cultivated watermelon" or "domesticated watermelon" or "*Citrullus lanatus*" refers to plants of *Citrullus lanatus* ssp. vulgaris, i.e. varieties, breeding lines or cultivars, cultivated by humans and having good agronomic characteristics, especially producing edible and marketable fruits of good size and quality and uniformity; such plants are not "wild watermelon" or "primitive watermelon" plants, i.e. plants which generally have much poorer yields and poorer agronomic characteristics than cultivated plants and are less uniform genetically and in their physiological and/or morphological characteristics. "Wild plants" or "wild watermelon" include for example ecotypes, landraces or wild accessions or wild relatives of a species, such as for example accessions of *Citrullus lanatus* ssp. lanatus, *Citrullus lanatus* ssp. *mucosospermus, Citrullus colocynthis*, or plants of the citroides group (e.g. *C. lanatus* var. *citroides*) producing e.g. fruits of poor quality and/or poor uniformity.

"*Cucurbita pepo* plant" or "cultivated *C. pepo*" or "domesticated *C. pepo*" refers to plants of *C. pepo*, i.e. varieties, breeding lines or cultivars, cultivated by humans and having good agronomic characteristics, especially producing edible and marketable fruits of good size and quality and uniformity; examples are breeding lines or varieties or cultivars of pumpkin (*C. pepo* subsp. pepo), squash, zucchini or courgette, marrows, etc.; such plants are not "wild" or "primitive" plants, i.e. plants which generally have much poorer yields and poorer agronomic characteristics than cultivated plants and are less uniform genetically and in their physiological and/or morphological characteristics. "Wild plants" include for example ecotypes, landraces or wild accessions or wild relatives of a species, such as for example accessions of C. texana, C. fraterna, *C. pepo* subsp fraterna, *C. pepo* subsp olifera var. texana, etc. producing e.g. fruits of poor quality and/or poor uniformity.

"Landrace(s)" refers to primitive cultivars developed in local geographic regions, which often show a high degree of genetic variation in their genome and exhibit a high degree of morphological and/or physiological variation within the landrace (e.g. large variation in fruit size, etc.), i.e. are significantly less uniform than cultivated plants. Landraces are, therefore, herein included in the group "wild" plants, which is distinct from "cultivated" plants.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

"Uniformity" or "uniform" relates to the genetic and phenotypic characteristics of a plant line or variety. Inbred lines are genetically highly uniform as they are produced by several generations of inbreeding. Likewise the F1 hybrids which are produced from crossing two such inbred lines are highly uniform in their genotypic and phenotypic characteristics and performance.

A "recombinant chromosome" refers to a chromosome having a new genetic makeup arising through crossing-over between homologous chromosomes. Herein, for example, recombinant chromosome is provided comprising an introgression fragment from a wild plant, which introgression fragment comprises a natural mutant allele.

The term "traditional breeding techniques" encompasses herein crossing, backcrossing, selfing, selection, double haploid production, embryo rescue, protoplast fusion, marker assisted selection, mutation breeding etc., all as known to the breeder (i.e. methods other than genetic modification/transformation/transgenic methods), by which, for example, a recombinant chromosome can be obtained, identified and/or transferred.

"Backcrossing" refers to a breeding method by which a (single) trait, such as a mutant allele, can be transferred from a generally (but not necessarily) inferior genetic background (e.g. a wild plant or wild relative; also referred to as "donor") into a generally (but not necessarily) superior genetic background (also referred to as "recurrent parent"), e.g. a cultivated plant. An offspring of a cross (e.g. an F1 plant obtained by crossing a donor plant with a e.g. superior genetic background plant; or an F2 plant or F3 plant, etc., obtained from selfing the F1) is e.g. "backcrossed" to the recurrent parent genetic background, e.g. to the cultivated parent. After repeated backcrossing, the trait of the donor genetic background will have been incorporated into the recurrent parent genetic background.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation. In one aspect propagation by grafting, e.g. a scion onto a rootstock, is included herein.

"Cell culture" or "tissue culture" refers to the in vitro culture of cells or tissues of a plant.

"Regeneration" refers to the development of a plant from cell culture or tissue culture or vegetative propagation.

"Non-regenerable cell" refers to a cell which cannot be regenerated into a whole plant.

DETAILED DESCRIPTION

The present invention relates in one aspect to the identification of an S-gene (susceptibility gene) class in Cucurbitaceae plants, especially in melon, watermelon, bottle gourd (*Lagenaria siceraria*), *Cucurbita pepo* and bitter gourd (*Momordica charantia*).

It was found that Cucurbitaceae plants of the species melon, watermelon, bottle gourd and *Cucurbita pepo* contain an S-gene, which encoded an Amino Acid Permease protein, referred herein to as AAP2A, which when mutated resulted in reduced susceptibility (or partial resistance) to the oomycete *P. cubensis*, at least when the mutant allele is in homozygous form (the wild type AAP2A allele is written in capital letters herein, and the mutant aap2a allele in small letters). The AAP2A proteins encoded by the AAP2A genes of melon, watermelon bottle gourd and *C. pepo* have a amino acid sequence identity of at least 84% (using the program Needle).

It was further found that melon, watermelon, bottle gourd and *Cucurbita pepo* plants contained a second Amino Acid Permease gene, which encoded a protein that had very high amino acid sequence identity to the AAP2A protein, and this second gene is referred to as AAP2B. This second gene, when mutated, is thought to also result in reduced susceptibility (or partial resistance) to the oomycete *P. cubensis*, at least when the mutant allele was in homozygous form. The AAP2B proteins encoded by the AAP2B genes of melon, watermelon bottle gourd and *C. pepo* have a amino acid sequence identity of at least 80% (using the program Needle).

Also, AAP2A and AAP2B proteins have the same structure and all comprise a AA_trans domain, see FIGS. 1-3.

The table below shows the sequence identity of AAP2A proteins of different Cucurbitaceae species.

| | watermelon | Bottle gourd | *C. pepo* |
|---|---|---|---|
| melon | 91.8% | 91.2% | 84.1% |
| watermelon | | 95.3% | 86.1% |
| Bottle gourd | | | 86.1% |

The table below shows the sequence identity of AAP2B proteins of different Cucurbitaceae species.

| | watermelon | Bottle gourd | *C. pepo* |
|---|---|---|---|
| melon | 90.8% | 92.5% | 80.9% |
| watermelon | | 94.8% | 82.4% |
| Bottle gourd | | | 83.3% |

Thus, in one aspect the invention relates to a plant of the species melon (*Cucumis melo*), watermelon (*Citrullus lanatus*), bottle gourd (*Lagenaria siceraria*) and *Cucurbita pepo* comprising at least one copy of a mutant allele of a gene named AAP2A, wherein said mutant allele results in reduced expression or no expression of the AAP2A gene or wherein the mutant allele encodes a protein having decreased function or a loss-of-function compared to the wild type AAP2A protein.

In another aspect the invention relates to a plant of the species melon (*Cucumis melo*), watermelon (*Citrullus lanatus*), bottle gourd (*Lagenaria siceraria*) and *Cucurbita pepo* comprising at least one copy of a mutant allele of a gene named AAP2B, wherein said mutant allele results in reduced expression or no expression of the AAP2B gene or wherein the mutant allele encodes a protein having decreased function or a loss-of-function compared to the wild type AAP2B protein.

Plants comprising mutant alleles in either the endogenous AAP2A gene or in the endogenous AAP2B gene are encompassed herein, but also plants comprising mutant alleles of both the AAP2A and AAP2B gene are encompassed herein.

Thus a further aspect of the invention relates to a plant of the species melon (*Cucumis melo*), watermelon (*Citrullus lanatus*), bottle gourd (*Lagenaria siceraria*) and *Cucurbita pepo* comprising at least one copy of a mutant allele of a gene named AAP2A and/or at least one copy of a mutant allele named AAP2B, wherein said mutant aap2a allele results in reduced expression or no expression of the AAP2A gene or wherein the mutant aap2a allele encodes a protein having decreased function or a loss-of-function compared to the wild type AAP2A protein, and wherein the mutant aap2b allele results in reduced expression or no expression of the AAP2B gene or wherein the mutant aap2b allele encodes a protein having decreased function or a loss-of-function compared to the wild type AAP2B protein.

Plants may either comprise only one copy of the mutant allele of the aap2a and/or of the aap2b gene, i.e. they may be heterozygous for the mutant allele, or preferably they comprise two copies of the mutant allele of the aap2a and/or aap2b gene, i.e. they are homozygous for the mutant allele.

Apart from the de novo generation of (induced) mutant aap2a and aap2b alleles, the invention also enables screening of wild plants (e.g. landraces, PI accessions, CGN accessions, etc.) for the presence of "natural mutant" alleles. Such newly found natural mutant aap2a and/or aap2b alleles can then be introgressed into the cultivated Cucurbitaceae plant, to generate cultivated plants comprising reduced susceptibility to *P. cubensis*.

The different embodiments of the invention will be described for melon and watermelon herein below and thereafter for the other Cucurbitaceae species.

The plants which comprise mutant aap2a and/or mutant aap2b alleles, and thereby comprise reduced susceptibility to *P. cubensis*, can be grown in methods for fruit production, whereby in one aspect less fungicides treatment is required during the cultivation period. For example, fewer applications of a fungicide effective against *P. cubensis* and/or lower dosages of active ingredient may be used. This saves costs for growers and is better for the environment. The disease management schemes may thus be adapted accordingly, both in protected environments such as greenhouses or tunnels, or in the open field.

Melon Plants and Plant Parts

The S-genes found herein, AAP2A and AAP2B, encode amino acid permease proteins which form a transmembrane protein in the plant and are involved in amino acid transport across the membrane. It was found that leaves of plants containing the aap2a mutant allele in homozygous form accumulated a lower concentration of free amino acids following *P. cubensis* infection compared to leaves of plants containing the wild type AAP2A allele in homozygous form.

The mutant aap2a allele in homozygous form probably limits the flow of nutrients towards the obligate biotrophic pathogen, reducing its fitness and thereby reducing pathogen-induced symptom development (i.e. reducing susceptibility of the plant).

Thus, in one aspect a plant or plant part of the species *Cucumis melo* is provided comprising at least one copy of a mutant allele of a gene named CmAAP2A, said gene encodes a CmAAP2A protein of SEQ ID NO: 1 or a protein comprising at least 90%, 91%, 92%, 93%, 94%, 95%, 96%, 97%, 98% or 99% sequence identity to SEQ ID NO: 1, wherein said mutant allele results in reduced expression or no expression of the CmAAP2A gene or wherein the mutant allele encodes a protein having a decreased function or a loss-of-function compared to the wild type CmAAP2A protein. In one aspect the melon plant or plant part comprises two copies of the mutant allele, i.e. in homozygous form.

As mentioned above, melon was found to contain a second gene, named CmAAP2B, just like CmAAP2A located also on chromosome 8. The second gene encodes a protein with high sequence identity to CmAAP2A (86.7%), it also has the same 2-dimensional structure (with a Aa_trans domain being a large part of the protein) and 3-dimensional structure (as can for example be seen when analysing both proteins in raptorx.uchicago.edu). It is therefore very likely that CmAAP2A and CmAAP2B have the same function in the plant and that mutant CmAAP2B alleles have the same effect on reducing susceptibility to *P. cubensis*.

Thus, in one aspect a plant or plant part of the species *Cucumis melo* is provided comprising at least one copy of a mutant allele of a gene named CmAAP2B, said gene encodes a CmAAP2B protein of SEQ ID NO: 4 or a protein comprising at least 90%, 91%, 92%, 93%, 94%, 95%, 96%, 97%, 98% or 99% sequence identity to SEQ ID NO: 4, wherein said mutant allele results in reduced expression or no expression of the CmAAP2B gene or wherein the mutant allele encodes a protein having a decreased function or a loss-of-function compared to the wild type CmAAP2B protein. In one aspect the melon plant or plant part comprises two copies of the mutant allele, i.e. in homozygous form.

In one aspect a plant or plant part of the species *Cucumis melo* is provided comprising at least one copy of a mutant allele of a gene named CmAAP2A and/or of a mutant allele of a gene named CmAAP2B, wherein said CmAAP2A gene encodes a CmAAP2A protein of SEQ ID NO: 1 or a protein comprising at least 90%, 91%, 92%, 93%, 94%, 95%, 96%, 97%, 98% or 99% sequence identity to SEQ ID NO: 1, and said CmAAP2B gene encodes a CmAAP2B protein of SEQ ID NO: 4 or a protein comprising at least 90%, 91%, 92%, 93%, 94%, 95%, 96%, 97%, 98% or 99% sequence identity to SEQ ID NO: 4, and wherein said mutant cmaap2a allele results in reduced expression or no expression of the CmAAP2A gene or wherein the mutant cmaap2a allele encodes a protein having a decreased function or a loss-of-function compared to the wild type CmAAP2A protein, and wherein said mutant cmaap2b allele results in reduced expression or no expression of the CmAAP2B gene or wherein the mutant cmaap2b allele encodes a protein having a decreased function or a loss-of-function compared to the wild type CmAAP2B protein.

In one aspect the melon plant or plant part comprises one or two copies of the mutant cmaap2a and/or one or two copies of the mutant cmaap2b allele.

Gene expression can be measured as known in the art, e.g. by measuring the mRNA transcript levels by quantitative real-time PCR (qRT-PCR). See for example Berg et al. BMC Plant Biology 2015, 15: 243, page 1-17, see page 15.

A plant may thus either have a mutant cmaap2a or a mutant cmaap2b allele (i.e. a single mutant allele), or both (double mutant). The plant comprising a single mutant cmaap2a allele in homozygous form showed reduced susceptibility to the oomycete *Pseudoperonospora cubensis* compared to the susceptible control plant lacking any of the mutant alleles (i.e. comprising wild type alleles) and the same is expected for a plant comprising a single mutant cmaap2b allele in homozygous form. In a plant comprising a double mutant allele the susceptibility to *P. cubensis* may be even reduced more strongly than in the single mutant plant. This can be tested by combining mutant cmaap2a and mutant cmaap2b alleles in a single plant, either by directly generating double mutants in a single plant (using e.g. CRISPR constructs with multiple single guide RNAs, sgRNAs, targeting both genes) or by crossing plants comprising single mutant alleles with each other and selecting progeny comprising both mutant alleles.

Thus, in a further aspect the mutant cmaap2a and/or cmaap2b allele confers reduced susceptibility to the oomycete *Pseudoperonospora cubensis* at least when the mutant cmaap2a and/or cmaap2b allele is in homozygous form compared to a plant or plant part homozygous for the wild type allele of the CmAAP2A and CmAAP2B gene. The reduced susceptibility can be measured in a disease assay by e.g. assessing the *P. cubensis* induced symptom development, e.g. leaf yellowing/chlorosis and/or sporulation, at one or more time points after inoculation, in a plant line or variety comprising the mutant cmaap2a allele and/or cmaap2b allele in homozygous form, compared to a susceptible control plant line or variety comprising the wild type CmAAP2A allele and wild type CmAAP2B allele in homozygous form when grown under the same conditions. The plant line comprising the mutant cmaap2a allele and/or cmaap2b allele in homozygous would be considered to have reduced susceptibility when the average symptom development, e.g. leaf yellowing/chlorosis and/or average sporulation, is significantly less compared to the average leaf yellowing/chlorosis and/or average sporulation in the susceptible control. See Examples for a suitable disease assay for assessing leaf yellowing/chlorosis in cucumber. The same assay can used in the same way for melon plants. When using the assay in melon, average yellowing is preferably also assessed at 7 dpi. Of course other assays may equally be used, as long as the susceptible control shows the expected symptoms.

An endogenous melon CmAAP2A gene (or an CmAAP2A allele thereof) is a gene (or allele) encoding a (wild type, functional) CmAAP2A protein which comprises at least 90% or more sequence identity to the melon CmAAP2A protein of SEQ ID NO: 1. It comprises an Aa_trans domain as shown in FIG. 1. The presence of an Aa_trans domain can be checked by analysing the amino acid sequence in InterPro, at ebi.ac.uk/interpro/search/sequence-search.

An endogenous melon CmAAP2B gene (or an CmAAP2B allele thereof) is a gene (or allele) encoding a (wild type, functional) CmAAP2B protein which comprises at least 90% or more sequence identity to the melon CmAAP2B protein of SEQ ID NO: 4. It comprises an Aa_trans domain as shown in FIG. 2. The presence of a Aa_trans domain can be checked by analysing the amino acid sequence in InterPro, at ebi.ac.uk/interpro/search/sequence-search.

In the plant or plant part comprising said mutant cmaap2a allele and/or mutant cmaap2b allele, said mutant cmaap2a or cmaap2b allele results in reduced expression or no expression of the (endogenous, wild type) CmAAP2A gene or CmAAP2B gene, respectively, or said mutant cmaap2a or cmaap2b allele encodes a protein having a decreased function or a loss-of-function compared to the wild type CmAAP2A or CmAAP2B protein, respectively, i.e. said mutant allele encodes a mutant cmaap2a protein or cmaap2b protein.

Thus, as a result of the mutation in the endogenous CmAAP2A and/or CmAAP2B allele, there is either less or even no wild type CmAAP2A or CmAAP2B mRNA transcript being produced by the mutant allele (e.g. if the mutation is in a regulatory sequence of the endogenous allele) in the plant cell and plant, or as a result of the mutation a mutant CmAAP2A protein or CmAAP2B protein is produced by the mutant allele, e.g. comprising one or more amino acids replaced, deleted or inserted compared to the functional wild type protein, thereby leading to a reduced function or loss of function of the (mutant) cmaap2a and/or cmaap2b protein. And consequently, at least when the mutant cmaap2a and/or cmaap2b allele is in homozygous form in the genome of the plant, the plant will be at least partially resistant against downy mildew/less susceptible to *P. cubensis* than the plant comprising two functional/wild type CmAAP2A alleles and two functional/wild type CmAAP2B alleles.

No expression of the mutant cmaap2a or cmaap2b allele means that no transcript (mRNA) is being transcribed from the mutant allele, due to e.g. a mutation in the promoter sequence being present. So if the mutant allele is in homozygous form, the wild type mRNA, encoding the functional protein will not be present in plant tissue in which it is otherwise present in the susceptible control (comprising the wild type alleles), such as for example roots, stems, hypocotyl, cotyledon or leaf. An allele having no expression may also be referred to as a knock-out allele herein.

Reduced (or decreased) expression of the mutant cmaap2a allele or of the mutant cmaap2b allele means for example that only 50%, or less, of the amount of transcript (mRNA) is transcribed from the mutant allele compared to the wild type allele, or only equal to or less than 40%, 30%, 20%, 10%, or 5% of the amount of transcript (mRNA) is transcribed from the mutant allele compared to the wild type allele. In other words, when the mutant allele is in homozygous form, the wild type mRNA, encoding the functional protein will be present in plant tissue in which it is otherwise present, such as for example leaves, roots, hypocotyl, cotyeldons or stems, but at a significantly lower amount than in a plant which is homozygous for the wild type allele. This will result in significantly less functional wild type protein being present, which in turn results in reduced susceptibility of the plant. An allele having reduced expression may also be referred to as a knock-down allele herein.

The decrease in the expression of cmaap2a or cmaap2b allele can, for example, be determined by measuring the quantity of RNA transcripts (e.g. mRNA), e.g. by qRT-PCR. Similarly, the decrease in the amount of CmAAP2A or CmAAP2B protein, can, for example, be determined by immunological methods such as Western blot analysis, ELISA (Enzyme Linked Immuno Sorbent Assay) or RIA (Radio Immune Assay). Here, a decrease preferably means a reduction in the amount of CmAAP2A proteins or CmAAP2B protein by at least 50%, in particular by at least 70%, or by at least 85% and particularly by at least 95%.

In another embodiment the melon plant or plant part comprises a mutant cmaap2a allele, wherein the protein encoded by the mutant cmaap2a allele comprising one or more amino acids replaced, inserted or deleted compared to the CmAAP2A wild type protein of SEQ ID NO: 1 (or a functional variant thereof comprising at least 90% sequence identity to SEQ ID NO: 1), especially one or more amino acids replaced, inserted and/or deleted in the conserved Amino Acid Transporter Domain at amino acid 20 to 453 of SEQ ID NO: 1 or in an Amino Acid Transporter Domain comprising at least 95%, 96%, 97%, 98% or 99% sequence identity to amino acid 20 to 453 of SEQ ID NO: 1. Such a protein can have a reduced activity or no activity in vivo.

In another embodiment the melon plant or plant part comprises a mutant cmaap2b allele, wherein the protein encoded by the mutant cmaap2b allele comprising one or more amino acids replaced, inserted or deleted compared to the CmAAP2B wild type protein of SEQ ID NO: 4 (or a functional variant thereof comprising at least 90% sequence identity to SEQ ID NO: 4), especially one or more amino acids replaced, inserted and/or deleted in the conserved Amino Acid Transporter Domain at amino acid 20 to 453 of SEQ ID NO: 4 or in an Amino Acid Transporter Domain comprising at least 95%, 96%, 97%, 98% or 99% sequence identity to amino acid 20 to 453 of SEQ ID NO: 4. Such a protein can have a reduced activity or no activity in vivo.

In one embodiment the plant or plant part comprises both of the above mutant alleles (double mutant).

In one aspect, the melon plant or plant part comprises a mutant cmaap2a allele and/or a mutant cmaap2b allele, wherein the mutant cmaap2a allele encodes a protein that is truncated compared to the wild type CmAAP2A protein and/or the mutant cmaap2b allele encodes a protein that is truncated compared to the wild type CmAAP2B protein. The truncated protein may comprise additional amino acids, for example a frame shift mutation may result in the truncated protein comprising an amino acid sequence which is different from the amino acid sequence of the wild type protein. A truncated protein can have a reduced activity or even no activity in vivo, especially when all or part of the Aa_trans domain is missing and/or is replaced by different amino acids. Thus in one aspect the mutant cmaap2a allele encodes a protein that is truncated compared to the wild type CmAAP2A protein and/or the mutant cmaap2b allele encodes a protein that is truncated compared to the wild type CmAAP2B protein, wherein at least one, two, three, four, 5, 6, 7, 8, 9, 10, 15, 20, 30, 40, 50 or more amino acids of the Aa_trans domain are missing or are replaced by different amino acids compared to the wild type protein. In one aspect at least 13, 14, 15, 20, 30, 40, 50 or more amino acids of the C-terminal end of the CmAAP2A or CmAAP2B protein are missing or are replaced by one or more different amino acids compared to the wild type protein. One example of a truncated protein is the CmAAP2A of SEQ ID NO: 1 comprising a W25STOP mutation. As shown in the Examples, when this orthologous mutant allele is in homozygous form in cucumber, it enhances resistance to *P. cubensis*.

The 2-dimensional analysis showed that a large part of the CmAAP2A protein and CmAAP2B protein consists of the Aa_trans domain. 3-dimensional analysis predicts that the CmAAP2A protein consists of 67% helix structure and 32% loop structures (coils) and the CmAAP2B protein consists of 66% helix structure and 33% looped structures (coils). This means that any amino acid insertion, deletion or replacement, especially of one or more amino acids in the Aa_trans domain, will likely change the 3-dimensional structure of the protein and reduce its in vivo function or even abolish its in vivo function. For example, a mutation which results in a change of a codon into a STOP codon, will result in a truncated protein.

In one aspect the melon plant comprises a mutant cmaap2a allele (in homozygous or heterozygous form), wherein the encoded protein lacks the 95 C-terminal amino acids of SEQ ID NO: 1, or of a protein comprising at least 90% sequence identity to SEQ ID NO: 1. For example a mutation in the codon encoding amino acid number 372 (W, Tryptophan) to a stop codon, leads to a truncation of the CmAAP2A protein, whereby the protein comprises amino acids 1 to 371 of SEQ ID NO: 1 and lacks amino acids 372 to 466 of SEQ ID NO: 1, i.e. the 95 C-terminal amino acids are missing. As these 95 C-terminal amino acids comprise 82 amino acids of the AA_trans domain, the protein has reduced function or more likely even loss-of-function in vivo. The melon plant comprising this mutant allele in homozygous form has a reduced susceptibility to *P. cubensis*. This mutant allele can be induced, or it can also be a natural mutant allele, introgressed into cultivated *C. melo*.

In one aspect the mutant allele is a natural mutant allele obtained from an accession of a *C. melo* var. *momordica*. The accession in which this particular natural mutant allele was found has an average TSS (total soluble solids) of 5%-8%, as well as other non-desirable characteristics. This accession can, therefore, be used as a donor to backcross the mutant cmaap2a allele into cultivated *C. melo*, e.g. into one of *C. melo* var. cantalupensis, *C. melo* var. inodorous or *C. melo* var. reticulatus. Preferably the mutant cmaap2a allele is backcrossed into cultivated melon having good agronomic characteristics, such as a TSS of at least 10%, 11%, 12%, 13%, 14%, 15%, 16%, 17%, 18% or more.

A mutant cmaap2a allele encoding a truncated CmAAP2A protein may, thus be an allele which encodes a protein that lacks at least 13, 14, 15, 20, 30, 40, 50, 60, 70, 80, 90, 95, 100, 120, 130, 140, 150, 160, 170, 180, 190, 200, 250, 300, 350, 400 or even more of the C-terminal amino acids compared to the wild type CmAAP2A protein of SEQ ID NO: 1, or of a variant comprising at least 90%, 91%, 92%, 93%, 94%, 95%, 96%, 97%, 98% or 99% sequence identity to SEQ ID NO: 1.

A mutant cmaap2b allele encoding a truncated CmAAP2B protein may, thus be an allele which encodes a protein that lacks at least 13, 14, 15, 20, 30, 40, 50, 60, 70, 80, 90, 100, 120, 130, 140, 150, 160, 170, 180, 190, 200, 250, 300, 350, 400 or even more of the C-terminal amino acids compared to the wild type CmAAP2B protein of SEQ ID NO: 4, or of a variant comprising at least 90%, 91%, 92%, 93%, 94%, 95%, 96%, 97%, 98% or 99% sequence identity to SEQ ID NO: 4.

Thus in one aspect the mutant allele results in a truncated CmAAP2A protein or a truncated CmAAP2B protein being produced, which truncated protein has decreased function or loss-of-function. A truncation may for example result in the loss of the C-terminal end (carboxyl terminal end) of the protein, whereby part or all of the Aa_trans domain is absent. For example only the N-terminal part (amino terminal part) of the protein may still be present. Mutant alleles which express a truncated CmAAP2A protein or a truncated CmAAP2B protein can be induced whereby, for example, a codon in one of the exons is changed into a premature stop codon or splice-site mutations or frame-shift mutations can also lead to premature stop codons and truncated proteins.

In another aspect the mutant allele results in a mutant CmAAP2A or CmAAP2B protein, which comprises one or more amino acids inserted, replaced and/or deleted compared to the wild type protein. As mentioned, especially insertion, replacement and/or deletion of one or more amino acids in the Aa_trans domain will result in a mutant protein that has decreased function or loss of function, and will, at least in homozygous form in the melon plant, reduce susceptibility to *P. cubensis*.

Whether the insertion, replacement and/or deletion of one or more amino acids, or a truncation or a mutant allele not expressed or having reduced expression, as described elsewhere herein, actually results in a reduced susceptibility in vivo can be tested by carrying out a disease assay for a plant comprising the mutant allele (or double mutant) in homozygous form.

Optionally the increase in free amino acids following *P. cubensis* infection can be compared between the plant comprising the mutant cmaap2a and/or cmaap2b allele and the susceptible control comprising the wild type alleles (WT) as described in the Examples. A reduced increase in free amino acids, especially in Ala, Gly, Val, Leu, Ile, Thr, Ser, Pro and/or Gln compared to the increase in the susceptible control (comprising functional wild type CmAAP2A and CmAAP2B alleles) may indicate, in one aspect, that the mutant allele has reduced function or a loss of function in vivo.

In yet another aspect the mutant allele results in reduced expression or no expression of the allele and thus reduced amounts or no protein of the wild type CmAAP2A or CmAAP2B protein being produced in the plant or plant part. For example, the promoter or another regulatory element of the CmAAP2A or CmAAP2B allele may be comprise one or more nucleotides inserted, deleted and/or replaced.

Thus, a mutant allele of a CmAAP2A protein-encoding gene and/or CmAAP2B protein-encoding gene causes a plant to have reduced susceptibility to *P. cubensis*, at least when the plant is homozygous for the mutant allele. Concerning the embodiments of the invention, the mutation in the mutant allele of a CmAAP2A protein-encoding gene or CmAAP2B protein encoding gene (i.e. in the mutant cmaap2a allele and/or cmaap2b allele) can be any mutation, including one or more deletions, truncations, insertions, point mutations, nonsense mutations, missense or non-synonymous mutations, splice-site mutations, frame shift mutations and/or mutations in regulatory sequences (for example in the promoter sequence). In one aspect the mutation in the mutant cmaap2a allele and/or cmaap2b allele is a point mutation. The mutation can occur in a DNA sequence comprising the coding sequence of a CmAAP2A protein-encoding gene or CmAAP2B protein-encoding gene, or in a RNA sequence encoding a CmAAP2A protein or CmAAP2B protein, or it can occur in the amino acid molecule of the CmAAP2A or CmAAP2B protein.

Concerning a DNA sequence of CmAAP2A protein-encoding gene or CmAAP2B protein-encoding gene, the mutation can occur in the coding sequence (cds, composed of the exons) or it can occur in non-coding sequences like 5'- and 3'-untranslated regions, introns, promoters, enhancers etc. In respect to RNA encoding a CmAAP2A protein or CmAAP2B protein, the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted or deleted in the conserved Aa_trans domain. For example, truncation of the protein to cause deletion of the Aa_trans domain, or part thereof, will result in a loss of function or decrease of function of the protein.

A further embodiment of the invention therefore concerns melon plant cells or plants according to the invention comprising a mutant allele of a CmAAP2A protein-encoding gene and/or of a CmAAP2B protein-encoding gene, characterized in that the mutant cmaap2a allele and/or mutant cmaap2b allele comprises or effects one or more of the mutations selected from the group consisting of a) a deletion, truncation, insertion, point mutation, nonsense mutation, missense or non-synonymous mutation, splice-site mutation, frame shift mutation in the genomic sequence;
b) a mutation in one or more regulatory sequences;
c) a deletion, truncation, insertion, point mutation, nonsense mutation, missense or non-synonymous mutation, splice-site mutation, frame shift mutation in the coding sequence;
d) a deletion, truncation, insertion, point mutation, nonsense mutation, missense or non-synonymous mutation, splice-site mutation, frame shift mutation in the pre-mRNA or mRNA; and/or
e) a deletion, truncation, insertion or replacement of one or more amino acids in the CmAAP2A or CmAAP2B protein.

A different embodiment of the invention concerns melon plant cells, plant parts or plants comprising or synthesising an mRNA encoding a CmAAP2A protein and/or CmAAP2B protein, wherein the mRNA encoding a CmAAP2A protein or CmAAP2B protein has one or more mutations selected from the group consisting of a) a deletion mutation;
b) a missense or non-synonymous mutation;
c) a frame shift mutation; and/or
d) a non-sense mutation.

In another embodiment of the invention, plant cells or plants according to the invention comprise or synthesise an mRNA encoding a CmAAP2A protein and/or CmAAP2B protein having one or more mutations, wherein the mRNA is transcribed from a mutant allele of a CmAAP2A protein-encoding gene and/or from a mutant allele of a CmAAP2B protein-encoding gene. Comprised by these embodiments of the invention are plant cells, plant parts or plants according to the invention comprising or synthesising an mRNA transcribed from a mutant allele of a CmAAP2A protein-encoding gene and/or CmAAP2B protein encoding gene, characterized in that the mRNA comprises a deletion mutation and/or a missense or non-synonymous mutation and/or a frame shift mutation and/or a non-sense mutation, compared to the corresponding (DNA) coding sequence of the mutant allele of the CmAAP2A or CmAAP2B protein-encoding gene from which the mRNA is transcribed. Thus, in one aspect any mutation which affects pre-mRNA splicing is encompassed, i.e. which modifies the normal pre-mRNA splicing process, thereby leading to a different mRNA molecule.

An "mRNA coding sequence" shall have the common meaning herein. An mRNA coding sequence corresponds to the respective DNA coding sequence of a gene/allele apart from that thymine (T) is replaced by uracil (U).

In one aspect the melon plant or plant part is homozygous for a mutant cmaap2a allele and/or for a mutant cmaap2b allele described herein. Because both the CmAAP2A gene and the CmAAP2B gene are deemed to be recessive, the reduction in susceptibility is seen phenotypically when the plant is homozygous for one or both of the mutant alleles, although it is not excluded that an effect may also be seen when the plant is heterozygous for one or both mutant alleles.

In one aspect the mutant cmaap2a and/or cmaap2b allele is an induced mutant allele, while in a different aspect the mutant cmaap2a and/or cmaap2b allele is a "natural mutant allele" introgressed into cultivated melon by e.g. backcrossing.

Mutant alleles can be generated by methods known in the art, such as chemical mutagenesis (e.g. EMS treatment), radiation mutagenesis (UV, gamma rays etc.), targeted mutagenesis, such as Crispr/Cas9 or TALENS.

Suitable chemical mutagens include ethyl methanesulfonate (EMS), methylmethane sulfonate (MMS), N-ethyl-N-nitrosurea (ENU), trimethylamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitrosoguanidine (MNNG), nitrosoguanidine, 2-aminopurine, 7,12-dimethylbenz(a)anthracene (DMBA), ethylene oxide, hexamethylphosphoramide, bisulfan, diepoxyalkanes, diepoxyoctrane (DEO), diepoxybutane (DEB), 2-methoxy-6-choloro9[3-ethyl-2-chloro-ethyl]aminopropylamine]acridine dihydrochloride (ICR-170), and formaldehyde. Suitable radiation is UV radiation or radioactive radiation.

Biotechnological methods for introducing mutations into a desired gene/allele of a plant cell or plant are known in the art. Therefore, mutant alleles of a CmAAP2A and/or CmAAP2B protein-encoding gene can be produced in plant cells or plants by using these methods. Examples for such technologies are in particular mutagenesis techniques or enzymes which induce double stranded DNA breaks (double stranded DNA break inducing enzyme (DSBI)) in the genome of plants. Known and practised technologies are rare-cleaving endonucleases and custom-tailored rare-cleaving endonucleases including but not limited to homing endonucleases, also called meganucleases, transcription activator-like effectors fused to the catalytic domain of a nuclease (TALENs) and so-called CRISPR systems. CRISPR systems is used broadly herein, and does not only encompass the use of the Cas9 nuclease (Crispr/Cas9 system), but also other Crispr systems e.g. using other nucleases, such as Cpf1. These techniques can also be referred to as targeted genome editing techniques or gene editing techniques or targeted mutagenesis techniques.

Thus, technologies such as mutagenesis or targeted genome editing techniques are eligible for introducing a mutation into genes in plant cells or plants. Therefore, plant cells and plants according to the invention having a mutant allele of a CmAAP2A and/or CmAAP2B protein-encoding gene, wherein the mutation into the mutant allele was introduced by genome editing techniques, e.g. using rare-cleaving endonucleases or custom-tailored rare-cleaving endonucleases, are also an embodiment of the invention. Concerning custom-tailored rare-cleaving endonucleases the mutation in the mutant allele of CmAAP2A and/or CmAAP2B protein has preferably been introduced by a meganuclease, a TALENs or a CRISPR system.

In melon the EU Funded Horizon 2020 project "Implementation of CRISPR/Cas9 technology in melon to edit fruit ripening and CMV resistant genes" (MeloCrisp, Grant agreement ID: 793090) uses CRISPR/Cas9 to modify endogenous genes in melon. Also other groups are using Crispr/Cas9 in melon, e.g. world wide web at tss.gov.tw/en/ describe a project on 'Development of potyvirus resistance in melon using CRISPR/Cas9 technology'. Use of the Crispr system in melon is therefore known to the skilled person. A general review on the use of Crispr Cas9 in plant breeding is provided by Cao et al. 2016 (International Journal of Genomics, Volume 2016, p 1-10, Article ID 5078796).

Thus, in one aspect the mutant cmaap2a and/or cmaap2b alleles are induced mutants, e.g. induced in a breeding line, an inbred line or variety of cultivated melon or in one aspect the mutant alleles are induced in wild melon or wild relatives of melon (and the induced mutant alleles can then be backcrossed into cultivated melon). In one aspect the mutant alleles are generated by mutagenesis (e.g. chemical or radiation mutagenesis) or by targeted mutagenesis, especially using the CRISPR system (e.g. Crispr/Cas9 or Crispr/CpfCpf1 or other nucleases). In one aspect the cultivated melon plant comprising the mutant cmaap2a and/or cmaap2b alleles is not a transgenic plant, i.e. non transgenic progeny are selected which do not comprise e.g. the CRISPR construct.

The cultivated melon may be of any type. Cultivated *Cucumis melo*, can be classified into: *C. melo* var. cantalupensis, *C. melo* var. inodorous and *C. melo* var. reticulatus. *C. melo* var. cantalupensis are also referred to as Cantaloupes and are primarily round in shape with prominent ribs and almost no netting. Most have orange, sweet flesh and they are usually very fragrant. In contrast to the European cantaloupe, the North American ‘Cantaloupe’ is not of this type, but belongs to the true muskmelons. *C. melo* var. inodorous (or winter melons) can be subdivided into different types, such as Honeydew melon, Piel de Sapo, Sugar melon, Japanese melon, etc. *C. melo* var. reticulatus is the true muskmelon, with reticulated skin (netted) and includes Galia melons, Sharlyn melons and the North American cantaloupe.

Thus, in one aspect the cultivated melon plants and plant cells belong to one of the following species: *C. melo* var. cantalupensis, *C. melo* var. inodorous or *C. melo* var. reticulatus.

Preferably it has good agronomic and good fruit quality characteristics, such as e.g. large average fruit size (at least 500 g, 600 g, 700 g, 800 g, 900 g, 1000 g or more), high average brix of the fruits (e.g. an average refractometer % total soluble solids of at least 10%, 12%, 14%, 16%, 18% or more), many fruits being produced per plant, firm fruit flesh, etc.

As mentioned, mutant alleles can also evolve naturally in populations of wild melon or wild relatives of melon, such as such as *Cucumis melo* var. *momordica*, or *Cucumis melo* ssp. agrestis. In one aspect the mutant cmaap2a and/or cmaap2b alleles are natural mutant alleles, which have been introgressed into cultivated melon. The wild type allele found in cultivated melon on chromosome 8 is then replaced with the natural mutant allele, i.e. by meitotic recombination between homologous chromosomes. Wild melon accessions can be screened for the presence of such natural mutant alleles, and backcrossing to cultivated melon can be used to introgress the natural mutant allele into the cultivated melon genome. Such methods and plants produced thereby, comprising one or more introgressions, are encompassed herein.

Thus in one aspect a plant or plant part of the species *Cucumis melo* is provided, comprising an introgression fragment from a wild melon or wild relative of melon on chromosome 8, said introgression fragment comprises a mutant allele of a gene named CmAAP2A, said gene encodes a CmAAP2A protein of SEQ ID NO: 1 or a protein comprising at least 90%, 91%, 92%, 93%, 94% or 95% sequence identity to SEQ ID NO: 1, and/or a mutant allele of a gene named CmAAP2B, said gene encoding a CmAAP2B protein of SEQ ID NO: 4 or a protein comprising at least 90%, 91%, 92%, 93%, 94% or 95% sequence identity to SEQ ID NO: 4, wherein said mutant cmaap2a and/or cmaap2b allele results in reduced expression or no expression of the mutant allele or encodes a protein having a decreased function or a loss-of-function compared to the wild type protein.

In one aspect the introgression fragment comprises a natural mutant allele. In another aspect the introgression fragment comprises an induced mutant allele.

In one aspect wild melon plants, or wild relatives of melon are screened for the presence of a natural mutant cmaap2a or cmaap2b allele. This can be done by e.g. analysing (directly or indirectly) the genomic DNA, mRNA (or cDNA) or protein of the CmAAP2A or CmAAP2B gene, using e.g. PCR methods or other molecular methods known in the art, such as sequencing, etc. whereby the presence of a mutant cmaap2a or cmaap2b allele can be determined. The wild melon plants or wild relatives of melon may be CGN accessions, PI accessions (Plant Introductions), or accessions from various seed bank collections. Once an accession is identified to comprise a mutant cmaap2a or cmaap2b allele, the accession can be crossed to cultivated melon, and the mutant allele can be introgressed into the genome of cultivated melon by e.g. backcrossing. The cultivated melon introgression line is preferably selfed one or more times to ensure the mutant allele is in homozygous form and the line can then be tested for reduced susceptibility to *P. cubensis* compared to e.g. the original cultivated melon (e.g. the recurrent parent) comprising the wild type, functional CmAAP2A and CmAAP2B alleles in homozygous form.

Also encompassed herein is a method for identifying a natural mutant cmaap2a and/or a natural mutant cmaap2b allele. The method involves determining whether a wild melon or wild relative of melon comprises a natural mutant allele and optionally transferring the natural mutant allele into cultivated melon by traditional breeding techniques. Wild plant accessions are generally very heterogenous and also may comprise various other genes which affect downy mildew resistance. The effect of the mutant allele on the susceptibility of the plant will be difficult to assess in the wild accession and the mutant allele is preferably first transferred into a breeding line, preferably a breeding line which is susceptible to downy mildew. In one embodiment therefore a method for transferring a natural mutant cmaap2a and/or a natural mutant cmaap2b allele from a wild melon plant into a cultivated melon plant is provided, comprising a) identifying or providing a wild melon comprising a natural mutant cmaap2a and/or cmaap2b allele
b) crossing the mutant allele(s) into cultivated melon, preferably a cultivated melon line which is susceptible to *P. cubensis*, and
c) determining the effect of the mutant allele on the susceptibility to *P. cubensis.*

The same can of course be done for induced mutant alleles, which may be induced in wild melon, whereby in step a) one provides or identifies a wild melon comprising an induced mutant allele. The method may then be preceded by a step wherein mutations are induced.

The cultivated melon plant described herein, comprising either an induced mutant or a natural mutant cmaap2a and/or cmaap2b allele in its genome preferably comprises either or both mutant alleles in homozygous form, as the reduced susceptibility against *P. cubensis* is at least seen when the allele is in homozygous form. Plants comprising either or both mutant alleles in heterozygous form are also encompassed herein.

The cultivated melon plant comprising a mutant cmaap2a and/or a mutant cmaap2b allele according to the invention may be of any type, e.g. it may be of one of the following species: *C. melo* var. cantalupensis, *C. melo* var. inodorous or *C. melo* var. reticulatus.

The cultivated melon plant according to the invention may be an inbred line, an OP (open pollinated variety) or an F1 hybrid. In one aspect the F1 hybrid comprises a mutant cmaap2a and/or cmaap2b allele in homozygous form.

The cultivated melon plant preferably has good agronomic and good fruit quality characteristics. The cultivated melon plant is in one aspect uniform, both genetically and phenotypically. Especially fruit characteristics are uniform, e.g. regarding shape, color, fruit flesh color, brix or TSS (total soluble solids), flavour, etc. Likewise seed characteristics (i.e. characteristics of the seeds from which the plant is grown) are uniform, e.g. seed size, seed color, etc. In one aspect the melon fruits (of the plant comprising the induced mutant cmaap2a and/or cmaap2b allele or natural cmaap2a and/or cmaap2b mutant allele) have an average TSS at maturity or harvest stage of at least 10%, 11%, 12%, 13%, 14%, 15%, 16%, 17%, 18%. The average % TSS (or brix) can be measured as known in the art, e.g. using a digital hand refractometer and measuring the TSS of several fruits of a line or variety. See for example Burger et al. 2003, J American Soc Hort Science 128(4): 537-540 on page 538 at Measurement of TSS.

Also a seed is provided from which a plant or plant part according to the invention can be grown.

Further a melon fruit produced by a plant according to the invention is provided, wherein the fruit comprises the mutant cmaap2a and/or cmaap2b allele, preferably in homozygous form.

Likewise plant parts of a plant according to the invention are provided, wherein the plant part is a cell, a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther. The plant part comprises in its genome a mutant cmaap2a and/or a mutant cmaap2b allele of the invention, preferably in homozygous form. In one aspect the cell is a non-propagating or a non-regenerable cell. In one aspect the non-propagating or non-regenerable cell is part of a tissue or organ of the plant. In a different aspect the non-propagating or non-regenerable cell is in a cell culture or tissue culture.

Also a cell culture or a tissue culture of cells or tissues comprising in its genome a mutant cmaap2a and/or a mutant cmaap2b allele of the invention is encompassed herein. Further a plant regenerated from such a cell or tissue culture is encompassed.

Further a vegetatively propagated plant propagated from a plant part according to the invention is provided.

Also a food or feed product comprising cells according to the invention are provided, such as parts of melon fruits.

In one embodiment a method of melon fruit production is provided, said method comprising growing a plant according to the invention, comprising a mutant cmaap2a and/or cmaap2b allele, preferably in homozygous form, said method optionally comprising a reduced treatment with fungicides compared to a susceptible control plant, e.g. a plant comprising a wild type CmAAP2A allele and a wild type CmAAP2B allele in homozygous form, and optionally harvesting the fruits produced by said plants. As the plant is less susceptible to *P. cubensis*, less fungicide treatment (lower amounts and/or less frequent applications of fungicides) is needed.

*P. cubensis* infects melon plants in both the field and the greenhouse, therefore in the above method plants of the invention are grown either in the field or in greenhouses.

The pathogen has a high potential to become resistant to fungicides, it was for example the first oomycete with documented resistance to metalaxyl and reduced sensitivity to mancozeb. It has also been described to have developed resistance to strobulurin fungicides. Less fungicide treatment will reduce the risk of resistance developing.

As mentioned previously, mutant cmaap2a and/or cmaap2b alleles can be induced, i.e. the can be generated by mutating the endogenous CmAAP2A and/or CmAAP2B allele in cultivated melon seeds or plants or plant parts (or optionally in wild plants) and/or by selecting induced mutants e.g. tissue culture induced mutants or TILLING mutants.

Therefore, methods for producing and/or selecting plants having mutant cmaap2a and/or cmaap2b alleles, resulting in a knock-down or knock-out of gene expression and consequently less or no wild type protein being produced, or mutant alleles encoding mutant proteins having a decreased function or loss-of-function compared to the wild type protein are encompassed herein. To generate such mutant alleles conventional mutagenic agents, like chemicals or high energy radiation (e.g. x-rays, neutron radiation, gamma radiation or UV radiation) may be used. It is also possible to generate mutant alleles by means of biotechnology methods as described above (e.g. targeted gene editing technology).

In one aspect the invention provides a method for generating and/or identifying a melon plant comprising a mutant allele of a gene named CmAAP2A, said gene encodes a CmAAP2A protein of SEQ ID NO: 1 or a protein comprising at least 90%, 91%, 92%, 93%, 94% or 95% sequence identity to SEQ ID NO: 1, comprising identifying or selecting a plant in a mutant melon population, or progeny thereof obtained by selfing, comprising a mutant cmaap2a allele, or generating a mutant plant comprising a mutant cmaap2a allele using a targeted genome editing technique, such as a Crispr system (e.g. Crispr/Cas9).

In another aspect the invention provides a method for generating a melon plant comprising a mutant allele of a gene named CmAAP2B, said gene encodes a CmAAP2B protein of SEQ ID NO: 4 or a protein comprising at least 90%, 91%, 92%, 93%, 94% or 95% sequence identity to SEQ ID NO: 4, comprising identifying or selecting a plant in a mutant melon population, or progeny thereof obtained by selfing, comprising a mutant cmaap2b allele, or generating a melon plant comprising a mutant cmaap2b allele using a targeted genome editing technique, such as a Crispr system (e.g. Crispr/Cas9).

A 'mutant melon population' or 'population of mutant melon plants' refers to a plurality of melon seeds or plants or plant parts which have been treated with a conventional mutagenic agents, like chemicals or high energy radiation (e.g. x-rays, neutron radiation, gamma radiation or UV radiation) or progeny thereof obtained by selfing, to ensure that mutations are in homozygous form. These can be plants or seeds or plant parts of a cultivated melon breeding line, variety, inbred line or any plurality of cultivated melon plants or seeds. Alternatively these may be wild melon plants or wild relatives of melon.

Melon plants according to the invention, comprising reduced susceptibility to *P. cubensis*, can be produced by introducing one or more mutations into an allele of a CmAAP2A protein-encoding gene and/or into an allele of a CmAAP2B protein-encoding gene.

A further embodiment of the present invention, therefore, concerns a method for production of a melon plant comprising the steps of a) providing a population of mutant melon plants,
b) optionally selecting a plant which is less susceptible to *P. cubensis* than a non-mutated plant,
c) determining if a plant of the mutant population of a) or selected under b) has a mutation in an allele of a CmAAP2A protein-encoding gene and/or in an allele of a CmAAP2B protein-encoding gene, optionally
d) growing/cultivating the plants obtained under c).

In one aspect is a method for production of a melon plant comprising the steps of a) introducing mutations in a population of melon plants (and optionally selfing the plants),
b) optionally selecting a plant which is less susceptible to *P. cubensis* than a non-mutated plant,
c) determining if the plant selected under b) has a mutation in an allele of a CmAAP2A protein-encoding gene and/or in an allele of a CmAAP2B protein-encoding gene and selecting a plant comprising such a mutation, and optionally
d) growing/cultivating the plants obtained under c).

However, in one aspect the order of the steps can also be different, comprising:

a) providing a population of mutant melon plants,
b) determining if a plant of the mutant population of a) has a mutation in an allele of a CmAAP2A protein-encoding gene and/or in an allele of a CmAAP2B protein-encoding gene, optionally
c) selecting a plant comprising a mutation in an allele of a CmAAP2A protein-encoding gene and/or in an allele of a CmAAP2B protein-encoding gene, and optionally
d) selfing the plant of b) or c) to generate a plant comprising the mutant allele in homozygous form, and optionally
e) determining if the plant of step c) or d) is less susceptible to *P. cubensis* than a non-mutated plant.

Or the steps may comprise:

a) introducing mutations in a population of melon plants (and optionally selfing the plants)
b) determining if a plant of a) has a mutation in an allele of a CmAAP2A protein-encoding gene and/or in an allele of a CmAAP2B protein-encoding gene and optionally
c) selecting a plant comprising such a mutation, and optionally
d) selfing the plant of b) or c) to generate a plant comprising the mutant allele in homozygous form, and optionally
e) determining if the plant of step c) or d) is less susceptible to *P. cubensis* than the non-mutated plant.

A non-mutated plant may be e.g. a susceptible control plant, such as a plant comprising wild type, functional CmAAP2A and CmAAP2B alleles in homozygous form.

Optionally, the above methods comprises selecting a plant comprising at least one copy of a mutant allele of a gene encoding a CmAAP2A or CmAAP2B protein. The selected plants are also an embodiment.

Chemical substances, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide (NaN3) is described, for example, in Jauhar and Siddiq (1999, Indian Journal of Genetics, 59 (1), 23-28), in Rao (1977, Cytologica 42, 443-450), Gupta and Sharma (1990, Oryza 27, 217-219) and Satoh and Omura (1981, Japanese Journal of Breeding 31 (3), 316-326). The production of wheat mutants using NaN3 or maleic hydrazide is described in Arora et al. (1992, Annals of Biology 8 (1), 65-69). An overview of the production of wheat mutants using different types of energy-rich radiation and chemical substances is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutations in triticale. The use of MMS (methyl methane sulphonic acid) and gamma radiation for the production of millet mutants is described in Shashidhara et al. (1990, Journal of Maharashtra Agricultural Universities 15 (1), 20-23).

All these methods are basically suitable in the method for production of a plant according to the invention for producing mutant alleles in genes encoding a CmAAP2A or CmAAP2B protein.

The plants generated and/or selected by these methods are also an embodiment of the invention. These plants can be used to make breeding lines and varieties comprising the mutant alleles.

Selecting plants having reduced susceptibility to *P. cubensis* can be done in a disease assay as e.g. described in the Examples. As the phenotype is at least seen in homozygous condition, selfing of the plant or the population of mutagenized plants is preferred before phenotyping. Mutations in the appropriate alleles, in particular in alleles of CmAAP2A protein-encoding gene or CmAAP2B protein encoding gene, can be found with the help of methods known to the person skilled in the art. In particular, analyses based on hybridisations with probes (Southern Blot), amplification by means of polymerase chain reaction (PCR), sequencing of related genomic sequences and the search for individual nucleotide exchanges can be used for this purpose. Methods, which allow several plants to be investigated for mutations in certain genes in a short time, are particularly suitable. Such a method, so-called TILLING (Targeting Induced Local Lesions IN Genomes), has been described by McCallum et al. (2000, Plant Physiology 123, 439-442).

Other methods for identifying if a plant cell or plant comprises a mutant allele of a CmAAP2A or CmAAP2B protein-encoding gene comprise sequencing of the respective alleles and SNP marker analyses with methods common in the art and e.g. discussed in Thomson (2014, Plant Breeding and Biotechnology 2, 195-212). Also analysis of CmAAP2A or CmAAP2B mRNA being expressed, and optionally quantified, can be used, e.g. to identify mutants having reduced or no gene expression.

These methods are basically suitable for identifying plant cells according to the invention and plants according to the invention having a mutant allele of a CmAAP2A or CmAAP2B protein-encoding gene.

In one aspect, a method for identifying a melon plant or plant part or cell comprising in its genome at least one copy of a mutant allele of CmAAP2A and/or CmAAP2B gene is provided, said method comprising determining whether the plant comprises in its genome at least one mutant cmaap2a allele and/or cmaap2b allele.

The melon plant or plant part may be a cultivated plant or a wild melon plant or wild relative of melon.

This method may involve analysing (directly or indirectly) the gene expression of the cmaap2a allele and/or cmaap2b allele, and/or the genomic nucleotide sequence of the cmaap2a allele and/or cmaap2b allele, or the mRNA nucleotide sequence of the cmaap2a allele and/or cmaap2b allele, or the protein sequence of the CmAAP2A or CmAAP2B protein, or the protein amounts of the CmAAP2A or CmAAP2B protein of the plant or plant part or plant cell, to determine if the gene expression is knocked down or knocked out compared to the wild type plant or plant part or plant cell, or if the encoded protein comprises one or more amino acid insertions, deletions or replacements compared to the wild type CmAAP2A or CmAAP2B protein.

One method for analysing the presence of a mutant cmaap2a allele and/or cmaap2b allele, is for example to assay the presence of a Single Nucleotide Polymorphism (SNP) between the genomic sequence of the mutant cmaap2a allele and/or cmaap2b allele and the wild type CmAAP2A and/or CmAAP2B allele, by, for example, designing primers for the SNP and genotyping plants or plant parts for the genotype of that particular SNP. For example a KASP assay can be used for detecting a SNP and thereby the mutant allele. Likewise primers can be designed for allele specific DNA amplification, e.g. distinguishing a wild type allele from a mutant allele. Such PCR primers can be designed based on the differences between the wild type and the mutant allele. So if the mutant allele comprises a deletion of one or more nucleotides, e.g. in a coding sequence, the primers can be designed to differentiate between the presence of the mutant allele and the wild type allele. The skilled person can easily develop a molecular assay to detect a mutant allele. So one aspect of the invention comprises a method for determining whether a melon plant, plant part or plant cell comprises one or more copies of a mutant cmaap2a allele and/or cmaap2b allele by a method selected from analysing one or more nucleotides of the genomic cmaap2a allele and/or cmaap2b allele, analysing the mRNA (or cDNA) expressed by the cmaap2a allele and/or cmaap2b allele or analysing the CmAAP2A or CmAAP2B protein amount and/or amino acid sequence (using e.g, antibody based detection).

Thus, a method for determining whether a melon plant or plant part comprises at least one copy of a mutant allele of a gene named CmAAP2A is provided, said gene encodes a CmAAP2A protein of SEQ ID NO: 1 or a protein comprising at least 90%, 91%, 92%, 93%, 94% or 95% sequence identity to SEQ ID NO: 1, said method comprising analysing the CmAAP2A DNA, RNA or protein of the plant or plant part. And a method for determining whether a melon plant or plant part comprises at least one copy of a mutant allele of a gene named CmAAP2B is provided, said gene encodes a CmAAP2B protein of SEQ ID NO: 4 or a protein comprising at least 90%, 91%, 92%, 93%, 94% or 95% sequence identity to SEQ ID NO: 4, said method comprising analysing the CmAAP2B DNA, RNA or protein of the plant or plant part.

In one aspect, especially in respect of the European Patent Convention, the melon plant according to the invention is "not obtained exclusively by an essentially biological process", or in one aspect the mutant cmaap2a and/or cmaap2b allele is not a natural mutant allele. If such a disclaimer is present in the claim of the European patent, it should be noted that using a melon plant comprising a mutant allele (e.g. a commercial variety of the applicant) to cross the mutant allele into a different background of melon will still be seen as falling under the claim, even though an exclusively essentially biological process (only crossing and selection) may have been used to transfer the allele into a different background.

In one aspect the natural mutant cmaap2a allele is not the allele described in Example 2.

Watermelon Plants and Plants Parts

The two orthologs of the melon CmAAP2A and CmAAP2B genes were found in watermelon and were named ClAAP2A and ClAAP2B, respectively. ClAAP2A and ClAAP2B were both located on chromosome 4 of watermelon.

In one aspect a plant or plant part of the species *Citrullus lanatus* ssp. vulgaris is provided comprising at least one copy of a mutant allele of a gene named ClAAP2A, said gene encodes a ClAAP2A protein of SEQ ID NO: 2 or a protein comprising at least 90%, 91%, 92%, 93%, 94%, 95%, 96%, 97%, 98% or 99% sequence identity to SEQ ID NO: 2, wherein said mutant allele results in reduced expression or no expression of the ClAAP2A gene or wherein the mutant allele encodes a protein having a decreased function or a loss-of-function compared to the wild type ClAAP2A protein.

As mentioned above, watermelon was found to contain a second gene, named ClAAP2B, just like ClAAP2A located also on chromosome 4. The second gene encodes a protein with high sequence identity to ClAAP2A (92.5%), it also has the same 2-dimensional structure (with a Aa_trans domain being a large part of the protein) and 3-dimensional structure (as can for example be seen when analysing both proteins in raptorx.uchicago.edu). It is therefore very likely that ClAAP2A and ClAAP2B have the same function in the plant and that mutant ClAAP2B alleles have the same effect on reducing susceptibility to *P. cubensis*.

Thus, in one aspect a plant or plant part of the species *Citrullus lanatus* ssp. vulgaris is provided comprising at least one copy of a mutant allele of a gene named ClAAP2B, said gene encodes a ClAAP2B protein of SEQ ID NO: 5 or a protein comprising at least 90%, 91%, 92%, 93%, 94%, 95%, 96%, 97%, 98% or 99% sequence identity to SEQ ID NO: 5, wherein said mutant allele results in reduced expression or no expression of the ClAAP2B gene or wherein the mutant allele encodes a protein having a decreased function or a loss-of-function compared to the wild type ClAAP2B protein.

In one aspect a plant or plant part of the species *Citrullus lanatus* ssp. vulgaris is provided comprising at least one copy of a mutant allele of a gene named ClAAP2A and/or of a mutant allele of a gene named ClAAP2B, wherein said ClAAP2A gene encodes a ClAAP2A protein of SEQ ID NO: 2 or a protein comprising at least 90%, 91%, 92%, 93%, 94%, 95%, 96%, 97%, 98% or 99% sequence identity to SEQ ID NO: 2, and said ClAAP2B gene encodes a ClAAP2B protein of SEQ ID NO: 5 or a protein comprising at least 90%, 91%, 92%, 93%, 94%, 95%, 96%, 97%, 98% or 99% sequence identity to SEQ ID NO: 5, and wherein said mutant claap2a allele results in reduced expression or no expression of the ClAAP2A gene or wherein the mutant claap2a allele encodes a protein having a decreased function or a loss-of-function compared to the wild type ClAAP2A protein, and wherein said mutant claap2b allele results in reduced expression or no expression of the ClAAP2B gene or wherein the mutant claap2b allele encodes a protein having a decreased function or a loss-of-function compared to the wild type ClAAP2B protein.

Gene expression can be measured as known in the art, e.g. by measuring the mRNA transcript levels by quantitative real-time PCR (qRT-PCR). See for example Berg et al. BMC Plant Biology 2015, 15: 243, page 1-17, see page 15.

A plant may thus either have a mutant claap2a or a mutant claap2b allele (i.e. a single mutant allele), or both (double mutant). The plant comprising a single mutant claap2a allele in homozygous form showed reduced susceptibility to the oomycete *Pseudoperonospora cubensis* compared to the susceptible control plant lacking any of the mutant alleles (i.e. comprising wild type alleles) and the same is expected for a plant comprising a single mutant claap2b allele in homozygous form. In a plant comprising a double mutant allele the susceptibility to *P. cubensis* may be even reduced more strongly than in the single mutant plant. This can be tested by combining mutant claap2a and mutant claap2b alleles in a single plant, either by directly generating double mutants in a single plant (using e.g. CRISPR constructs with multiple single guide RNAs, sgRNAs, targeting both genes) or by crossing plants comprising single mutant alleles with each other and selecting progeny comprising both mutant alleles.

Thus, in a further aspect the mutant claap2a and/or claap2b allele confers reduced susceptibility to the oomycete *Pseudoperonospora cubensis* at least when the mutant claap2a and/or claap2b allele is in homozygous form compared to a plant or plant part homozygous for the wild type allele of the ClAAP2A and ClAAP2B gene. The reduced susceptibility can be measured in a disease assay by e.g. assessing the *P. cubensis* induced symptom development, e.g. leaf yellowing/chlorosis and/or sporulation, at one or more time points after inoculation, in a plant line or variety comprising the mutant claap2a allele and/or claap2b allele in homozygous form, compared to a susceptible control plant line or variety comprising the wild type ClAAP2A allele and wild type ClAAP2B allele in homozygous form when grown under the same conditions. The plant line comprising the mutant claap2a allele and/or claap2b allele in homozygous would be considered to have reduced susceptibility when the average symptom development, e.g. leaf yellowing/chlorosis and/or average sporulation, is significantly less compared to the average leaf yellowing/chlorosis and/or average sporulation in the susceptible control. See Examples for a suitable disease assay for assessing leaf yellowing/chlorosis and sporulation in cucumber. This assay can be adapted to watermelon. Alternatively methods known in the art can be used.

An endogenous watermelon ClAAP2A gene (or an ClAAP2A allele thereof) is a gene (or allele) encoding a (wild type, functional) ClAAP2A protein which comprises at least 90% or more sequence identity to the watermelon ClAAP2A protein of SEQ ID NO: 2. It comprises an Aa_trans domain as shown in FIG. 1. The presence of an Aa_trans domain can be checked by analysing the amino acid sequence in InterPro, at ebi.ac.uk/interpro/search/sequence-search.

An endogenous watermelon ClAAP2B gene (or an ClAAP2B allele thereof) is a gene (or allele) encoding a (wild type, functional) ClAAP2B protein which comprises at least 90% or more sequence identity to the watermelon ClAAP2B protein of SEQ ID NO: 5. It comprises an Aa_trans domain as shown in FIG. 2. The presence of a Aa_trans domain can be checked by analysing the amino acid sequence in InterPro, at ebi. ac.uk/interpro/se arch/sequence-search.

In the plant or plant part comprising said mutant claap2a allele and/or mutant claap2b allele, said mutant claap2a or claap2b allele results in reduced expression or no expression of the (endogenous, wild type) ClAAP2A gene or ClAAP2B gene, respectively, or said mutant claap2a or claap2b allele encodes a protein having a decreased function or a loss-of-function compared to the wild type ClAAP2A or ClAAP2B protein, respectively, i.e. said mutant allele encodes a mutant claap2a protein or claap2b protein.

Thus, as a result of the mutation in the endogenous ClAAP2A and/or ClAAP2B allele, there is either less or even no wild type ClAAP2A or ClAAP2B mRNA transcript being produced by the mutant allele (e.g. if the mutation is in a regulatory sequence of the endogenous allele) in the plant cell and plant, or as a result of the mutation a mutant ClAAP2A protein or ClAAP2B protein is produced by the mutant allele, e.g. comprising one or more amino acids replaced, deleted or inserted compared to the functional wild type protein, thereby leading to a reduced function or loss of function of the (mutant) claap2a and/or claap2b protein. And consequently, when the mutant claap2a and/or claap2b allele is in homozygous form in the genome of the plant, the plant will be at least partially resistant against downy mildew/less susceptible to *P. cubensis* than the plant comprising two functional/wild type ClAAP2A alleles and two functional/wild type ClAAP2B alleles.

No expression of the mutant claap2a or claap2b allele means that no transcript (mRNA) is being transcribed from the mutant allele, due to e.g. a mutation in the promoter sequence being present. So if the mutant allele is in homozygous form, the wild type mRNA, encoding the functional protein will not be present in plant tissue in which it is otherwise present in the susceptible control (comprising the wild type alleles), such as roots, stems, hypocotyl, cotyledon, leaf and/or flower. An allele having no expression may also be referred to as a knock-out allele herein.

Reduced (or decreased) expression of the mutant claap2a allele or of the mutant claap2b allele means for example that only 50%, or less, of the amount of transcript (mRNA) is transcribed from the mutant allele compared to the wild type allele, or only equal to or less than 40%, 30%, 20%, 10%, or 5% of the amount of transcript (mRNA) is transcribed from the mutant allele compared to the wild type allele. In other words, when the mutant allele is in homozygous form, the wild type mRNA, encoding the functional protein will be present in plant tissue in which it is otherwise present, such as leaves, roots, hypocotyl, cotyeldons or stems, but at a significantly lower amount than in a plant which is homozygous for the wild type allele. This will result in significantly less functional wild type protein being present, which in turn results in reduced susceptibility of the plant. An allele having reduced expression may also be referred to as a knock-down allele herein.

The decrease in the expression of claap2a or claap2b allele can, for example, be determined by measuring the quantity of RNA transcripts (e.g. mRNA), e.g. by qRT-PCR. Similarly, the decrease in the amount of ClAAP2A or ClAAP2B protein, can, for example, be determined by immunological methods such as Western blot analysis, ELISA (Enzyme Linked Immuno Sorbent Assay) or RIA (Radio Immune Assay). Here, a decrease preferably means a reduction in the amount of ClAAP2A proteins or ClAAP2B protein by at least 50%, in particular by at least 70%, or by at least 85% and particularly by at least 95%.

In another embodiment the watermelon plant or plant part comprises a mutant claap2a allele, wherein the protein encoded by the mutant claap2a allele comprising one or more amino acids replaced, inserted or deleted compared to the ClAAP2A wild type protein of SEQ ID NO: 2 (or a functional variant thereof comprising at least 90% sequence identity to SEQ ID NO: 2), especially one or more amino acids replaced, inserted and/or deleted in the conserved Amino Acid Transporter Domain at amino acid 20 to 453 of SEQ ID NO: 2 or in an Amino Acid Transporter Domain comprising at least 95%, 96%, 97%, 98% or 99% sequence identity to amino acid 20 to 453 of SEQ ID NO: 2. Such a protein can have a reduced activity or no activity in vivo.

In another embodiment the watermelon plant or plant part comprises a mutant claap2b allele, wherein the protein encoded by the mutant claap2b allele comprising one or more amino acids replaced, inserted or deleted compared to the ClAAP2B wild type protein of SEQ ID NO: 5 (or a functional variant thereof comprising at least 90% sequence identity to SEQ ID NO: 5), especially one or more amino acids replaced, inserted and/or deleted in the conserved Amino Acid Transporter Domain at amino acid 20 to 453 of SEQ ID NO: 5 or in an Amino Acid Transporter Domain comprising at least 95%, 96%, 97%, 98% or 99% sequence identity to amino acid 20 to 453 of SEQ ID NO: 5. Such a protein can have a reduced activity or no activity in vivo.

In one embodiment the plant or plant part comprises both of the above mutant alleles (double mutant).

In one aspect, the watermelon plant or plant part comprises a mutant claap2a allele and/or a mutant claap2b allele, wherein the mutant claap2a allele encodes a protein that is truncated compared to the wild type ClAAP2A protein and/or the mutant claap2b allele encodes a protein that is truncated compared to the wild type ClAAP2B protein. The truncated protein may comprise additional amino acids, for example a frame shift mutation may result in the truncated protein comprising an amino acid sequence which is different from the amino acid sequence of the wild type protein. A truncated protein can have a reduced activity or even no activity in vivo, especially when all or part of the Aa_trans domain is missing and/or is replaced by different amino acids. Thus in one aspect the mutant claap2a allele encodes a protein that is truncated compared to the wild type ClAAP2A protein and/or the mutant claap2b allele encodes a protein that is truncated compared to the wild type ClAAP2B protein, wherein at least one, two, three, four, 5, 6, 7, 8, 9, 10, 15, 20, 30, 40, 50 or more amino acids of the Aa_trans domain are missing or are replaced by different amino acids compared to the wild type protein. In one aspect at least 13, 14, 15, 20, 30, 40, 50 or more amino acids of the C-terminal end of the ClAAP2A or ClAAP2B protein are missing or are replaced by one or more different amino acids compared to the wild type protein.

The 2-dimensionl analysis showed that a large part of the ClAAP2A protein and ClAAP2B protein consists of the Aa_trans domain. 3-dimensional analysis predicts that both the ClAAP2A protein and the ClAAP2B protein consists of 67% helix structure and 32% loop structures (coils). This means that any amino acid insertion, deletion or replacement, especially of one or more amino acids in the Aa_trans domain, will likely change the 3-dimensional structure of the protein and reduce its in vivo function or even abolish its in vivo function. For example, a mutation which results in a change of a codon into a STOP codon, will result in a truncated protein.

In one aspect the watermelon plant comprises a mutant claap2a and/or claap2b allele (in homozygous or heterozygous form), wherein the encoded protein lacks the 95 C-terminal amino acids of SEQ ID NO: 2 or SEQ ID NO: 5, respectively, or of a protein comprising at least 90% sequence identity to SEQ ID NO: 2 or to SEQ ID NO: 5, respectively. For example a mutation in the codon encoding amino acid number 372 (W, Tryptophan) to a stop codon, leads to a truncation of the ClAAP2A (or ClAAP2B) protein, whereby the protein comprises amino acids 1 to 371 of SEQ ID NO: 2 (or SEQ ID NO: 5) and lacks amino acids 372 to 466 of SEQ ID NO: 2 (or SEQ ID NO: 5), i.e. the 95 C-terminal amino acids are missing. As these 95 C-terminal amino acids comprise 82 amino acids of the AA_trans domain, the protein has reduced function or more likely even loss-of-function in vivo. The watermelon plant comprising this mutant allele in homozygous form has a reduced susceptibility to *P. cubensis*. This mutant allele (as well as any other mutant allele described herein) can be induced e.g. in elite breeding lines, or it can also be a natural mutant allele, introgressed into cultivated *Citrullus lanatus* ssp. vulgaris.

Thus, in one aspect a mutant claap2a and/or mutant claap2b allele is provided, wherein the allele is a natural mutant allele obtained (obtainable) from an accession of a wild watermelon plant or wild relative of watermelon plant. The accession in which the natural mutant allele is found may have non-desirable characteristics, such as white flesh, low % TSS, etc. The accession can, therefore, be used as a donor to backcross the mutant allele into cultivated *Citrullus lanatus* ssp. vulgaris. Preferably the mutant allele is backcrossed into cultivated watermelon having good agronomic characteristics, such as a TSS of at least 10%, 11%, 12%, 13%, 14%, 15%, 16%, 17%, 18% or more. Such plants and plant parts are encompassed herein, as are methods for identifying natural mutant alleles and/or introgressing them into cultivated watermelon.

A mutant claap2a allele encoding a truncated ClAAP2A protein may, thus be an allele which encodes a protein that lacks at least 13, 14, 15, 20, 30, 40, 50, 60, 70, 80, 90, 95, 100, 120, 130, 140, 150, 160, 170, 180, 190, 200, 250, 300, 350, 400 or even more of the C-terminal amino acids compared to the wild type ClAAP2A protein of SEQ ID NO: 2, or of a variant comprising at least 90%, 91%, 92%, 93%, 94%, 95%, 96%, 97%, 98% or 99% sequence identity to SEQ ID NO: 2.

A mutant claap2b allele encoding a truncated ClAAP2B protein may, thus be an allele which encodes a protein that lacks at least 13, 14, 15, 20, 30, 40, 50, 60, 70, 80, 90, 100, 120, 130, 140, 150, 160, 170, 180, 190, 200, 250, 300, 350, 400 or even more of the C-terminal amino acids compared to the wild type ClAAP2B protein of SEQ ID NO: 5, or of a variant comprising at least 90%, 91%, 92%, 93%, 94%, 95%, 96%, 97%, 98% or 99% sequence identity to SEQ ID NO: 5.

Thus in one aspect the mutant allele results in a truncated ClAAP2A protein or a truncated ClAAP2B protein being produced, which truncated protein has decreased function or loss-of-function. A truncation may for example result in the loss of the C-terminal end (carboxyl terminal end) of the protein, whereby part or all of the Aa_trans domain is absent. For example only the N-terminal part (amino terminal part) of the protein may still be present. Mutant alleles which express a truncated ClAAP2A protein or a truncated ClAAP2B protein can be induced whereby, for example, a codon in one of the exons is changed into a premature stop codon or splice-site mutations or frame-shift mutations can also lead to premature stop codons and truncated proteins.

In another aspect the mutant allele results in a mutant ClAAP2A or ClAAP2B protein, which comprises one or more amino acids inserted, replaced and/or deleted compared to the wild type protein. As mentioned, especially insertion, replacement and/or deletion of one or more amino acids in the Aa_trans domain will result in a mutant protein that has decreased function or loss of function, and will, in homozygous form in the watermelon plant, reduce susceptibility to *P. cubensis.*

Whether the insertion, replacement and/or deletion of one or more amino acids, or a truncation or mutant allele not expressed or having reduced expression as described elsewhere herein, actually results in a reduced susceptibility in vivo can be tested by carrying out a disease assay for a plant comprising the mutant allele (or double mutant) in homozygous form.

Optionally the increase in free amino acids following *P. cubensis* infection can be compared between the plant comprising the mutant claap2a and/or claap2b allele and the susceptible control comprising the wild type alleles (WT). A reduced increase in free amino acids, especially in Ala, Gly, Val, Leu, Ile, Thr, Ser, Pro and/or Gln compared to the increase in the susceptible control (comprising functional wild type ClAAP2A and ClAAP2B alleles) indicates that the mutant allele has reduced function or a loss of function in vivo.

In yet another aspect the mutant allele results in reduced expression or no expression of the allele and thus reduced amounts or no protein of the wild type ClAAP2A or ClAAP2B protein being produced in the plant or plant part. For example, the promoter or another regulatory element of the ClAAP2A or ClAAP2B allele may be comprise one or more nucleotides inserted, deleted and/or replaced.

Thus, a mutant allele of a ClAAP2A protein-encoding gene and/or ClAAP2B protein-encoding gene causes a plant to have reduced susceptibility to *P. cubensis*, at least when the plant is homozygous for the mutant allele. Concerning the embodiments of the invention, the mutation in the mutant allele of a ClAAP2A protein-encoding gene or ClAAP2B protein encoding gene (i.e. in the mutant claap2a allele and/or claap2b allele) can be any mutation, including one or more deletions, truncations, insertions, point mutations, nonsense mutations, missense or non-synonymous mutations, splice-site mutations, frame shift mutations and/or mutations in regulatory sequences (for example in the promoter sequence). In one aspect the mutation in the mutant claap2a allele and/or claap2b allele is a point mutation. The mutation can occur in a DNA sequence comprising the coding sequence of a ClAAP2A protein-encoding gene or ClAAP2B protein-encoding gene, or in a RNA sequence encoding a ClAAP2A protein or ClAAP2B protein, or it can occur in the amino acid molecule of the ClAAP2A or ClAAP2B protein.

Concerning a DNA sequence of ClAAP2A protein-encoding gene or ClAAP2B protein-encoding gene, the mutation can occur in the coding sequence (cds, composed of the exons) or it can occur in non-coding sequences like 5'- and 3'-untranslated regions, introns, promoters, enhancers etc. In respect to RNA encoding a ClAAP2A protein or ClAAP2B protein, the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted or deleted in the conserved Aa_trans domain. For example, truncation of the protein to cause deletion of the Aa_trans domain, or part thereof, will result in a loss of function or decrease of function of the protein.

A further embodiment of the invention therefore concerns watermelon plant cells or plants according to the invention comprising a mutant allele of a ClAAP2A protein-encoding gene and/or of a ClAAP2B protein-encoding gene, characterized in that the mutant claap2a allele and/or mutant claap2b allele comprises or effects one or more of the mutations selected from the group consisting of a) a deletion, truncation, insertion, point mutation, nonsense mutation, missense or non-synonymous mutation, splice-site mutation, frame shift mutation in the genomic sequence;
b) a mutation in one or more regulatory sequences;
c) a deletion, truncation, insertion, point mutation, nonsense mutation, missense or non-synonymous mutation, splice-site mutation, frame shift mutation in the coding sequence;
d) a deletion, truncation, insertion, point mutation, nonsense mutation, missense or non-synonymous mutation, splice-site mutation, frame shift mutation in the pre-mRNA or mRNA; and/or
e) a deletion, truncation, insertion or replacement of one or more amino acids in the ClAAP2A or ClAAP2B protein.

A different embodiment of the invention concerns watermelon plant cells, plant parts or plants comprising or synthesising an mRNA encoding a ClAAP2A protein and/or ClAAP2B protein, wherein the mRNA encoding a ClAAP2A protein or ClAAP2B protein has one or more mutations selected from the group consisting of a) a deletion mutation;
b) a missense or non-synonymous mutation;
c) a frame shift mutation; and/or
d) a non-sense mutation.

In another embodiment of the invention, plant cells or plants according to the invention comprise or synthesise an mRNA encoding a ClAAP2A protein and/or ClAAP2B protein having one or more mutations, wherein the mRNA is transcribed from a mutant allele of a ClAAP2A protein-encoding gene and/or from a mutant allele of a ClAAP2B protein-encoding gene. Comprised by these embodiments of the invention are plant cells, plant parts or plants according to the invention comprising or synthesising an mRNA transcribed from a mutant allele of a ClAAP2A protein-encoding gene and/or ClAAP2B protein encoding gene, characterized in that the mRNA comprises a deletion mutation and/or a missense or non-synonymous mutation and/or a frame shift mutation and/or a non-sense mutation, compared to the corresponding (DNA) coding sequence of the mutant allele of the ClAAP2A or ClAAP2B protein-encoding gene from which the mRNA is transcribed. Thus, in one aspect any mutation which affects pre-mRNA splicing is encompassed, i.e. which modifies the normal pre-mRNA splicing process, thereby leading to a different mRNA molecule.

An "mRNA coding sequence" shall have the common meaning herein. An mRNA coding sequence corresponds to the respective DNA coding sequence of a gene/allele apart from that thymine (T) is replaced by uracil (U).

In one aspect the watermelon plant or plant part is homozygous for a mutant claap2a allele and/or for a mutant claap2b allele described herein. Because both the ClAAP2A gene and the ClAAP2B gene are deemed to be recessive, the reduction in susceptibility is seen phenotypically when the plant is homozygous for one or both of the mutant alleles, although it is not excluded that an effect may also be seen when the plant is heterozygous for one or both mutant alleles.

In one aspect the mutant claap2a and/or claap2b allele is an induced mutant allele, while in a different aspect the mutant claap2a and/or claap2b allele is a "natural allele" or "natural mutant allele" introgressed into cultivated watermelon by e.g. backcrossing.

Mutant alleles can be generated by methods known in the art, such as chemical mutagenesis (e.g. EMS treatment), radiation mutagenesis (UV, gamma rays etc.), targeted mutagenesis, such as Crispr/Cas9 or TALENS.

Suitable chemical mutagens include ethyl methanesulfonate (EMS), methylmethane sulfonate (MMS), N-ethyl-N-nitrosurea (ENU), trimethylamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitrosoguanidine (MNNG), nitrosoguanidine, 2-aminopurine, 7,12-dimethylbenz(a)anthracene (DMBA), ethylene oxide, hexamethylphosphoramide, bisulfan, diepoxyalkanes, diepoxyoctrane (DEO), diepoxybutane (DEB), 2-methoxy-6-choloro9[3-ethyl-2-chloro-ethyl]aminopropylamine]lacridine dihydrochloride (ICR-170), and formaldehyde. Suitable radiation is UV radiation or radioactive radiation.

Biotechnological methods for introducing mutations into a desired gene/allele of a plant cell or plant are known in the art. Therefore, mutant alleles of a ClAAP2A and/or ClAAP2B protein-encoding gene can be produced in plant cells or plants by using these methods. Examples for such technologies are in particular mutagenesis techniques or enzymes which induce double stranded DNA breaks (double stranded DNA break inducing enzyme (DSBI)) in the genome of plants. Known and practised technologies are rare-cleaving endonucleases and custom-tailored rare-cleaving endonucleases including but not limited to homing endonucleases, also called meganucleases, transcription activator-like effectors fused to the catalytic domain of a nuclease (TALENs) and so-called CRISPR systems. CRISPR systems is used broadly herein, and does not only encompass the use of the Cas9 nuclease (Crispr/Cas9 system), but also other Crispr systems e.g. using other nucleases, such as Cpf1. These techniques can also be referred to as targeted genome editing techniques or gene editing techniques or targeted mutagenesis techniques.

Thus, technologies such as mutagenesis or targeted genome editing techniques are eligible for introducing a mutation into genes in plant cells or plants. Therefore, plant cells and plants according to the invention having a mutant allele of a ClAAP2A and/or ClAAP2B protein-encoding gene, wherein the mutation into the mutant allele was introduced by genome editing techniques, e.g. using rare-cleaving endonucleases or custom-tailored rare-cleaving endonucleases, are also an embodiment of the invention. Concerning custom-tailored rare-cleaving endonucleases the mutation in the mutant allele of ClAAP2A and/or ClAAP2B protein has preferably been introduced by a meganuclease, a TALENs or a CRISPR system.

In watermelon CRISPR/Cas9 has been used to create mutations, see Tian et al. Plant Cell Rep. 2017, March 36(3):399-406, or Tian et al. Plant Cell Rep. 2018 September 37(9):1353-1356.

Thus, in one aspect the mutant claap2a and/or claap2b alleles are induced mutants, e.g. induced in a breeding line, an inbred line or variety of cultivated watermelon or in one aspect the mutant alleles are induced in wild watermelon or wild relatives of watermelon (and the induced mutant alleles can then be backcrossed into cultivated watermelon). In one aspect the mutant alleles are generated by mutagenesis (e.g. chemical or radiation mutagenesis) or by targeted mutagenesis, especially using the CRISPR system (e.g. Crispr/Cas9 or Crispr/Cpf1 or other nucleases). In one aspect the cultivated watermelon plant comprising the mutant claap2a and/or claap2b alleles is not a transgenic plant, i.e. non transgenic progeny are selected which do not comprise the CRISPR construct.

The cultivated watermelon comprising the induced or natural claap2a and/or claap2b allele may be of any type. It may be a breeding line or a variety. Cultivated watermelons produce diverse fruit sizes (e.g. very small, as described in WO2012069539, e.g. less than 0.9 kg or even equal to or less than 0.65 kg; personal-size of about 3-7 pounds, i.e. about 1.4 to 3.2 kg; icebox sizes of about 6-12 pounds, i.e. about 2.7 to 5.5 kg; and larger sizes of up to 35 pounds, i.e. about 15.9 kg), fruit flesh colors, and fruit shapes and with different rind colors. The induced or natural claap2a and/or claap2b allele may, therefore, be introduced into cultivated watermelon producing any fruit shape (e.g. elongate, oval, oval elongated, blocky, blocky elongated, spherical or round), fruit surface (e.g. furrow, smooth), flesh color (e.g. red, dark red, scarlet red, coral red, orange, salmon or pink, yellow, canary yellow or white), rind color (e.g. light green; dark green; green-striped with narrow, medium or wide stripes; grey types; with or without spotting; Golden yellow; Crimson type rind, Jubilee type rind; Allsweet type rind; black/dark green), rind thickness, rind toughness, rind pattern (e.g. striped, non-striped, netted), flesh structure/flesh firmness, lycopene and/or vitamin content, different sugar to acid ratios, very good fruit flavour, etc. by breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavour, high vitamin and lycopene content, firm flesh texture, non-fibrous flesh texture, freedom from defects such as hollow heart, rind necrosis, blossom-end rot or cross stitch and good rind characteristics and cracking-resistance). The fruits produced by the line or variety are preferably marketable fruits. In one aspect the average TSS is at least 8% or at least 9%, preferably at least 10%, more preferably at least 11%, 12% or more. Fruit color may be any color, such as red, dark red, scarlet red, coral red, orange, salmon, pink, pinkish red, yellow, canary yellow or white. Preferably the fruit flesh color is uniform.

As mentioned, mutant alleles can also evolve naturally in populations of wild watermelon or wild relatives of watermelon. In one aspect the mutant claap2a and/or claap2b alleles are natural mutant alleles, which have been introgressed into cultivated watermelon. The wild type allele found in cultivated watermelon on chromosome 4 is then replaced with the natural mutant allele, i.e. by meitotic recombination between homologous chromosomes. Wild watermelon accessions can be screened for the presence of such natural mutant alleles, and backcrossing to cultivated watermelon can be used to introgress the natural mutant allele into the cultivated watermelon genome. Such methods and plants produced thereby, comprising one or more introgressions, are encompassed herein.

Thus in one aspect a plant or plant part of the species *Citrullus lanatus* ssp. vulgaris is provided, comprising an introgression fragment from a wild watermelon or wild relative of watermelon on chromosome 4, said introgression fragment comprises a mutant allele of a gene named ClAAP2A, said gene encodes a ClAAP2A protein of SEQ ID NO: 2 or a protein comprising at least 90%, 91%, 92%, 93%, 94% or 95% sequence identity to SEQ ID NO: 2, and/or a mutant allele of a gene named ClAAP2B, said gene encoding a ClAAP2B protein of SEQ ID NO: 5 or a protein comprising at least 90%, 91%, 92%, 93%, 94% or 95% sequence identity to SEQ ID NO: 5, wherein said mutant claap2a and/or claap2b allele results in reduced expression or no expression of the mutant allele or encodes a protein having a decreased function or a loss-of-function compared to the wild type protein.

In one aspect the introgression fragment comprises a natural mutant allele. In another aspect the introgression fragment comprises an induced mutant allele.

In one aspect wild watermelon plants, or wild relatives of watermelon are screened for the presence of a natural mutant claap2a or claap2b allele. This can be done by e.g. analysing (directly or indirectly) the genomic DNA, mRNA (or cDNA) or protein of the ClAAP2A or ClAAP2B gene, using e.g. PCR methods or other molecular methods known in the art, such as sequencing, etc. whereby the presence of a mutant claap2a or claap2b allele can be determined. The wild watermelon plants or wild relatives of watermelon may be CGN accessions, PI accessions (Plant Introductions), or accessions from various seed bank collections. Once an accession is identified to comprise a mutant claap2a or claap2b allele, the accession can be crossed to cultivated watermelon, and the mutant allele can be introgressed into the genome of cultivated watermelon by e.g. backcrossing. The cultivated watermelon introgression line is preferably selfed one or more times to ensure the mutant allele is in homozygous form and the line can then be tested for reduced susceptibility to *P. cubensis* compared to e.g. the original cultivated watermelon (e.g. the recurrent parent) comprising the wild type, functional ClAAP2A and ClAAP2B alleles in homozygous form.

Also encompassed herein is a method for identifying a natural mutant claap2a and/or a natural mutant claap2b allele. The method involves determining whether a wild watermelon or wild relative of watermelon comprises a natural mutant allele and optionally transferring the natural mutant allele into cultivated watermelon by traditional breeding techniques. Wild plant accessions are generally very heterogenous and also may comprise various other genes which affect downy mildew resistance. The effect of the mutant allele on the susceptibility of the plant will be difficult to assess in the wild accession and the mutant allele is preferably first transferred into a breeding line, preferably a breeding line which is susceptible to downy mildew. In one embodiment therefore a method for transferring a natural mutant claap2a and/or a natural mutant claap2b allele from a wild watermelon plant into a cultivated watermelon plant is provided, comprising a) identifying or providing a wild watermelon comprising a natural mutant claap2a and/or claap2b allele
b) crossing the mutant allele(s) into cultivated watermelon, preferably a cultivated watermelon line which is susceptible to *P. cubensis*, and
c) determining the effect of the mutant allele on the susceptibility to *P. cubensis*.

The same can of course be done for induced mutant alleles, which may be induced in wild watermelon, whereby in step a) one provides or identifies a wild watermelon comprising an induced mutant allele. The method may then be preceded by a step wherein mutations are induced.

The cultivated watermelon plant described herein, comprising either an induced mutant or a natural mutant claap2a and/or claap2b allele in its genome preferably comprises either or both mutant alleles in homozygous form, as the reduced susceptibility against *P. cubensis* is at least seen when the allele is in homozygous form. Plants comprising either or both mutant alleles in heterozygous form are also encompassed herein.

The cultivated watermelon plant comprising a mutant claap2a and/or a mutant claap2b allele according to the invention may be of any type, e.g. it may be of one of the following types: diploid, triploid, tetraploid, open pollinated, inbred line, double haploid line, male sterile line, pollinizer, rootstock, scion or F1 hybrid. In triploid watermelon the mutant claap2a and/or a mutant claap2b allele may be present in three copies, in tetraploid watermelon the mutant claap2a and/or a mutant claap2b allele may be present in four copies. Triploid watermelon plants produce seedless fruits. Seeds of triploid watermelons are made by crossing a tetraploid female parent line with a diploid make parent line. The tetraploid parent line is made by chromosome doubling of a diploid line, followed by stabilization of the line by several generations of selfing. Thus in one aspect a diploid line comprising the mutant claap2a and/or a mutant claap2b allele in homozygous form is used to generate a tetraploid line comprising four copies of the mutant claap2a and/or a mutant claap2b allele.

The cultivated watermelon plant according to the invention is in one aspect a triploid F1 hybrid plant or seed, comprising three copies of the mutant claap2a and/or a mutant claap2b allele.

The cultivated watermelon plant according to the invention is in one aspect a diploid F1 hybrid plant or seed, comprising two copies of the mutant claap2a and/or a mutant claap2b allele, i.e. homozygous for the mutant claap2a allele and/or homozygous for the mutant claap2b allele.

The cultivated watermelon plant preferably has good agronomic and good fruit quality characteristics. The cultivated watermelon plant is in one aspect uniform, both genetically and phenotypically. Especially fruit characteristics are uniform, e.g. regarding shape, color, fruit flesh color, brix or TSS (total soluble solids), flavour, etc. Likewise seed characteristics (i.e. characteristics of the seeds from which the plant is grown) are uniform, e.g. seed size, seed color, etc. In one aspect the watermelon fruits (of the plant comprising the induced mutant claap2a and/or claap2b allele or natural claap2a and/or claap2b mutant allele) have an average TSS at maturity or harvest stage of at least 9%, 10%, 11%, 12%, 13%, 14%, 15%.

The average % TSS (or brix) can be measured as known in the art, e.g. using a digital hand refractometer and measuring the TSS of several fruits of a line or variety. See for example Burger et al. 2003, J American Soc Hort Science 128(4): 537-540 on page 538 at Measurement of TSS.

Also a seed is provided from which a plant or plant part according to the invention can be grown.

Further a watermelon fruit produced by a plant according to the invention is provided, wherein the fruit comprises the mutant claap2a and/or claap2b allele, preferably in homozygous form, optionally in three copies in a triploid fruit or in four copies in a tetraploid fruit.

Likewise plant parts of a plant according to the invention are provided, wherein the plant part is a cell, a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther. The plant part comprises in its genome a mutant claap2a and/or a mutant claap2b allele of the invention, preferably in homozygous form, optionally in three copies in a triploid plant part or in four copies in a tetraploid plant part. In one aspect the cell is a non-propagating or a non-regenerable cell. In one aspect the non-propagating or non-regenerable cell is part of a tissue or organ of the plant. In a different aspect the non-propagating or non-regenerable cell is in a cell culture or tissue culture.

Also a cell culture or a tissue culture of cells or tissues comprising in its genome a mutant claap2a and/or a mutant claap2b allele of the invention is encompassed herein. Further a plant regenerated from such a cell or tissue culture is encompassed.

Further a vegetatively propagated plant propagated from a plant part according to the invention is provided.

Also a food or feed product comprising cells according to the invention are provided, such as parts of watermelon fruits.

In one embodiment a method of watermelon fruit production is provided, said method comprising growing a plant according to the invention, comprising a mutant claap2a and/or claap2b allele, preferably in homozygous form, optionally in three copies in a triploid plant or in four copies in a tetraploid plant, said method optionally comprising a reduced treatment with fungicides compared to a susceptible control plant, e.g. a plant comprising a wild type ClAAP2A allele and a wild type ClAAP2B allele in homozygous form, and optionally harvesting the fruits produced by said plants. As the plant is less susceptible to *P. cubensis*, less fungicide treatment (lower amounts and/or less frequent applications of fungicides) is needed.

*P. cubensis* infects watermelon plants in both the field and the greenhouse, therefore in the above method plants of the invention are grown either in the field or in greenhouses.

The pathogen has a high potential to become resistant to fungicides, it was for example the first oomycete with documented resistance to metalaxyl and reduced sensitivity to mancozeb. It has also been described to have developed resistance to strobulurin fungicides. Less fungicide treatment will reduce the risk of resistance developing.

As mentioned previously, in watermelon mutant claap2a and/or claap2b alleles can be induced, i.e. the can be generated by mutating the endogenous ClAAP2A and/or ClAAP2B allele in cultivated watermelon seeds or plants or plant parts (or optionally in wild plants) and/or by selecting induced mutants e.g. tissue culture induced mutants or TILLING mutants.

Therefore, methods for producing and/or selecting plants having mutant claap2a and/or claap2b alleles, resulting in a knock-down or knock-out of gene expression and consequently less or no wild type protein being produced, or mutant alleles encoding mutant proteins having a decreased function or loss-of-function compared to the wild type protein are encompassed herein. To generate such mutant alleles conventional mutagenic agents, like chemicals or high energy radiation (e.g. x-rays, neutron radiation, gamma radiation or UV radiation) may be used. It is also possible to generate mutant alleles by means of biotechnology methods as described above (e.g. targeted gene editing technology).

In one aspect the invention provides a method for generating and/or identifying a watermelon plant comprising a mutant allele of a gene named ClAAP2A, said gene encodes a ClAAP2A protein of SEQ ID NO: 2 or a protein comprising at least 90%, 91%, 92%, 93%, 94% or 95% sequence identity to SEQ ID NO: 2, comprising identifying or selecting a plant in a mutant watermelon population, or progeny thereof obtained by selfing, comprising a mutant claap2a allele, or generating a mutant plant comprising a mutant claap2a allele using a targeted genome editing technique, such as a Crispr system (e.g. Crispr/Cas9).

In another aspect the invention provides a method for generating a watermelon plant comprising a mutant allele of a gene named ClAAP2B, said gene encodes a ClAAP2B protein of SEQ ID NO: 5 or a protein comprising at least 90%, 91%, 92%, 93%, 94% or 95% sequence identity to SEQ ID NO: 5, comprising identifying or selecting a plant in a mutant watermelon population, or progeny thereof obtained by selfing, comprising a mutant claap2b allele, or generating a watermelon plant comprising a mutant claap2b allele using a targeted genome editing technique, such as a Crispr system (e.g. Crispr/Cas9).

A 'mutant watermelon population' or 'population of mutant watermelon plants' refers to a plurality of watermelon seeds or plants or plant parts which have been treated with a conventional mutagenic agents, like chemicals or high energy radiation (e.g. x-rays, neutron radiation, gamma radiation or UV radiation) or progeny thereof obtained by selfing, to ensure that mutations are in homozygous form. These can be plants or seeds or plant parts of a cultivated watermelon breeding line, variety, inbred line or any plurality of cultivated watermelon plants or seeds. Alternatively these may be wild watermelon plants or wild relatives of watermelon.

Watermelon plants according to the invention, comprising reduced susceptibility to *P. cubensis*, can be produced by introducing one or more mutations into an allele of a ClAAP2A protein-encoding gene and/or into an allele of a ClAAP2B protein-encoding gene.

A further embodiment of the present invention, therefore, concerns a method for production of a watermelon plant comprising the steps of a) providing a population of mutant watermelon plants,
b) optionally selecting a plant which is less susceptible to *P. cubensis* than a non-mutated plant,
c) determining if a plant of the mutant population of a) or selected under b) has a mutation in an allele of a ClAAP2A protein-encoding gene and/or in an allele of a ClAAP2B protein-encoding gene, optionally
d) growing/cultivating the plants obtained under c).

In one aspect is a method for production of a watermelon plant comprising the steps of a) introducing mutations in a population of watermelon plants (and optionally selfing the plants),
b) optionally selecting a plant which is less susceptible to *P. cubensis* than a non-mutated plant,
c) determining if the plant selected under b) has a mutation in an allele of a ClAAP2A protein-encoding gene and/or in an allele of a ClAAP2B protein-encoding gene and selecting a plant comprising such a mutation, and optionally
d) growing/cultivating the plants obtained under c).

However, in one aspect the order of the steps can also be different, comprising:

a) providing a population of mutant watermelon plants,
b) determining if a plant of the mutant population of a) has a mutation in an allele of a ClAAP2A protein-encoding gene and/or in an allele of a ClAAP2B protein-encoding gene, optionally
c) selecting a plant comprising a mutation in an allele of a ClAAP2A protein-encoding gene and/or in an allele of a ClAAP2B protein-encoding gene, and optionally
d) selfing the plant of b) or c) to generate a plant comprising the mutant allele in homozygous form, and optionally
e) determining if the plant of step c) or d) is less susceptible to *P. cubensis* than a non-mutated plant.

Or the steps may comprise:

a) introducing mutations in a population of watermelon plants (and optionally selfing the plants)
b) determining if a plant of a) has a mutation in an allele of a ClAAP2A protein-encoding gene and/or in an allele of a ClAAP2B protein-encoding gene and optionally c) selecting a plant comprising such a mutation, and optionally d) selfing the plant of b) or c) to generate a plant comprising the mutant allele in homozygous form, and optionally e) determining if the plant of step c) or d) is less susceptible to *P. cubensis* than the non-mutated plant.

A non-mutated plant may be e.g. a susceptible control plant, such as a plant comprising wild type, functional ClAAP2A and ClAAP2B alleles in homozygous form.

Optionally, the above methods comprises selecting a plant comprising at least one copy of a mutant allele of a gene encoding a ClAAP2A or ClAAP2B protein. The selected plants are also an embodiment.

Chemical substances, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide (NaN3) is described, for example, in Jauhar and Siddiq (1999, Indian Journal of Genetics, 59 (1), 23-28), in Rao (1977, Cytologica 42, 443-450), Gupta and Sharma (1990, Oryza 27, 217-219) and Satoh and Omura (1981, Japanese Journal of Breeding 31 (3), 316-326). The production of wheat mutants using NaN3 or maleic hydrazide is described in Arora et al. (1992, Annals of Biology 8 (1), 65-69). An overview of the production of wheat mutants using different types of energy-rich radiation and chemical substances is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutations in triticale. The use of MMS (methyl methane sulphonic acid) and gamma radiation for the production of millet mutants is described in Shashidhara et al. (1990, Journal of Maharashtra Agricultural Universities 15 (1), 20-23).

All these methods are basically suitable in the method for production of a plant according to the invention for producing mutant alleles in genes encoding a ClAAP2A or ClAAP2B protein.

The plants generated and/or selected by these methods are also an embodiment of the invention. These plants can be used to make breeding lines and varieties comprising the mutant alleles.

Selecting plants having reduced susceptibility to *P. cubensis* can be done in a disease assay as e.g. described in the Examples. As the phenotype is at least seen in homozygous condition, selfing of the plant or the population of mutagenized plants is preferred before phenotyping. Mutations in the appropriate alleles, in particular in alleles of ClAAP2A protein-encoding gene or ClAAP2B protein encoding gene, can be found with the help of methods known to the person skilled in the art. In particular, analyses based on hybridisations with probes (Southern Blot), amplification by means of polymerase chain reaction (PCR), sequencing of related genomic sequences and the search for individual nucleotide exchanges can be used for this purpose. Methods, which allow several plants to be investigated for mutations in certain genes in a short time, are particularly suitable. Such a method, so-called TILLING (Targeting Induced Local Lesions IN Genomes), has been described by McCallum et al. (2000, Plant Physiology 123, 439-442).

Other methods for identifying if a plant cell or plant comprises a mutant allele of a ClAAP2A or ClAAP2B protein-encoding gene comprise sequencing of the respective alleles and SNP marker analyses with methods common in the art and e.g. discussed in Thomson (2014, Plant Breeding and Biotechnology 2, 195-212). Also analysis of ClAAP2A or ClAAP2B mRNA being expressed, and optionally quantified, can be used, e.g. to identify mutants having reduced or no gene expression.

These methods are basically suitable for identifying plant cells according to the invention and plants according to the invention having a mutant allele of a ClAAP2A or ClAAP2B protein-encoding gene.

In one aspect, a method for identifying a watermelon plant or plant part or cell comprising in its genome at least one copy of a mutant allele of ClAAP2A and/or ClAAP2B gene is provided, said method comprising determining whether the plant comprises in its genome at least one mutant claap2a allele and/or claap2b allele.

The watermelon plant or plant part may be a cultivated plant or a wild watermelon plant or wild relative of watermelon.

This method may involve analysing (directly or indirectly) the gene expression of the claap2a allele and/or claap2b allele, and/or the genomic nucleotide sequence of the claap2a allele and/or claap2b allele, or the mRNA nucleotide sequence of the claap2a allele and/or claap2b allele, or the protein sequence of the ClAAP2A or ClAAP2B protein, or the protein amounts of the ClAAP2A or ClAAP2B protein of the plant or plant part or plant cell, to determine if the gene expression is knocked down or knocked out compared to the wild type plant or plant part or plant cell, or if the encoded protein comprises one or more amino acid insertions, deletions or replacements compared to the wild type ClAAP2A or ClAAP2B protein.

One method for analysing the presence of a mutant claap2a allele and/or claap2b allele, is for example to assay the presence of a Single Nucleotide Polymorphism (SNP) between the genomic sequence of the mutant claap2a allele and/or claap2b allele and the wild type ClAAP2A and/or ClAAP2B allele, by, for example, designing primers for the SNP and genotyping plants or plant parts for the genotype of that particular SNP. For example a KASP assay can be used for detecting a SNP and thereby the mutant allele.

Likewise primers can be designed for allele specific DNA amplification, e.g. distinguishing a wild type allele from a mutant allele. Such PCR primers can be designed based on the differences between the wild type and the mutant allele. So if the mutant allele comprises a deletion of one or more nucleotides, e.g. in a coding sequence, the primers can be designed to differentiate between the presence of the mutant allele and the wild type allele. The skilled person can easily develop a molecular assay to detect a mutant allele.

So one aspect of the invention comprises a method for determining whether a watermelon plant, plant part or plant cell comprises one or more copies of a mutant claap2a allele and/or claap2b allele by a method selected from analysing one or more nucleotides of the genomic claap2a allele and/or claap2b allele, analysing the mRNA (or cDNA) expressed by the claap2a allele and/or claap2b allele or analysing the ClAAP2A or ClAAP2B protein amount and/or amino acid sequence (using e.g, antibody based detection).

Thus, a method for determining whether a watermelon plant or plant part comprises at least one copy of a mutant allele of a gene named ClAAP2A is provided, said gene encodes a ClAAP2A protein of SEQ ID NO: 2 or a protein comprising at least 90%, 91%, 92%, 93%, 94% or 95% sequence identity to SEQ ID NO: 2, said method comprising analysing the ClAAP2A DNA, RNA or protein of the plant or plant part.

And a method for determining whether a watermelon plant or plant part comprises at least one copy of a mutant allele of a gene named ClAAP2B is provided, said gene encodes a ClAAP2B protein of SEQ ID NO: 5 or a protein comprising at least 90%, 91%, 92%, 93%, 94% or 95% sequence identity to SEQ ID NO: 5, said method comprising analysing the ClAAP2B DNA, RNA or protein of the plant or plant part.

In one aspect, especially in respect of the European Patent Convention, the watermelon plant according to the invention is "not obtained exclusively by an essentially biological process", or in one aspect the mutant claap2a and/or claap2b allele is not a natural mutant allele. If such a disclaimer is present in the claim of the European patent, it should be noted that using a watermelon plant comprising a mutant allele (e.g. a commercial variety of the applicant) to cross the mutant allele into a different background of watermelon will still be seen as falling under the claim, even though an exclusively essentially biological process (only crossing and selection) may have been used to transfer the allele into a different background.

Other Cucurbitaceae Plants and Plant Parts

The two orthologs of the melon and watermelon AAP2A and AAP2B genes were found in other Cucurbit species, namely in Bottle Gourd (LsAAP2A and LsAAP2B) and *Cucurbita pepo* (CpAAP2A and CpAAP2B). In Bitter Gourd only one ortholog was found, named herein McAAP.

The two Bottle Gourd gene were both located on chromosome 1 of *Lagenaria siceraria.*

In one aspect a plant or plant part of the species selected from *Lagenaria siceraria, Cucurbita pepo* and *Momordica charantia* is provided, said *Lagenaria siceraria* plant or plant part comprising at least one copy of a mutant allele of a gene named LsAAP2A, said gene encodes a LsAAP2A protein of SEQ ID NO: 3 or a protein comprising at least 90%, 91%, 92%, 93%, 94%, 95%, 96%, 97%, 98% or 99% sequence identity to SEQ ID NO: 3, or said *Cucurbita pepo* plant or plant part comprising at least one copy of a mutant allele of a gene named CpAAP2A, said gene encodes a CpAAP2A protein of SEQ ID NO: 14 or a protein comprising at least 90%, 91%, 92%, 93%, 94%, 95%, 96%, 97%, 98% or 99% sequence identity to SEQ ID NO: 14, or said *Momordica charantia* plant or plant part comprising at least one copy of a mutant allele of a gene named McAAP, said gene encodes a McAAP protein of SEQ ID NO: 13 or a protein comprising at least 90%, 91%, 92%, 93%, 94%, 95%, 96%, 97%, 98% or 99% sequence identity to SEQ ID NO: 13, wherein said mutant lsaap2a, cpaap2a or mcaap allele results in reduced expression or no expression of the gene or wherein the mutant allele encodes a protein having a decreased function or a loss-of-function compared to the wild type LsAAP2A, CpAAP2A or McAAP protein.

As mentioned above, Bottle Gourd and *C. pepo* were found to contain a second gene, named LsAAP2B and CpAAP2B respectively. The second gene encodes a protein with high sequence identity to LsAAP2B and CpAAP2B respectively, it also has the same 2-dimensional structure (with a Aa_trans domain being a large part of the protein) and 3-dimensional structure (as can for example be seen when analysing both proteins in raptorx.uchicago.edu). It is therefore very likely that LsAAP2A and LsAAP2B, as well as CpAAP2A and CpAAP2B have the same function in the plant and that mutant LsAAP2B and CpAAP2B alleles have the same effect on reducing susceptibility to *P. cubensis.*

Thus, in one aspect a plant or plant part species selected from *Lagenaria siceraria* and *Cucurbita pepo* is provided, said *Lagenaria siceraria* plant or plant part comprising at least one copy of a mutant allele of a gene named LsAAP2B, said gene encodes a LsAAP2B protein of SEQ ID NO: 6 or a protein comprising at least 90%, 91%, 92%, 93%, 94%, 95%, 96%, 97%, 98% or 99% sequence identity to SEQ ID NO: 6, or said *Cucurbita pepo* plant or plant part comprising at least one copy of a mutant allele of a gene named CpAAP2B, said gene encodes a CpAAP2B protein of SEQ ID NO: 15 or a protein comprising at least 90%, 91%, 92%, 93%, 94%, 95%, 96%, 97%, 98% or 99% sequence identity to SEQ ID NO: 15, wherein said mutant lsaap2b or cpaap2b allele results in reduced expression or no expression of the gene or wherein the mutant allele encodes a protein having a decreased function or a loss-of-function compared to the wild type LsAAP2B or CpAAP2B protein.

In one aspect a plant or plant part of the species *Lagenaria siceraria* is provided comprising at least one copy of a mutant allele of a gene named LsAAP2A and/or of a mutant allele of a gene named LsAAP2B, wherein said LsAAP2A gene encodes a LsAAP2A protein of SEQ ID NO: 3 or a protein comprising at least 90%, 91%, 92%, 93%, 94%, 95%, 96%, 97%, 98% or 99% sequence identity to SEQ ID NO: 3, and said LsAAP2B gene encodes a LsAAP2B protein of SEQ ID NO: 6 or a protein comprising at least 90%, 91%, 92%, 93%, 94%, 95%, 96%, 97%, 98% or 99% sequence identity to SEQ ID NO: 6, and wherein said mutant lsaap2a allele results in reduced expression or no expression of the LsAAP2A gene or wherein the mutant lsaap2a allele encodes a protein having a decreased function or a loss-of-function compared to the wild type LsAAP2A protein, and wherein said mutant lsaap2b allele results in reduced expression or no expression of the LsAAP2B gene or wherein the mutant lsaap2b allele encodes a protein having a decreased function or a loss-of-function compared to the wild type LsAAP2B protein.

In one aspect a plant or plant part of the species *Cucurbita pepo* is provided comprising at least one copy of a mutant allele of a gene named CpAAP2A and/or of a mutant allele of a gene named CpAAP2B, wherein said CpAAP2A gene encodes a CpAAP2A protein of SEQ ID NO: 14 or a protein comprising at least 90%, 91%, 92%, 93%, 94%, 95%, 96%, 97%, 98% or 99% sequence identity to SEQ ID NO: 14, and said CpAAP2B gene encodes a CpAAP2B protein of SEQ ID NO: 15 or a protein comprising at least 90%, 91%, 92%, 93%, 94%, 95%, 96%, 97%, 98% or 99% sequence identity to SEQ ID NO: 15, and wherein said mutant cpaap2a allele results in reduced expression or no expression of the CpAAP2A gene or wherein the mutant cpaap2a allele encodes a protein having a decreased function or a loss-of-function compared to the wild type CpAAP2A protein, and wherein said mutant cpaap2b allele results in reduced expression or no expression of the CpAAP2B gene or wherein the mutant cpaap2b allele encodes a protein having a decreased function or a loss-of-function compared to the wild type CpAAP2B protein.

Gene expression can be measured as known in the art, e.g. by measuring the mRNA transcript levels by quantitative real-time PCR (qRT-PCR). See for example Berg et al. BMC Plant Biology 2015, 15: 243, page 1-17, see page 15.

A bottle gourd plant may thus either have a mutant lsaap2a or a mutant lsaap2b allele (i.e. a single mutant allele), or both (double mutant). Likewise a *Cucurbita pepo* plant may thus either have a mutant cpaap2a or a mutant cpaap2b allele (i.e. a single mutant allele), or both (double mutant).

The embodiments described herein for the *Lagenaria siceraria* AAP2A and AAP2B mutant alleles in Bottle Gourd plants and plant parts apply in the same way to the *C. pepo* AAP2A and AAP2B mutant alleles in *Cucurbita pepo* plants and plant parts and the latter is therefore included in between brackets. Likewise, the embodiments described herein for the *Lagenaria siceraria* AAP2A mutant alleles and for the *C. pepo* AAP2A mutant alleles apply in the same way to the *Momordica charantia* AAP mutant allele in bitter gourd plants and plant parts, even if not explicitly described.

In one aspect, the bottle gourd (*C. pepo*) plant comprising a single mutant lsaap2a allele (cpaap2a allele) in homozygous form shows reduced susceptibility to the oomycete *Pseudoperonospora cubensis* compared to the susceptible control plant lacking any of the mutant alleles (i.e. comprising wild type alleles) and the same is expected for a plant comprising a single mutant lsaap2b allele (cpaap2b allele) in homozygous form. In a plant comprising a double mutant allele the susceptibility to *P. cubensis* may be even reduced more strongly than in the single mutant plant. This can be tested by combining mutant lsaap2a allele (cpaap2a allele) and the mutant lsaap2b allele (cpaap2b allele) in a single plant, either by directly generating double mutants in a single plant (using e.g. CRISPR constructs with multiple single guide RNAs, sgRNAs, targeting both genes) or by crossing plants comprising single mutant alleles with each other and selecting progeny comprising both mutant alleles.

Thus, in a further aspect the mutant lsaap2a and/or lsaap2b (cpaap2a and/or cpaap2b) allele confers reduced susceptibility to the oomycete *Pseudoperonospora cubensis* at least when the mutant lsaap2a and/or lsaap2b (cpaap2a and/or cpaap2b) allele is in homozygous form compared to a plant or plant part homozygous for the wild type allele of the LsAAP2A and LsAAP2B (CpAAP2A and CpAAP2B) gene. The reduced susceptibility can be measured in a disease assay by e.g. assessing the *P. cubensis* induced symptom development, e.g. leaf yellowing/chlorosis and/or sporulation, at one or more time points after inoculation, in a plant line or variety comprising the mutant lsaap2a and/or lsaap2b (cpaap2a and/or cpaap2b) allele in homozygous form, compared to a susceptible control plant line or variety comprising the wild type LsAAP2A and LsAAP2B (CpAAP2A and CpAAP2B) allele in homozygous form when grown under the same conditions. The plant line comprising the mutant lsaap2a and/or lsaap2b (cpaap2a and/or cpaap2b) allele in homozygous would be considered to have reduced susceptibility when the average symptom development, e.g. leaf yellowing/chlorosis and/or average sporulation, is significantly less compared to the average leaf yellowing/chlorosis and/or average sporulation in the susceptible control. See Examples for a suitable disease assay for assessing leaf yellowing/chlorosis and sporulation in cucumber. This assay can be adapted to other cucurbit species or a method known in the art can be used.

An endogenous Bottle Gourd LsAAP2A gene (or an LsAAP2A allele thereof) is a gene (or allele) encoding a (wild type, functional) LsAAP2A protein which comprises at least 90% or more sequence identity to the LsAAP2A protein of SEQ ID NO: 3. It comprises an Aa_trans domain as shown in FIG. 1. The presence of an Aa_trans domain can be checked by analysing the amino acid sequence in InterPro, at ebi.ac.uk/interpro/search/sequence-search. An endogenous Bottle Gourd LsAAP2B gene (or an LsAAP2B allele thereof) is a gene (or allele) encoding a (wild type, functional) LsAAP2B protein which comprises at least 90% or more sequence identity to the LsAAP2B protein of SEQ ID NO: 6. It comprises an Aatrans domain as shown in FIG. 2. The presence of an Aa_trans domain can be checked by analysing the amino acid sequence in InterPro, at ebi.ac.uk/interpro/search/sequence-search.

An endogenous *Cucurbita pepo* CpAAP2A gene (or an CpAAP2A allele thereof) is a gene (or allele) encoding a (wild type, functional) CpAAP2A protein which comprises at least 90% or more sequence identity to the CpAAP2A protein of SEQ ID NO: 14. It comprises an Aa_trans domain as shown in FIG. 3. The presence of an Aa_trans domain can be checked by analysing the amino acid sequence in InterPro, at ebi.ac.uk/interpro/search/sequence-search. An endogenous *Cucurbita pepo* CpAAP2B gene (or an CpAAP2B allele thereof) is a gene (or allele) encoding a (wild type, functional) CpAAP2B protein which comprises at least 90% or more sequence identity to the CpAAP2B protein of SEQ ID NO: 15. It comprises an Aa_trans domain as shown in FIG. 3. The presence of an Aa_trans domain can be checked by analysing the amino acid sequence in InterPro, at ebi.ac.uk/interpro/search/sequence-search.

An endogenous bitter gourd McAAP gene (or an McAAP allele thereof) is a gene (or allele) encoding a (wild type, functional) McAAP protein which comprises at least 90% or more sequence identity to the bitter gourd McAAP protein of SEQ ID NO: 13. It comprises an Aa_trans domain as shown in FIG. 3. The presence of a Aa_trans domain can be checked by analysing the amino acid sequence in InterPro, at ebi.ac.uk/interpro/search/sequence-search.

In the plant or plant part comprising said mutant lsaap2a and/or lsaap2b (cpaap2a and/or cpaap2b) allele, said mutant lsaap2a and/or lsaap2b (cpaap2a and/or cpaap2b) allele results in reduced expression or no expression of the (endogenous, wild type) LsAAP2A or LsAAP2B (CpAAP2A or CpAAP2B) gene, respectively, or said mutant lsaap2a and/or lsaap2b (cpaap2a and/or cpaap2b) allele encodes a protein having a decreased function or a loss-of-function compared to the wild type LsAAP2A or LsAAP2B (CpAAP2A or CpAAP2B) protein, respectively, i.e. said mutant allele encodes a mutant lsaap2a or lsaap2b (cpaap2a or cpaap2b) protein.

Thus, as a result of the mutation in the endogenous LsAAP2A and/or LsAAP2B (CpAAP2A and/or CpAAP2B) allele, there is either less or even no wild type LsAAP2A or LsAAP2B (CpAAP2A or CpAAP2B) mRNA transcript being produced by the mutant allele (e.g. if the mutation is in a regulatory sequence of the endogenous allele) in the plant cell and plant, or as a result of the mutation a mutant LsAAP2A or LsAAP2B (CpAAP2A or CpAAP2B) protein is produced by the mutant allele, e.g. comprising one or more amino acids replaced, deleted or inserted compared to the functional wild type protein, thereby leading to a reduced function or loss of function of the (mutant) lsaap2a or lsaap2b (cpaap2a or cpaap2b) protein. And consequently, when the mutant lsaap2a and/or lsaap2b (cpaap2a and/or cpaap2b) allele is in homozygous form in the genome of the plant, the plant will be at least partially resistant against downy mildew/less susceptible to *P. cubensis* than the plant comprising two functional/wild type LsAAP2A (CpAAP2A) alleles and two functional/wild type LsAAP2B (CpAAP2B) alleles. The same applies to a mutant mcaap allele.

No expression of the mutant lsaap2a or lsaap2b (cpaap2a or cpaap2b) allele, or mcaap allele, means that no transcript (mRNA) is being transcribed from the mutant allele, due to e.g. a mutation in the promoter sequence being present. So if the mutant allele is in homozygous form, the wild type mRNA, encoding the functional protein will not be present in plant tissue in which it is otherwise present in the susceptible control (comprising the wild type alleles), such as roots, stems, hypocotyl, cotyledon, leaf and/or flower. An allele having no expression may also be referred to as a knock-out allele herein.

Reduced (or decreased) expression of the mutant lsaap2a (cpaap2a) allele or of the mutant lsaap2b (cpaap2b) allele or a mutant mcaap allele means for example that only 50%, or less, of the amount of transcript (mRNA) is transcribed from the mutant allele compared to the wild type allele, or only equal to or less than 40%, 30%, 20%, 10%, or 5% of the amount of transcript (mRNA) is transcribed from the mutant allele compared to the wild type allele. In other words, when the mutant allele is in homozygous form, the wild type mRNA, encoding the functional protein will be present in plant tissue in which it is otherwise present, such as leaves, roots, hypocotyl, cotyeldons or stems, but at a significantly lower amount than in a plant which is homozygous for the wild type allele. This will result in significantly less functional wild type protein being present, which in turn results in reduced susceptibility of the plant. An allele having reduced expression may also be referred to as a knock-down allele herein.

The decrease in the expression of the lsaap2a (cpaap2a) or lsaap2b (cpaap2b) or mcaap allele can, for example, be determined by measuring the quantity of RNA transcripts (e.g. mRNA), e.g. by qRT-PCR. Similarly, the decrease in the amount of LsAAP2A (CpAAP2A) or LsAAP2B (CpAAP2B) protein, or McAAP protein, can, for example, be determined by immunological methods such as Western blot analysis, ELISA (Enzyme Linked Immuno Sorbent Assay) or RIA (Radio Immune Assay). Here, a decrease preferably means a reduction in the amount of LsAAP2A (CpAAP2A) proteins or LsAAP2B (CpAAP2B), or McAAP protein by at least 50%, in particular by at least 70%, or by at least 85% and particularly by at least 95%.

In another embodiment the plant or plant part comprises a mutant lsaap2a (cpaap2a) allele, wherein the protein encoded by the mutant lsaap2a (cpaap2a) allele comprising one or more amino acids replaced, inserted or deleted compared to the LsAAP2A (CpAAP2A) wild type protein of SEQ ID NO: 3 (SEQ ID NO: 14) (or a functional variant thereof comprising at least 90% sequence identity to SEQ ID NO: 3/SEQ ID NO: 14), especially one or more amino acids replaced, inserted and/or deleted in the conserved Amino Acid Transporter Domain at amino acid 20 to 453 of SEQ ID NO: 3 (SEQ ID NO: 14) or in an Amino Acid Transporter Domain comprising at least 95%, 96%, 97%, 98% or 99% sequence identity to amino acid 20 to 453 of SEQ ID NO: 3 (SEQ ID NO: 14). Such a protein can have a reduced activity or no activity in vivo.

In another embodiment the plant or plant part comprises a mutant lsaap2b (cpaap2b) allele, wherein the protein encoded by the mutant lsaap2b (cpaap2b) allele comprising one or more amino acids replaced, inserted or deleted compared to the LsAAP2B (CpAAP2B) wild type protein of SEQ ID NO: 6 (SEQ ID NO: 15) (or a functional variant thereof comprising at least 90% sequence identity to SEQ ID NO: 6/SEQ ID NO: 15), especially one or more amino acids replaced, inserted and/or deleted in the conserved Amino Acid Transporter Domain at amino acid 20 to 453 of SEQ ID NO: 6 (at amino acids 20 to 445 of SEQ ID NO: 15) or in an Amino Acid Transporter Domain comprising at least 95%, 96%, 97%, 98% or 99% sequence identity to amino acid 20 to 453 of SEQ ID NO: 6 (to amino acids 20 to 445 of SEQ ID NO: 15). Such a protein can have a reduced activity or no activity in vivo.

In one embodiment the plant or plant part comprises both of the above mutant alleles (double mutant), i.e. lsaap2a and lsaap2b (or cpaap2a and cpaap2b).

In one aspect, the bottle gourd (or *C. pepo*) plant or plant part comprises a mutant lsaap2a (cpapp2a) allele and/or a mutant lsaap2b (cpapp2b) allele, wherein the mutant lsaap2a (cpapp2a) allele encodes a protein that is truncated compared to the wild type LsAAP2A (CpAAP2A) protein and/or the mutant lsaap2b (cpapp2b) allele encodes a protein that is truncated compared to the wild type LsAAP2B (CpAAP2B) protein. The truncated protein may comprise additional amino acids, for example a frame shift mutation may result in the truncated protein comprising an amino acid sequence which is different from the amino acid sequence of the wild type protein. A truncated protein can have a reduced activity or even no activity in vivo, especially when all or part of the Aa_trans domain is missing and/or is replaced by different amino acids. Thus in one aspect the mutant lsaap2a (cpapp2a) allele encodes a protein that is truncated compared to the wild type LsAAP2A (CpAAP2A) protein and/or the mutant lsaap2b (cpapp2b) allele encodes a protein that is truncated compared to the wild type LsAAP2B (CpAAP2B) protein, wherein at least one, two, three, four, 5, 6, 7, 8, 9, 10, 15, 20, 30, 40, 50 or more amino acids of the Aa_trans domain are missing or are replaced by different amino acids compared to the wild type protein. In one aspect at least 13, 14, 15, 20, 30, 40, 50 or more amino acids of the C-terminal end of the LsAAP2A or LsAAP2B protein (or CpAAP2A or CpAAP2B protein) are missing or are replaced by one or more different amino acids compared to the wild type protein. The same applies to McAAP.

The 2-dimensionl analysis showed that a large part of the LsAAP2A, LsAAP2B, CpAAP2A, CpAAP2B and McAAP protein consists of the Aa_trans domain. 3-dimensional analysis predicts that both the LsAAP2A protein and the LsAAP2B protein consists of 67% helix structure and 32% loop structures (coils), and the CpAAP2A protein consist of 67% helix structure and 32% loop structures (coils) and the CpAAP2B protein consist of 68% helix structure and 31% loop structures (coils). The McAAP protein consists of 67% helix structure and 32% loop structure. This means that any amino acid insertion, deletion or replacement, especially of one or more amino acids in the Aa_trans domain, will likely change the 3-dimensional structure of the protein and reduce its in vivo function or even abolish its in vivo function. For example, a mutation which results in a change of a codon into a STOP codon, will result in a truncated protein.

In one aspect the bottle gourd plant comprises a mutant lsaap2a and/or lsaap2b allele in homozygous or heterozygous form, wherein the encoded protein lacks the 95 C-terminal amino acids of SEQ ID NO: 3 or SEQ ID NO: 6, respectively, or of a protein comprising at least 90% sequence identity to SEQ ID NO: 3 or to SEQ ID NO: 6, respectively. For example a mutation in the codon encoding amino acid number 372 (W, Tryptophan) to a stop codon, leads to a truncation of the LsAAP2A (or LsAAP2B) protein, whereby the protein comprises amino acids 1 to 371 of SEQ ID NO: 3 (or SEQ ID NO: 6) and lacks amino acids 372 to 466 of SEQ ID NO: 3 (or SEQ ID NO: 3), i.e. the 95 C-terminal amino acids are missing. As these 95 C-terminal amino acids comprise 82 amino acids of the AA_trans domain, the protein has reduced function or more likely even loss-of-function in vivo. The bottle gourd plant comprising this mutant allele in homozygous form has a reduced susceptibility to *P. cubensis*. This mutant allele (as well as any other mutant allele described herein) can be induced e.g. in elite breeding lines, or it can also be a natural mutant allele, introgressed into cultivated bottle gourd.

In one aspect the *C. pepo* plant comprises a mutant cpaap2a and/or cpaap2b allele in homozygous or heterozygous form, wherein the encoded protein lacks the 95 C-terminal amino acids of SEQ ID NO: 14 or SEQ ID NO: 15, respectively, or of a protein comprising at least 90% sequence identity to SEQ ID NO: 14 or to SEQ ID NO: 15, respectively. For example a mutation in the codon encoding amino acid number 372 of SEQ ID NO: 14 or 364 of SEQ ID NO: 15 (W, Tryptophan) to a stop codon, leads to a truncation of the CpAAP2A (or CpAAP2B) protein, whereby the protein comprises amino acids 1 to 371 of SEQ ID NO: 14 (or amino acids 1 to 363 of SEQ ID NO: 15) and lacks amino acids 372 to 466 of SEQ ID NO: 14 (or lacks amino acids 364 to 458 SEQ ID NO: 15), i.e. the 95 C-terminal amino acids are missing. As these 95 C-terminal amino acids comprise 82 amino acids of the AA_trans domain, the protein has reduced function or more likely even loss-of-function in vivo. The *C. pepo* plant comprising this mutant allele in homozygous form has a reduced susceptibility to *P. cubensis*. This mutant allele (as well as any other mutant allele described herein) can be induced e.g. in elite breeding lines, or it can also be a natural mutant allele, introgressed into cultivated *C. pepo*.

Thus, in one aspect a mutant lsaap2a (cpaap2a) and/or mutant lsaap2b (cpaap2b) allele is provided, wherein the allele is a natural mutant allele obtained (obtainable) from an accession of a wild bottle gourd (or wild *C. pepo*) plant or wild relative of bottle gourd (or *C. pepo*) plant. The accession in which the natural mutant allele is found may have non-desirable characteristics. The accession can, therefore, be used as a donor to backcross the mutant allele into cultivated bottle gourd (or *C. pepo*). Preferably the mutant allele is backcrossed into cultivated bottle gourd (or *C. pepo*) having good agronomic characteristics. Such plants and plant parts are encompassed herein, as are methods for identifying natural mutant alleles and/or introgressing them into cultivated plants.

A mutant lsaap2a allele encoding a truncated LsAAP2A protein may, thus be an allele which encodes a protein that lacks at least 13, 14, 15, 20, 30, 40, 50, 60, 70, 80, 90, 95, 100, 120, 130, 140, 150, 160, 170, 180, 190, 200, 250, 300, 350, 400 or even more of the C-terminal amino acids compared to the wild type LsAAP2A protein of SEQ ID NO: 3, or of a variant comprising at least 90%, 91%, 92%, 93%, 94%, 95%, 96%, 97%, 98% or 99% sequence identity to SEQ ID NO: 3.

A mutant lsaap2b allele encoding a truncated LsAAP2B protein may, thus be an allele which encodes a protein that lacks at least 13, 14, 15, 20, 30, 40, 50, 60, 70, 80, 90, 100, 120, 130, 140, 150, 160, 170, 180, 190, 200, 250, 300, 350, 400 or even more of the C-terminal amino acids compared to the wild type LsAAP2B protein of SEQ ID NO: 6, or of a variant comprising at least 90%, 91%, 92%, 93%, 94%, 95%, 96%, 97%, 98% or 99% sequence identity to SEQ ID NO: 6.

A mutant cpaap2a allele encoding a truncated CpAAP2A protein may, thus be an allele which encodes a protein that lacks at least 13, 14, 15, 20, 30, 40, 50, 60, 70, 80, 90, 95, 100, 120, 130, 140, 150, 160, 170, 180, 190, 200, 250, 300, 350, 400 or even more of the C-terminal amino acids compared to the wild type CpAAP2A protein of SEQ ID NO: 14, or of a variant comprising at least 90%, 91%, 92%, 93%, 94%, 95%, 96%, 97%, 98% or 99% sequence identity to SEQ ID NO: 14.

A mutant cpaap2b allele encoding a truncated CpAAP2B protein may, thus be an allele which encodes a protein that lacks at least 13, 14, 15, 20, 30, 40, 50, 60, 70, 80, 90, 100, 120, 130, 140, 150, 160, 170, 180, 190, 200, 250, 300, 350, 400 or even more of the C-terminal amino acids compared to the wild type CpAAP2B protein of SEQ ID NO: 15, or of a variant comprising at least 90%, 91%, 92%, 93%, 94%, 95%, 96%, 97%, 98% or 99% sequence identity to SEQ ID NO: 15.

A mutant mcaap allele encoding a truncated McAAP protein may, thus be an allele which encodes a protein that lacks at least 13, 14, 15, 20, 30, 40, 50, 60, 70, 80, 90, 100, 120, 130, 140, 150, 160, 170, 180, 190, 200, 250, 300, 350, 400 or even more of the C-terminal amino acids compared to the wild type McAAP protein of SEQ ID NO: 13, or of a variant comprising at least 90%, 91%, 92%, 93%, 94%, 95%, 96%, 97%, 98% or 99% sequence identity to SEQ ID NO: 13.

Thus in one aspect the mutant allele results in a truncated LsAAP2A protein or a truncated LsAAP2B protein being produced, which truncated protein has decreased function or loss-of-function. In another aspect the mutant allele results in a truncated CpAAP2A protein or a truncated CpAAP2B protein being produced, which truncated protein has decreased function or loss-of-function. In yet another aspect the mutant allele results in a truncated McAAP protein being produced, which truncated protein has decreased function or loss-of-function. A truncation may for example result in the loss of the C-terminal end (carboxyl terminal end) of the protein, whereby part or all of the Aa_trans domain is absent. For example only the N-terminal part (amino terminal part) of the protein may still be present. Mutant alleles which express a truncated LsAAP2A protein or a truncated LsAAP2B protein, or a truncated CpAAP2A protein or a truncated CpAAP2B, or a truncated McAAP protein, can be induced whereby, for example, a codon in one of the exons is changed into a premature stop codon or splice-site mutations or frame-shift mutations can also lead to premature stop codons and truncated proteins.

In another aspect the mutant allele results in a mutant LsAAP2A or LsAAP2B protein (or CpAAP2A or CpAAP2B protein, or McAAP protein), which comprises one or more amino acids inserted, replaced and/or deleted compared to the wild type protein. As mentioned, especially insertion, replacement and/or deletion of one or more amino acids in the Aa_trans domain will result in a mutant protein that has decreased function or loss of function, and will, in homozygous form in the watermelon plant, reduce susceptibility to *P. cubensis.*

Whether the insertion, replacement and/or deletion of one or more amino acids, or a truncation or mutant allele not expressed or having reduced expression as described elsewhere herein, actually results in a reduced susceptibility in vivo can be tested by carrying out a disease assay for a plant comprising the mutant allele (or double mutant) in homozygous form.

Optionally the increase in free amino acids following *P. cubensis* infection can be compared between the plant comprising the mutant lsaap2a and/or lsaap2b (cpaap2a and/or cpaap2b) allele and the susceptible control comprising the wild type alleles (WT). A reduced increase in free amino acids, especially in Ala, Gly, Val, Leu, Ile, Thr, Ser, Pro and/or Gln compared to the increase in the susceptible control (comprising functional wild type AAP2A and AAP2B alleles) indicates that the mutant allele has reduced function or a loss of function in vivo.

In yet another aspect the mutant allele results in reduced expression or no expression of the allele and thus reduced amounts or no protein of the wild type LsAAP2A or LsAAP2B (CpAAP2A or CpAAP2B) protein being produced in the plant or plant part. For example, the promoter or another regulatory element of the LsAAP2A or LsAAP2B (CpAAP2A or CpAAP2B) allele may be comprise one or more nucleotides inserted, deleted and/or replaced.

Thus, a mutant allele of a LsAAP2A (CpAAP2A) protein-encoding gene and/or LsAAP2B (CpAAP2B) protein-encoding gene causes a plant to have reduced susceptibility to *P. cubensis*, at least when the plant is homozygous for the mutant allele. Concerning the embodiments of the invention, the mutation in the mutant allele of a LsAAP2A (CpAAP2A) protein-encoding gene or LsAAP2B (CpAAP2B) protein encoding gene (i.e. in the mutant lsaap2a allele and/or lsaap2b allele or in the mutant cpaap2a and/or cpaap2b allele) can be any mutation, including one or more deletions, truncations, insertions, point mutations, nonsense mutations, missense or non-synonymous mutations, splice-site mutations, frame shift mutations and/or mutations in regulatory sequences (for example in the promoter sequence). In one aspect the mutation in the mutant lsaap2a allele and/or lsaap2b (cpaap2a allele and/or cpaap2b) allele is a point mutation. The mutation can occur in a DNA sequence comprising the coding sequence of a LsAAP2A (CpAAP2A) protein-encoding gene or LsAAP2B (CpAAP2A) protein-encoding gene, or in a RNA sequence encoding a LsAAP2A (CpAAP2A) protein or LsAAP2B (CpAAP2B) protein, or it can occur in the amino acid molecule of the LsAAP2A (CpAAP2A) or LsAAP2B (CpAAP2B) protein.

Concerning a DNA sequence of LsAAP2A (CpAAP2A) protein-encoding gene or LsAAP2A (CpAAP2A) protein-encoding gene, the mutation can occur in the coding sequence (cds, composed of the exons) or it can occur in non-coding sequences like 5'- and 3'-untranslated regions, introns, promoters, enhancers etc. In respect to RNA encoding a LsAAP2A (CpAAP2A) protein or LsAAP2A (CpAAP2A) protein, the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted or deleted in the conserved Aa_trans domain. For example, truncation of the protein to cause deletion of the Aa_trans domain, or part thereof, will result in a loss of function or decrease of function of the protein.

A further embodiment of the invention therefore concerns bottle gourd (or *C. pepo*) plant cells or plants according to the invention comprising a mutant allele of a LsAAP2A (CpAAP2A) protein-encoding gene and/or of a LsAAP2B (CpAAP2B) protein-encoding gene, characterized in that the mutant lsaap2a (cpaap2a) allele and/or mutant lsaap2b (cpaap2b) allele comprises or effects one or more of the mutations selected from the group consisting of a) a deletion, truncation, insertion, point mutation, non-sense mutation, missense or non-synonymous mutation, splice-site mutation, frame shift mutation in the genomic sequence;
b) a mutation in one or more regulatory sequences;
c) a deletion, truncation, insertion, point mutation, non-sense mutation, missense or non-synonymous mutation, splice-site mutation, frame shift mutation in the coding sequence;
d) a deletion, truncation, insertion, point mutation, non-sense mutation, missense or non-synonymous mutation, splice-site mutation, frame shift mutation in the pre-mRNA or mRNA; and/or
e) a deletion, truncation, insertion or replacement of one or more amino acids in the LsAAP2A (CpAAP2A) or LsAAP2B (CpAAP2B) protein.

A different embodiment of the invention concerns bottle gourd (or *C. pepo*) plant cells, plant parts or plants comprising or synthesising an mRNA encoding a LsAAP2A (CpAAP2A) protein and/or LsAAP2B (CpAAP2B) protein, wherein the mRNA encoding a LsAAP2A (CpAAP2A) protein or LsAAP2B (CpAAP2B) protein has one or more mutations selected from the group consisting of a) a deletion mutation;
b) a missense or non-synonymous mutation;
c) a frame shift mutation; and/or
d) a non-sense mutation.

In another embodiment of the invention, plant cells or plants according to the invention comprise or synthesise an mRNA encoding a LsAAP2A protein and/or LsAAP2B (CpAAP2A protein and/or CpAAP2B) protein having one or more mutations, wherein the mRNA is transcribed from a mutant allele of a LsAAP2A (CpAAP2A) protein-encoding gene and/or from a mutant allele of a LsAAP2B (CpAAP2B) protein-encoding gene. Comprised by these embodiments of the invention are plant cells, plant parts or plants according to the invention comprising or synthesising an mRNA transcribed from a mutant allele of a LsAAP2A (CpAAP2A) protein-encoding gene and/or LsAAP2B (CpAAP2B) protein encoding gene, characterized in that the mRNA comprises a deletion mutation and/or a missense or non-synonymous mutation and/or a frame shift mutation and/or a non-sense mutation, compared to the corresponding (DNA) coding sequence of the mutant allele of the LsAAP2A or LsAAP2B (CpAAP2A or CpAAP2B) protein-encoding gene from which the mRNA is transcribed. Thus, in one aspect any mutation which affects pre-mRNA splicing is encompassed, i.e. which modifies the normal pre-mRNA splicing process, thereby leading to a different mRNA molecule.

An "mRNA coding sequence" shall have the common meaning herein. An mRNA coding sequence corresponds to the respective DNA coding sequence of a gene/allele apart from that thymine (T) is replaced by uracil (U).

In one aspect the plant or plant part is homozygous for a mutant lsaap2a (cpaap2a) allele and/or for a mutant lsaap2b (cpaap2b) allele described herein. Because both the LsAAP2A gene and the LsAAP2B gene (and the CpAAP2A gene and the CpAAP2B) are deemed to be recessive, the reduction in susceptibility is seen phenotypically when the plant is homozygous for one or both of the mutant alleles, although it is not excluded that an effect may also be seen when the plant is heterozygous for one or both mutant alleles.

In one aspect the mutant lsaap2a and/or lsaap2b allele is an induced mutant allele, while in a different aspect the mutant lsaap2a and/or lsaap2b allele is a "natural allele" or "natural mutant allele" introgressed into cultivated bottle gourd by e.g. backcrossing.

In one aspect the mutant cpaap2a and/or cpaap2b allele is an induced mutant allele, while in a different aspect the mutant cpaap2a and/or cpaap2b allele is a "natural allele" or "natural mutant allele" introgressed into cultivated *C. pepo* by e.g. backcrossing.

In one aspect the mutant mcaap allele is an induced mutant allele, while in a different aspect the mutant mcaap allele is a "natural allele" or "natural mutant allele" introgressed into cultivated bitter gourd by e.g. backcrossing.

Mutant alleles can be generated by methods known in the art, such as chemical mutagenesis (e.g. EMS treatment), radiation mutagenesis (UV, gamma rays etc.), targeted mutagenesis, such as Crispr/Cas9 or TALENS.

Suitable chemical mutagens include ethyl methanesulfonate (EMS), methylmethane sulfonate (MMS), N-ethyl-N-nitrosurea (ENU), trimethylamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitrosoguanidine (MNNG), nitro so guanidine, 2-aminopurine, 7,12-dimethylbenz(a)anthracene (DMBA), ethylene oxide, hexamethylphosphoramide, bisulfan, diepoxyalkanes, diepoxyoctrane (DEO), diepoxybutane (DEB), 2-methoxy-6-choloro9[3-ethyl-2-chloro-ethyl]aminopropylamine]acridine dihydrochloride (ICR-170), and formaldehyde. Suitable radiation is UV radiation or radioactive radiation.

Biotechnological methods for introducing mutations into a desired gene/allele of a plant cell or plant are known in the art. Therefore, mutant alleles of a LsAAP2A and/or LsAAP2B protein-encoding gene (or CpAAP2A and/or CpAAP2B protein-encoding gene, or McAAP) can be produced in plant cells or plants by using these methods. Examples for such technologies are in particular mutagenesis techniques or enzymes which induce double stranded DNA breaks (double stranded DNA break inducing enzyme (DSBI)) in the genome of plants. Known and practised technologies are rare-cleaving endonucleases and custom-tailored rare-cleaving endonucleases including but not limited to homing endonucleases, also called meganucleases, transcription activator-like effectors fused to the catalytic domain of a nuclease (TALENs) and so-called CRISPR systems. CRISPR systems is used broadly herein, and does not only encompass the use of the Cas9 nuclease (Crispr/Cas9 system), but also other Crispr systems e.g. using other nucleases, such as Cpf1. These techniques can also be referred to as targeted genome editing techniques or gene editing techniques or targeted mutagenesis techniques.

Thus, technologies such as mutagenesis or targeted genome editing techniques are eligible for introducing a mutation into genes in plant cells or plants. Therefore, plant cells and plants according to the invention having a mutant allele of a LsAAP2A and/or LsAAP2B protein-encoding gene (or CpAAP2A and/or CpAAP2B protein-encoding gene, or McAAP), wherein the mutation into the mutant allele was introduced by genome editing techniques, e.g. using rare-cleaving endonucleases or custom-tailored rare-cleaving endonucleases, are also an embodiment of the invention. Concerning custom-tailored rare-cleaving endonucleases the mutation in the mutant allele of LsAAP2A and/or LsAAP2B protein (or CpAAP2A and/or CpAAP2B protein) has preferably been introduced by a meganuclease, a TALENs or a CRISPR system.

Thus, in one aspect the mutant lsaap2a and/or lsaap2b (cpaap2a and/or cpaap2b) alleles are induced mutants, e.g. induced in a breeding line, an inbred line or variety of cultivated plants of bottle gourd (or *C. pepo*) or in one aspect the mutant alleles are induced in wild bottle gourd (or wild *C. pepo*) or wild relatives thereof (and the induced mutant alleles can then be backcrossed into cultivated bottle gourd or cultivated *C. pepo*). In one aspect the mutant alleles are generated by mutagenesis (e.g. chemical or radiation mutagenesis) or by targeted mutagenesis, especially using the CRISPR system (e.g. Crispr/Cas9 or Crispr/Cpf1 or other nucleases). In one aspect the cultivated plant comprising the mutant lsaap2a and/or lsaap2b (cpaap2a and/or cpaap2b) alleles is not a transgenic plant, i.e. non transgenic progeny are selected which do not comprise the CRISPR construct.

As mentioned, mutant alleles can also evolve naturally in populations of wild bottle gourd or wild *C. pepo* or wild bitter gourd, or wild relatives of a species. In one aspect the mutant lsaap2a and/or lsaap2b (cpaap2a and/or cpaap2b) alleles are natural mutant alleles, which have been introgressed into cultivated bottle gourd (or *C. pepo*). The wild type allele found in cultivated plant is then replaced with the natural mutant allele, i.e. by meitotic recombination between homologous chromosomes. Wild accessions can be screened for the presence of such natural mutant alleles, and backcrossing to cultivated plants can be used to introgress the natural mutant allele into the cultivated genome. Such methods and plants produced thereby, comprising one or more introgressions, are encompassed herein.

Thus in one aspect a plant or plant part of the species *Lagenaria siceraria* is provided, comprising an introgression fragment from a wild plant of the species or wild relative of the species, said introgression fragment comprises a mutant allele of a gene named LsAAP2A, said gene encodes a LsAAP2A protein of SEQ ID NO: 3 or a protein comprising at least 90%, 91%, 92%, 93%, 94% or 95% sequence identity to SEQ ID NO: 3, and/or a mutant allele of a gene named LsAAP2B, said gene encoding a LsAAP2B protein of SEQ ID NO: 6 or a protein comprising at least 90%, 91%, 92%, 93%, 94% or 95% sequence identity to SEQ ID NO: 6, wherein said mutant lsaap2a and/or lsaap2b allele results in reduced expression or no expression of the mutant allele or encodes a protein having a decreased function or a loss-of-function compared to the wild type protein.

In one aspect the introgression fragment comprises a natural mutant allele. In another aspect the introgression fragment comprises an induced mutant allele.

In one aspect a plant or plant part of the species *Cucurbita pepo* is provided, comprising an introgression fragment from a wild plant of the species or wild relative of the species, said introgression fragment comprises a mutant allele of a gene named CpAAP2A, said gene encodes a CpAAP2A protein of SEQ ID NO: 14 or a protein comprising at least 90%, 91%, 92%, 93%, 94% or 95% sequence identity to SEQ ID NO: 14, and/or a mutant allele of a gene named CpAAP2B, said gene encoding a CpAAP2B protein of SEQ ID NO: 15 or a protein comprising at least 90%, 91%, 92%, 93%, 94% or 95% sequence identity to SEQ ID NO: 15, wherein said mutant cpaap2a and/or cpaap2b allele results in reduced expression or no expression of the mutant allele or encodes a protein having a decreased function or a loss-of-function compared to the wild type protein.

In one aspect the introgression fragment comprises a natural mutant allele. In another aspect the introgression fragment comprises an induced mutant allele.

In a further aspect a plant or plant part of the species *Momordica charantia* is provided, comprising an introgression fragment from a wild plant of the species or wild relative of the species, said introgression fragment comprises a mutant allele of a gene named McAAP, said gene encodes a McAAP protein of SEQ ID NO: 13 or a protein comprising at least 90%, 91%, 92%, 93%, 94% or 95% sequence identity to SEQ ID NO: 13, wherein said mutant mcaap allele results in reduced expression or no expression of the mutant allele or encodes a protein having a decreased function or a loss-of-function compared to the wild type protein.

In one aspect wild *Lagenaria siceraria* plants, or wild relatives of *Lagenaria siceraria* are screened for the presence of a natural mutant lsaap2a or lsaap2b allele. This can be done by e.g. analysing (directly or indirectly) the genomic DNA, mRNA (or cDNA) or protein of the LsAAP2A or LsAAP2B gene, using e.g. PCR methods or other molecular methods known in the art, such as sequencing, etc. whereby the presence of a mutant lsaap2a or lsaap2b allele can be determined. The wild *Lagenaria siceraria* plants or wild relatives of *Lagenaria siceraria* may be CGN accessions, PI accessions (Plant Introductions), or accessions from various seed bank collections. Once an accession is identified to comprise a mutant lsaap2a or lsaap2b allele, the accession can be crossed to cultivated *Lagenaria siceraria*, and the mutant allele can be introgressed into the genome of cultivated *Lagenaria siceraria* by e.g. backcrossing. The cultivated *Lagenaria siceraria* introgression line is preferably selfed one or more times to ensure the mutant allele is in homozygous form and the line can then be tested for reduced susceptibility to *P. cubensis* compared to e.g. the original cultivated *Lagenaria siceraria* (e.g. the recurrent parent) comprising the wild type, functional LsAAP2A and LsAAP2B alleles in homozygous form.

Also encompassed herein is a method for identifying a natural mutant lsaap2a and/or a natural mutant lsaap2b allele. The method involves determining whether a wild *Lagenaria siceraria* or wild relative of *Lagenaria siceraria* comprises a natural mutant allele and optionally transferring the natural mutant allele into cultivated *Lagenaria siceraria* by traditional breeding techniques. Wild plant accessions are generally very heterogenous and also may comprise various other genes which affect downy mildew resistance. The effect of the mutant allele on the susceptibility of the plant will be difficult to assess in the wild accession and the mutant allele is preferably first transferred into a breeding line, preferably a breeding line which is susceptible to downy mildew. In one embodiment therefore a method for transferring a natural mutant lsaap2a and/or a natural mutant lsaap2b allele from a wild *Lagenaria siceraria* plant into a cultivated *Lagenaria siceraria* plant is provided, comprising a) identifying or providing a wild *Lagenaria siceraria* comprising a natural mutant lsaap2a and/or lsaap2b allele
b) crossing the mutant allele(s) into cultivated *Lagenaria siceraria*, preferably a cultivated *Lagenaria siceraria* line which is susceptible to *P. cubensis*, and
c) determining the effect of the mutant allele on the susceptibility to *P. cubensis.*

The same can of course be done for induced mutant alleles, which may be induced in wild *Lagenaria siceraria*, whereby in step a) one provides or identifies a wild *Lagenaria siceraria* comprising an induced mutant allele. The method may then be preceded by a step wherein mutations are induced.

In one aspect wild *Cucurbita pepo* plants, or wild relatives of *Cucurbita pepo* are screened for the presence of a natural mutant cpaap2a or cpaap2b allele. This can be done by e.g. analysing (directly or indirectly) the genomic DNA, mRNA (or cDNA) or protein of the CpAAP2A or CpsAAP2B gene, using e.g. PCR methods or other molecular methods known in the art, such as sequencing, etc. whereby the presence of a mutant cpaap2a or cpaap2b allele can be determined. The wild *Cucurbita pepo* plants or wild relatives of *Cucurbita pepo* may be CGN accessions, PI accessions (Plant Introductions), or accessions from various seed bank collections. Once an accession is identified to comprise a mutant cpaap2a or cpaap2b allele, the accession can be crossed to cultivated *Cucurbita pepo*, and the mutant allele can be introgressed into the genome of cultivated *Cucurbita pepo* by e.g. backcrossing. The cultivated *Cucurbita pepo* introgression line is preferably selfed one or more times to ensure the mutant allele is in homozygous form and the line can then be tested for reduced susceptibility to *P. cubensis* compared to e.g. the original cultivated *Cucurbita pepo* (e.g. the recurrent parent) comprising the wild type, functional CpAAP2A and CpAAP2B alleles in homozygous form.

Also encompassed herein is a method for identifying a natural mutant cpaap2a and/or a natural mutant cpaap2b allele. The method involves determining whether a wild *C. pepo* or wild relative of *C. pepo* comprises a natural mutant allele and optionally transferring the natural mutant allele into cultivated *C. pepo* by traditional breeding techniques. Wild plant accessions are generally very heterogenous and also may comprise various other genes which affect downy mildew resistance. The effect of the mutant allele on the susceptibility of the plant will be difficult to assess in the wild accession and the mutant allele is preferably first transferred into a breeding line, preferably a breeding line which is susceptible to downy mildew. In one embodiment therefore a method for transferring a natural mutant cpaap2a and/or a natural mutant cpaap2b allele from a wild *C. pepo* plant into a cultivated *C. pepo* plant is provided, comprising a) identifying or providing a wild *C. pepo* comprising a natural mutant cpaap2a and/or cpaap2b allele
b) crossing the mutant allele(s) into cultivated *C. pepo*, preferably a cultivated *C. pepo* line which is susceptible to *P. cubensis*, and
c) determining the effect of the mutant allele on the susceptibility to *P. cubensis.*

The same can of course be done for induced mutant alleles, which may be induced in wild *C. pepo*, whereby in step a) one provides or identifies a wild *C. pepo* comprising an induced mutant allele. The method may then be preceded by a step wherein mutations are induced.

The same method can be applied to *Momordica charantia* and the mcaap allele.

In one aspect wild *Momordica charantia* plants, or wild relatives of *Momordica charantia* are screened for the presence of a natural mutant mcaap allele. This can be done by e.g. analysing (directly or indirectly) the genomic DNA, mRNA (or cDNA) or protein of the McAAP gene, using e.g. PCR methods or other molecular methods known in the art, such as sequencing, etc. whereby the presence of a mutant mcaap allele can be determined. The wild *Momordica charantia* plants or wild relatives of *Momordica charantia* may be CGN accessions, PI accessions (Plant Introductions), or accessions from various seed bank collections. Once an accession is identified to comprise a mutant mcaap allele, the accession can be crossed to cultivated *Momordica charantia*, and the mutant allele can be introgressed into the genome of cultivated *Momordica charantia* by e.g. backcrossing. The cultivated *Momordica charantia* introgression line is preferably selfed one or more times to ensure the mutant allele is in homozygous form and the line can then be tested for reduced susceptibility to *P. cubensis* compared to e.g. the original cultivated *Momordica charantia* (e.g. the recurrent parent) comprising the wild type, functional McAAP allele in homozygous form.

The cultivated plant described herein, comprising either an induced mutant or a natural mutant lsaap2a and/or lsaap2b allele, or cpaap2a and/or cpaap2b, or mcaap allele in its genome preferably comprises either or both mutant alleles in homozygous form, as the reduced susceptibility against *P. cubensis* is at least seen when the allele is in homozygous form. Plants comprising either or both mutant alleles in heterozygous form are also encompassed herein.

The cultivated plant comprising a mutant lsaap2a and/or lsaap2b allele, or cpaap2a and/or cpaap2b, or mcaap allele according to the invention may be of any type, e.g. it may be of one of the following types:

diploid, open pollinated, inbred line, double haploid line, male sterile line, pollinizer, rootstock, scion or F1 hybrid.

The cultivated plant preferably has good agronomic and good fruit quality characteristics. The cultivated plant is in one aspect uniform, both genetically and phenotypically. Especially fruit characteristics are uniform, e.g. regarding shape, color, fruit flesh color, brix or TSS (total soluble solids), flavour, etc. Likewise seed characteristics (i.e. characteristics of the seeds from which the plant is grown) are uniform, e.g. seed size, seed color, etc. In one aspect the fruits have an average TSS at maturity or at harvest stage of at least 4%, 5%, 6%, 7%, 8%, 9%, 10%, 11%, 12%, 13%, 14%, 15%. The average % TSS (or brix) can be measured as known in the art, e.g. using a digital hand refractometer and measuring the TSS of several fruits of a line or variety. See for example Burger et al. 2003, J American Soc Hort Science 128(4): 537-540 on page 538 at Measurement of TSS.

Also a seed is provided from which a plant or plant part according to the invention can be grown.

Further a fruit produced by a plant according to the invention is provided, wherein the fruit comprises the mutant lsaap2a and/or lsaap2b allele, or the mutant cpaap2a and/or cpaap2b allele, or the mutant mcaap allele, preferably in homozygous form.

Likewise plant parts of a plant according to the invention are provided, wherein the plant part is a cell, a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther. The plant part comprises in its genome a mutant allele of the invention, preferably in homozygous form. In one aspect the cell is a non-propagating or a non-regenerable cell. In one aspect the non-propagating or non-regenerable cell is part of a tissue or organ of the plant. In a different aspect the non-propagating or non-regenerable cell is in a cell culture or tissue culture.

Also a cell culture or a tissue culture of cells or tissues comprising in its genome a mutant allele of the invention is encompassed herein. Further a plant regenerated from such a cell or tissue culture is encompassed.

Further a vegetatively propagated plant propagated from a plant part according to the invention is provided.

Also a food or feed product comprising cells according to the invention are provided, such as parts of fruits.

In one embodiment a method of fruit production is provided, said method comprising growing a plant according to the invention, comprising a mutant lsaap2a and/or lsaap2b allele (or a mutant cpaap2a and/or cpaap2b; or a mutant mcaap allele), preferably in homozygous form, said method optionally comprising a reduced treatment with fungicides compared to a susceptible control plant, e.g. a plant comprising a wild type LsAAP2A allele and a wild type LsAAP2B allele in homozygous form (or the wild type CpAAP2A allele and a wild type CpAAP2B allele; or the wild type McAAP allele), and optionally harvesting the fruits produced by said plants. As the plant is less susceptible to *P. cubensis*, less fungicide treatment (lower amounts and/or less frequent applications of fungicides) is needed.

*P. cubensis* infects cucurbit plants in both the field and the greenhouse, therefore in the above method plants of the invention are grown either in the field or in greenhouses.

The pathogen has a high potential to become resistant to fungicides, it was for example the first oomycete with documented resistance to metalaxyl and reduced sensitivity to mancozeb. It has also been described to have developed resistance to strobulurin fungicides. Less fungicide treatment will reduce the risk of resistance developing.

As mentioned previously, mutant lsaap2a and/or lsaap2b alleles, or cpaap2a and/or cpaap2b alleles, or mcaap alleles, can be induced, i.e. the can be generated by mutating the endogenous allele in cultivated bottle gourd, or *C. pepo*, or bitter gourd seeds or plants or plant parts (or optionally in wild plants) and/or by selecting induced mutants e.g. tissue culture induced mutants or TILLING mutants.

Therefore, methods for producing and/or selecting plants having mutant lsaap2a and/or lsaap2b alleles, or mutant cpaap2a and/or cpaap2b alleles, or mutant mcaap alleles, resulting in a knock-down or knock-out of gene expression and consequently less or no wild type protein being produced, or mutant alleles encoding mutant proteins having a decreased function or loss-of-function compared to the wild type protein are encompassed herein. To generate such mutant alleles conventional mutagenic agents, like chemicals or high energy radiation (e.g. x-rays, neutron radiation, gamma radiation or UV radiation) may be used. It is also possible to generate mutant alleles by means of biotechnology methods as described above (e.g. targeted gene editing technology).

In one aspect the invention provides a method for generating and/or identifying a Lagenraria siceraria (or a *C. pepo* plant) plant comprising a mutant allele of a gene named LsAAP2A (or CpAAP2A), said gene encodes a LsAAP2A protein of SEQ ID NO: 3 (or a CpAAP2A protein of SEQ ID NO: 14) or a protein comprising at least 90%, 91%, 92%, 93%, 94% or 95% sequence identity to SEQ ID NO: 3 (SEQ ID NO: 14), comprising identifying or selecting a plant in a mutant Lagenraria siceraria population (or in a mutant *C. pepo* population), or progeny thereof obtained by selfing, comprising a mutant lsaap2a (cpaap2a) allele, or generating a mutant plant comprising a mutant lsaap2a (cpaap2a) allele using a targeted genome editing technique, such as a Crispr system (e.g. Crispr/Cas9).

In another aspect the invention provides a method for generating a *Lagenaria siceraria* plant (or *C. pepo* plant) comprising a mutant allele of a gene named LsAAP2B (or CpAAP2B), said gene encodes a LsAAP2B protein of SEQ ID NO: 6 (or a CpAAP2B protein of SEQ ID NO: 15) or a protein comprising at least 90%, 91%, 92%, 93%, 94% or 95% sequence identity to SEQ ID NO: 6 (SEQ ID NO: 15), comprising identifying or selecting a plant in a mutant *Lagenaria siceraria* population (or in a mutant *C. pepo* population), or progeny thereof obtained by selfing, comprising a mutant lsaap2b (cpaap2b) allele, or generating a *Lagenaria siceraria* plant comprising a mutant lsaap2b (cpaap2b) allele using a targeted genome editing technique, such as a Crispr system (e.g. Crispr/Cas9).

A 'mutant *Lagenaria siceraria* population' or 'population of mutant *Lagenaria siceraria* plants' refers to a plurality of *Lagenaria siceraria* seeds or plants or plant parts which have been treated with a conventional mutagenic agents, like chemicals or high energy radiation (e.g. x-rays, neutron radiation, gamma radiation or UV radiation) or progeny thereof obtained by selfing, to ensure that mutations are in homozygous form. These can be plants or seeds or plant parts of a cultivated breeding line, variety, inbred line or any plurality of cultivated plants or seeds. Alternatively these may be wild plants or wild relatives of *Lagenaria siceraria.*

Likewise a 'mutant *Cucurbita pepo* population' or 'population of mutant *Cucurbita pepo* plants' refers to a plurality of *Cucurbita pepo* seeds or plants or plant parts which have been treated with a conventional mutagenic agents, like chemicals or high energy radiation (e.g. x-rays, neutron radiation, gamma radiation or UV radiation) or progeny thereof obtained by selfing, to ensure that mutations are in homozygous form. These can be plants or seeds or plant parts of a cultivated breeding line, variety, inbred line or any plurality of cultivated plants or seeds. Alternatively these may be wild plants or wild relatives of *C. pepo.*

Likewise a 'mutant *Momordica charantia* population' or 'population of mutant *Momordica charantia* plants' refers to a plurality ofMomordica charantia seeds or plants or plant parts which have been treated with a conventional mutagenic agents, like chemicals or high energy radiation (e.g. x-rays, neutron radiation, gamma radiation or UV radiation) or progeny thereof obtained by selfing, to ensure that mutations are in homozygous form. These can be plants or seeds or plant parts of a cultivated breeding line, variety, inbred line or any plurality of cultivated plants or seeds. Alternatively these may be wild plants or wild relatives of *Momordica charantia.*

*Lagenaria siceraria* plants according to the invention, comprising reduced susceptibility to *P. cubensis*, can be produced by introducing one or more mutations into an allele of a LsAAP2A protein-encoding gene and/or into an allele of a LsAAP2B protein-encoding gene.

*C. pepo* plants according to the invention, comprising reduced susceptibility to *P. cubensis*, can be produced by introducing one or more mutations into an allele of a CpAAP2A protein-encoding gene and/or into an allele of a CpAAP2B protein-encoding gene.

*C. pepo* plants may herein be, for example, pumpkin plants.

*Momordica charantia* plants according to the invention, comprising reduced susceptibility to *P. cubensis*, can be produced by introducing one or more mutations into an allele of a McAAP protein-encoding gene.

A further embodiment of the present invention, therefore, concerns a method for production of a plant (selected from the species Lagenraria siceraria, *Cucurbita pepo* and *Momordica charantia*) comprising the steps of a) providing a population of mutant plants (e.g. a mutant Lagenraria siceraria population, or a mutant *Cucurbita pepo* population, or a mutantMomordica charantia population),
b) optionally selecting a plant which is less susceptible to *P. cubensis* than a non-mutated plant,
c) determining if a plant of the mutant population of a) or selected under b) has a mutation in an allele of a LsAAP2A protein-encoding gene and/or in an allele of a LsAAP2B protein-encoding gene in case the plant is of the species Lagenraria siceraria; (or in a CpAAP2A protein encoding gene and/or a CpAAP2B protein encoding gene in case the plant is of the species *C. pepo*; or in a McAAP protein encoding gene, in case the plant is of the species *Momordica charantia*), optionally
d) growing/cultivating the plants obtained under c).

In one aspect is a method for production of a plant (selected from the species Lagenraria siceraria, *Cucurbita pepo* and *Momordica charantia*) comprising the steps of a) introducing mutations in a population of plants (and optionally selfing the plants),
b) optionally selecting a plant which is less susceptible to *P. cubensis* than a non-mutated plant,
c) determining if the plant selected under b) has a mutation in an allele of a LsAAP2A protein-encoding gene and/or in an allele of a LsAAP2B protein-encoding gene in case the plant is of the species Lagenraria siceraria (or in a CpAAP2A protein encoding gene and/or a CpAAP2B protein encoding gene in case the plant is of the species *C. pepo*; or in a McAAP protein encoding gene in case the plant is of the species *Momordica charantia*) and selecting a plant comprising such a mutation, and optionally
d) growing/cultivating the plants obtained under c).

However, in one aspect the order of the steps can also be different, comprising:

a) providing a population of mutant plants (e.g. a mutant Lagenraria siceraria population, or a mutant *Cucurbita pepo* population, or a mutant *Momordica charantia* population),
b) determining if a plant of the mutant population of a) has a mutation in an allele of a ClAAP2A protein-encoding gene and/or in an allele of a LsAAP2A protein-encoding gene and/or in an allele of a LsAAP2B protein-encoding gene in case the plant is of the species Lagenraria siceraria (or in a CpAAP2A protein encoding gene and/or a CpAAP2B protein encoding gene in case the plant is of the species *C. pepo*; or in a McAAP protein encoding gene in case the plant is of the species *Momordica charantia*), and optionally
c) selfing the plant of b) or c) to generate a plant comprising the mutant allele in homozygous form, and optionally
d) determining if the plant of step c) or d) is less susceptible to *P. cubensis* than a non-mutated plant.

Or the steps may comprise:

a) introducing mutations in a population of plants (and optionally selfing the plants)
b) determining if a plant of a) has a mutation in an allele of a LsAAP2A protein-encoding gene and/or in an allele of a LsAAP2B protein-encoding gene in case the plant is of the species Lagenraria siceraria (or in a CpAAP2A protein encoding gene and/or a CpAAP2B protein encoding gene in case the plant is of the species *C. pepo*; or in a McAAP protein encoding gene in case the plant is of the species *Momordica charantia*) and optionally
c) selecting a plant comprising such a mutation, and optionally
d) selfing the plant of b) or c) to generate a plant comprising the mutant allele in homozygous form, and optionally
e) determining if the plant of step c) or d) is less susceptible to *P. cubensis* than the non-mutated plant.

A non-mutated plant may be e.g. a susceptible control plant, such as a plant comprising wild type, functional alleles in homozygous form, e.g. regarding *Lagenaria siceraria* a functional LsAAP2A and LsAAP2B allele, or regarding *C. pepo* a functional CpAAP2A and CpAAP2B in homozygous form, or regarding *Momordica charantia* a function McAAP allele in homozygous form.

Optionally, the above methods comprises selecting a plant comprising at least one copy of a mutant allele of a gene encoding a LsAAP2A or LsAAP2B protein (regarding *Lagenaria siceraria*), or at least one copy of a mutant allele of a gene encoding a CpAAP2A or CpAAP2B protein (regarding *Cucurbita pepo*), or at least a mutant allele of a gene encoding a McAAP protein (regarding *Momordica charantia*). The selected plants are also an embodiment.

Chemical substances, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide (NaN3) is described, for example, in Jauhar and Siddiq (1999, Indian Journal of Genetics, 59 (1), 23-28), in Rao (1977, Cytologica 42, 443-450), Gupta and Sharma (1990, Oryza 27, 217-219) and Satoh and Omura (1981, Japanese Journal of Breeding 31 (3), 316-326). The production of wheat mutants using NaN3 or maleic hydrazide is described in Arora et al. (1992, Annals of Biology 8 (1), 65-69). An overview of the production of wheat mutants using different types of energy-rich radiation and chemical substances is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutations in triticale. The use of MMS (methyl methane sulphonic acid) and gamma radiation for the production of millet mutants is described in Shashidhara et al. (1990, Journal of Maharashtra Agricultural Universities 15 (1), 20-23).

All these methods are basically suitable in the method for production of a plant according to the invention for producing mutant alleles in genes encoding a LsAAP2A or LsAAP2B protein (or CpAAP2A or CpAAP2B protein).

The plants generated and/or selected by these methods are also an embodiment of the invention. These plants can be used to make breeding lines and varieties comprising the mutant alleles.

Selecting plants having reduced susceptibility to *P. cubensis* can be done in a disease assay as e.g. described in the Examples. As the phenotype is at least seen in homozygous condition, selfing of the plant or the population of mutagenized plants is preferred before phenotyping. Mutations in the appropriate alleles, in particular in alleles of LsAAP2A protein-encoding gene or LsAAP2B protein encoding gene (or CpAAP2A protein encoding genes or CpAAP2B protein encoding genes, or a McAAP protein encoding gene), can be found with the help of methods known to the person skilled in the art. In particular, analyses based on hybridisations with probes (Southern Blot), amplification by means of polymerase chain reaction (PCR), sequencing of related genomic sequences and the search for individual nucleotide exchanges can be used for this purpose. Methods, which allow several plants to be investigated for mutations in certain genes in a short time, are particularly suitable. Such a method, so-called TILLING (Targeting Induced Local Lesions IN Genomes), has been described by McCallum et al. (2000, Plant Physiology 123, 439-442).

Other methods for identifying if a plant cell or plant comprises a mutant allele of a LsAAP2A or LsAAP2B protein-encoding gene (or CpAAP2A protein encoding genes or CpAAP2B protein encoding genes, or a McAAP protein encoding gene) comprise sequencing of the respective alleles and SNP marker analyses with methods common in the art and e.g. discussed in Thomson (2014, Plant Breeding and Biotechnology 2, 195-212). Also analysis of mRNA being expressed, and optionally quantified, can be used, e.g. to identify mutants having reduced or no gene expression.

These methods are basically suitable for identifying plant cells according to the invention and plants according to the invention having a mutant allele of a LsAAP2A or LsAAP2B protein-encoding gene or of a CpAAP2A protein encoding genes or CpAAP2B protein encoding genes, or a McAAP protein encoding gene.

In one aspect, a method for identifying a *Lagenaria siceraria* plant or plant part or cell comprising in its genome at least one copy of a mutant allele of LsAAP2A and/or LsAAP2B gene is provided, said method comprising determining whether the plant comprises in its genome at least one mutant lsaap2a allele and/or lsaap2b allele.

The *Lagenaria siceraria* plant or plant part may be a cultivated plant or a wild *Lagenaria siceraria* plant or wild relative of *Lagenaria siceraria*.

In another aspect, a method for identifying a *C. pepo* plant or plant part or cell comprising in its genome at least one copy of a mutant allele of CpAAP2A and/or CpAAP2B gene is provided, said method comprising determining whether the plant comprises in its genome at least one mutant cpaap2a allele and/or cpaap2b allele.

The *C. pepo* plant or plant part may be a cultivated plant or a wild *C. pepo* plant or wild relative of *C. pepo*.

In yet another aspect, a method for identifying a *Momordica charantia* plant or plant part or cell comprising in its genome at least one copy of a mutant allele of McAAP gene is provided, said method comprising determining whether the plant comprises in its genome at least one mutant mcaap allele.

The *Momordica charantia* plant or plant part may be a cultivated plant or a wild *Momordica charantia* plant or wild relative ofMomordica charantia.

This method may involve analysing (directly or indirectly) the gene expression of the lsaap2a allele and/or lsaap2b allele in case of *Lagenaria siceraria*; or of the cpaap2a allele and/or cpaap2b allele in case of *C. pepo*; or the mcaap allele in case of *Momordica charantia*, and/or the genomic nucleotide sequence of these alleles, or the mRNA nucleotide sequence of these alleles, or the protein sequence of the LsAAP2A or LsAAP2B protein (or of the CpAAP2A or CpAAP2B protein; or of the McAAP protein), or the protein amounts of the LsAAP2A or LsAAP2B protein (or of the CpAAP2A or CpAAP2B protein; or of the McAAP protein) of the plant or plant part or plant cell, to determine if the gene expression is knocked down or knocked out compared to the wild type plant or plant part or plant cell, or if the encoded protein comprises one or more amino acid insertions, deletions or replacements compared to the wild type LsAAP2A or LsAAP2B protein (or compared to the wild type CpAAP2A or CpAAP2B protein; or of the McAAP protein).

One method for analysing the presence of a mutant lsaap2a allele and/or lsaap2b allele (or of the cpaap2a allele and/or cpaap2b; or of the mcaap allele), is for example to assay the presence of a Single Nucleotide Polymorphism (SNP) between the genomic sequence of the mutant allele and the wild type allele, by, for example, designing primers for the SNP and genotyping plants or plant parts for the genotype of that particular SNP. For example a KASP assay can be used for detecting a SNP and thereby the mutant allele.

Likewise primers can be designed for allele specific DNA amplification, e.g. distinguishing a wild type allele from a mutant allele. Such PCR primers can be designed based on the differences between the wild type and the mutant allele. So if the mutant allele comprises a deletion of one or more nucleotides, e.g. in a coding sequence, the primers can be designed to differentiate between the presence of the mutant allele and the wild type allele. The skilled person can easily develop a molecular assay to detect a mutant allele. So one aspect of the invention comprises a method for determining whether a plant, plant part or plant cell comprises one or more copies of a mutant lsaap2a allele and/or lsaap2b allele (or of the cpaap2a allele and/or cpaap2b allele; or of the mcaap allele) by a method selected from analysing one or more nucleotides of the genomic lsaap2a allele and/or lsaap2b allele (or of the genomic cpaap2a allele and/or cpaap2b allele; or of the mcaap allele), analysing the mRNA (or cDNA) expressed by the lsaap2a allele and/or lsaap2b allele (or by the cpaap2a allele and/or cpaap2b allele; or by the mcaap allele) or analysing the LsAAP2A or LsAAP2B protein amount (or the CpAAP2A or CpAAP2B protein amount; or the McAAP protein amount) and/or amino acid sequence (using e.g, antibody based detection).

Thus, a method for determining whether a *Lagenaria siceraria* plant or plant part comprises at least one copy of a mutant allele of a gene named LsAAP2A is provided, said gene encodes a LsAAP2A protein of SEQ ID NO: 3 or a protein comprising at least 90%, 91%, 92%, 93%, 94% or 95% sequence identity to SEQ ID NO: 3, said method comprising analysing the LsAAP2A DNA, RNA or protein of the plant or plant part.

And a method for determining whether a *Lagenaria siceraria* plant or plant part comprises at least one copy of a mutant allele of a gene named LsAAP2B is provided, said gene encodes a LsAAP2B protein of SEQ ID NO: 6 or a protein comprising at least 90%, 91%, 92%, 93%, 94% or 95% sequence identity to SEQ ID NO: 6, said method comprising analysing the LsAAP2B DNA, RNA or protein of the plant or plant part.

Further, a method for determining whether a *Cucurbita pepo* plant or plant part comprises at least one copy of a mutant allele of a gene named CplAAP2A is provided, said gene encodes a CpAAP2A protein of SEQ ID NO: 14 or a protein comprising at least 90%, 91%, 92%, 93%, 94% or 95% sequence identity to SEQ ID NO: 14, said method comprising analysing the CpAAP2A DNA, RNA or protein of the plant or plant part.

And a method for determining whether a *Cucurbita pepo* plant or plant part comprises at least one copy of a mutant allele of a gene named CpAAP2B is provided, said gene encodes a CpAAP2B protein of SEQ ID NO: 15 or a protein comprising at least 90%, 91%, 92%, 93%, 94% or 95% sequence identity to SEQ ID NO: 15, said method comprising analysing the CpAAP2B DNA, RNA or protein of the plant or plant part.

In one aspect, especially in respect of the European Patent Convention, the watermelon plant according to the invention is "not obtained exclusively by an essentially biological process", or in one aspect the mutant lsaap2a and/or lsaap2b allele (or the mutant cpaap2a and/or cpaap2b allele; or the mutant mcaap allele) is not a natural mutant allele. If such a disclaimer is present in the claim of the European patent, it should be noted that using a watermelon plant comprising a mutant allele (e.g. a commercial variety of the applicant) to cross the mutant allele into a different background of watermelon will still be seen as falling under the claim, even though an exclusively essentially biological process (only crossing and selection) may have been used to transfer the allele into a different background.

Genetically Modified Plants

In another aspect also genetically modified (transgenic) Cucurbitaceae plants, plant parts and plant cells are provided, in which the endogenous gene expression of the AAP2A and/or AAP2B gene or McAAP gene is knocked down or knocked out. For example RNAi constructs can be made and the plant can be transformed with such construct to generate such plants using methods known in the art.

SEQUENCE DESCRIPTION

SEQ ID NO: 1 depicts a functional, wild type melon CmAAP2A protein.

SEQ ID NO: 2 depicts a functional, wild type watermelon ClAAP2A protein.

SEQ ID NO: 3 depicts a functional, wild type Bottle Gourd LsAAP2A protein.

SEQ ID NO: 4 depicts a functional, wild type melon CmAAP2B protein.

SEQ ID NO: 5 depicts a functional, wild type watermelon ClAAP2B protein.

SEQ ID NO: 6 depicts a functional, wild type Bottle gourd LsAAP2B protein.

SEQ ID NO: 7 depicts the CmAAP2A cDNA encoding the protein of SEQ ID NO: 1.

SEQ ID NO: 8 depicts the CmAAP2B cDNA encoding the protein of SEQ ID NO: 4.

SEQ ID NO: 9 depicts the ClAAP2A cDNA encoding the protein of SEQ ID NO: 2.

SEQ ID NO: 10 depicts the ClAAP2B cDNA encoding the protein of SEQ ID NO: 5.

SEQ ID NO: 11 depicts the LsAAP2A cDNA encoding the protein of SEQ ID NO: 3.

SEQ ID NO: 12 depicts the LsAAP2B cDNA encoding the protein of SEQ ID NO: 6.

SEQ ID NO: 13 depicts a functional, wild type bitter gourd McAAP protein.

SEQ ID NO: 14 depicts a functional, wild type *C. pepo* CpAAP2A protein.

SEQ ID NO: 15 depicts a functional, wild type *C. pepo* CpAAP2B protein.

SEQ ID NO: 16 depicts the McAAP cDNA encoding the protein of SEQ ID NO: 13.

SEQ ID NO: 17 depicts the CpAAP2A cDNA encoding the protein of SEQ ID NO: 14.

SEQ ID NO: 18 depicts the CpAAP2B cDNA encoding the protein of SEQ ID NO: 15.

SEQ ID NO: 19 depicts a functional, wild type *Cucumis sativus* CsAAP2A protein

EXAMPLES

The disease assay below is an assay for cucumber plants and the same assay can be used for melon plants.

The assay can also easily be adapted for other cucurbit species, such as watermelon or *C. pepo*, or methods known in the art can be used. Of course, a *P. cubensis* isolate which is pathogenic on the species to be tested needs to be used, and the appropriate susceptible control plants need to be included in addition to the plants to be tested for their susceptibility comprising one or more mutant AAP2A and/or AAP2B alleles (preferably in homozygous form). As leaf symptoms on different species vary, the inoculum concentration, the scoring date and the type of symptom and scale of scoring one or more disease symptoms may also be different. However, the skilled person is able to determine whether a plant line comprising a mutant allele according to the invention (preferably in homozygous form) shows significantly less disease symptoms (e.g. yellowing/chlorosis, or sporulation, or lesion area, or leaf area affected, etc.) compared to the susceptible control.

Example 1

*P. cubensis* Disease Assay 1.1 Plant material used:

Plant introduction line PI197088, highly resistant to downy mildew (DM) caused by *P. cubensis*, originating from Assam, India, 1951 and obtained from the United States National Plant Germplasm System (NPGS). Breeding line HS279 is a pickling type cucumber, susceptible to downy mildew, with good horticultural characteristics.

From a cross between these genotypes, F3BC3S3 populations were developed using HS279 as recurrent parent.

By repeated backcrossing using marker assisted selection (MAS) we obtained near isogenic lines (NILs), each having small PI 197088-derived introgressions on chromosome 4, in the susceptible background genotype. Instead of a single QTL (DM4.1) three individual loci could be distinguished within a 12 Mb interval, which were named DM4.1.1, DM4.1.2 and DM4.1.3. The individual effects of each of these three QTL on the disease phenotype is markedly different: the first QTL, DM4.1.1, decreased the amount of disease-induced necrosis, or "collapsing", although this effect was not possible to score in absence of the two other DM resistance QTLs. The second QTL, DM4.1.2, decreased the amount of sporulation of the pathogen. The third QTL, DM4.1.3, had a recessively inherited effect on pathogen-induced chlorosis (yellowing), as shown herein below. This effect was due to the presence of a mutant aap2a allele (of a endogenous gene referred to as CsAAP2A, i.e. Cucumber sativus AAP2A gene) in homozygous form, in which a transposable element was inserted in exon 4 of the gene. The transposable element (TE) insertion resulted in a knock-out of the CsAAP2A gene and the insertion of the TE led to truncation of the AAP protein after amino acid 160 (followed by 29 other amino acids). The last 306 amino acids of the wild type CsAAP2A protein of 466 amino acids were missing.

1.2 *Pseudoperonospora cubensis* inoculum maintenance and preparation:

An isolate of *P. cubensis* obtained from an infected cucumber field in Haelen, the Netherlands, was maintained on fully expanded cucumber leaves, healthy in appearance before inoculation. Detached leaves were kept in closed boxes containing water-soaked paper towels, and inoculated with a spore suspension developed as described below. Boxes containing inoculated cucumber leaves were kept in a climate chamber under 18° C. (day) and 15° C. (night), with a 16/8 h day/night cycle for ten days. Heavily infected detached leaves were preserved at −20° C. as inoculum source for <6 months. Spore suspensions were produced by washing spores from frozen infected leaves using tap water, and filtering through cheesecloth. The spore concentration was measured using a haemocytometer, and adjusted to $3*10^4$ spores/ml.

1.3 Plant inoculation and symptom assessment:

Six near isogenic lines (NILs) comprising only the QTL DM4.1.3 in homozygous form (10 plants per line) and the recurrent parent HS279 (53 plants), were grown in climate chambers with temperatures of 22° C. (day) and 17° C. (night), with a 16/8 h day/night cycle, and a relative humidity of 80%.

Cucumber plants for *P. cubensis* disease tests were grown in plastic tents, which were closed the day before inoculation to ensure a high relative humidity. When plants were 2.5 weeks old, both sides of cucumber leaves (1" true leaf) were sprayed with spore suspension prepared as described above. After inoculation, plants were left in darkness at 18/15° C. (day/night) for 24 hours in closed plastic tents. At seven days post inoculation (dpi), yellowing (chlorosis), of the inoculated leaves were assessed by eye on a 1-9 scale, 9 being fully green and 1 being fully yellow. (Optionally at 12 dpi sporulation can be assessed, e.g. on a scale of 1 to 9, 9 being fully resistant (no sporulation) and 1 being fully susceptible (high sporulation)).

1.4 Results:

Each plant was scored for yellowing (chlorosis) and the number of plants with a score were counted as shown in the table below:

| Plant line | No of plants with score 3 | No of plants with score 4 | No of plants with score 5 | No of plants with score 6 | No of plants with score 7 | No of plants with score 8 | No of plants with score 9 | Average score of the line |
|---|---|---|---|---|---|---|---|---|
| NIL-A | | | 5 | 5 | | | | 5.5 |
| NIL-B | | | | 2 | 8 | | | 6.8 |
| NIL-C | | | | 5 | 5 | | | 6.5 |
| NIL-D | | | | 10 | | | | 6.0 |
| NIL-E | | | 2 | 8 | | | | 5.8 |
| NIL-F | | | 2 | 8 | | | | 5.8 |
| HS279 | 2 | 48 | 3 | | | | | 4.0 |

The NIL comprising QTL 4.1.3 in homozygous form (i.e. comprising a mutant csaap2a allele in homozygous form)

therefore showed less yellowing at 7 days after inoculation than the susceptible recurrent parent HS279.

Example 2

Identification of a cmaap2a mutant allele

More than 130 genomes of different melon accessions were screened for their CmAAP2A sequences. One *C. melo* var *momordica* accession was found comprising a STOP codon mutation in the codon tgg, coding for tryptophan (W) of amino acid 372 of SEQ ID NO: 1. Thus the codon tgg (W) was mutated to tga (STOP).

Initial disease testing using the assay of Example 1 resulted in the wild *C. melo* var *momordica* accession having a yellowing score of 8 or 9 at 6 dpi and at 8 dpi, while the azygous plants lacking the mutation had a yellowing score of 7. The scale for yellowing is given in Example 1, 9 being fully green and 1 being fully yellow.

The mutant cmaap2a allele will be introgressed into susceptible cultivated melon breeding lines in homozygous form in order to assess the effect on susceptibility to *P. cubensis* using e.g. the above disease assay to assess yellowing compared to the susceptible control (e.g. the recurrent parent, comprising the wild type CmAAP2A and CmAAP2B alleles).

Initial results of a field trial including a line comprising the introgression indicate that the line is indeed less susceptible to *P. cubensis* than the susceptible control.

Example 3

Generation of a *Cucumis sativus* CsAAP2A TILLING Mutant

As shown in FIG. 4, the cucumber and melon AAP2A proteins have a very high sequence identity. The Cucurbitaceae AAP2A and AAP2B genes cluster together in the same phylogenetic clade and their function is therefore deemed to be conserved. Phylogenetic clusters are shown in Chapter 5, FIG. 5 of the PhD thesis of Jeroen Berg. The *Cucumis melo, Cucumis sativus, Citrullus lanata* and *Cucurbita pepo* AAP2A and AAP2B genes for example cluster all together in the same subclade of clade 3, subclade 3A.

A mutant TILLING population of cucumber was screened for mutations in CsAAP2A and CsAAP2B alleles. Cucumber plants comprising the f 11 wing mutations were found as shown in the table below.

| Gene | Mutation | Amino Acid substitution | Sown | Phenotype |
|---|---|---|---|---|
| CsAAP2A | G/A | W25Stop | Yes | Reduces yellowing and sporulation |

A. *P. cubensis* disease assay was carried out for mutant line comprising a mutant csaap2a allele comprising the W25Stop mutation using the disease assay described in Example 1. The phenotyping was done at 7 days following inoculation for both yellowing and for sporulation. The same scales were used. The number of plants with each score were recorded. As shown in the table below, the plant comprising the csaap2a W25STOP mutant allele in homozygous form has significantly less yellowing and less sporulation than the wild type, confirming that csaap2a mutants confer a reduction in susceptibility to *P. cubensis*.

| | Yellowing | | | Sporulation | | | | | |
|---|---|---|---|---|---|---|---|---|---|
| score | Score 6 | Score 7 | Average score yellowing | Score 2 | Score 3 | Score 4 | Score 5 | Score 8 | Average score sporulation |
| Azygous/ WT | 12 | | 6.0 | 2 | 7 | 2 | 1 | | 3.2 |
| Heterozygous for W25Stop | 14 | | 6.0 | | 14 | | | | 3.0 |
| Homozygous for W25Stop | 1 | 23 | 7.0 | 2 | 10 | 10 | | 2 | 4.1 |
| Parent line- WT | 4 | | 6.0 | | 4 | | | | 3.0 |

As in cucumber two mutants in AAP2A (the TE, Transposable Element, insertion in CsAAP2A and the above W25STOP mutant) result in reduced susceptibility to *P. cubensis*, and given the high conservation of the AAP2A gene in species of Cucurbitaceae, any reduced function or loss of function of AAP2A is likely to result in reduced susceptibility to *P. cubensis* in melon and other species of Cucurbitaceae. In melon the same mutant, i.e. CmAAP2A of SEQ ID NO: 1 comprising a W25STOP mutation is therefore expected to result in reduced susceptibility to *P. cubensis* when the mutant allele is in homozygous form in the plant.

In melon also another mutant has been identified in a line comprising reduced susceptibility to *P. cubensis*. In this line a A132P substitution was found in the CmAAP2A protein of SEQ ID NO: 1. The mutation is at the second nucleotide of exon 4 and is thought to result in aberrant splicing, likely leading to a loss-of-function of the encoded CmAAP2A protein.

The invention claimed is:

1. A cultivated plant or plant part of the species *Cucumis melo* comprising at least one copy of a mutant allele of a gene named CmAAP2A, said gene encodes the CmAAP2A protein of SEQ ID NO: 1 or a protein comprising at least 95% sequence identity to SEQ ID NO: 1, wherein said mutant allele results in no expression of the CmAAP2A gene, or wherein the mutant allele encodes a mutant CmAAP2A protein having a loss-of-function compared to the wild type CmAAP2A protein and wherein said mutant protein comprises a mutation in the conserved Amino Acid Transporter Domain at amino acids 20 to 453 of SEQ ID NO: 1 or in an Amino Acid Transporter Domain comprising at least 95% sequence identity to amino acids 20 to 453 of SEQ ID NO: 1, wherein said mutant allele is introgressed from a wild melon or wild relative of melon into the cultivated melon, or wherein said mutant allele is induced by chemical mutagenesis, radiation mutagenesis, tissue culture or targeted genome editing techniques.

2. The plant or plant part according to claim 1, wherein said mutant allele confers reduced susceptibility to the oomycete *Pseudoperonopora cubensis* when the mutant allele is in homozygous form compared to a plant or plant part homozygous for the wild type allele of the CmAAP2A gene.

3. The plant or plant part according, wherein said mutant protein is truncated in the Amino Acid Transporter Domain.

4. The plant or plant part according to claim 1, wherein said mutant protein has a mutation in the codon for amino acid 25, which encodes Tryptophan (W), is replaced by a Stop codon or the codon for amino acid 132, which encodes Adenine (A), is replaced by a Proline (P) or the codon for amino acid 372, which encodes Tryptophan (W), is replaced with a stop codon.

5. The plant or plant part according to claim 1, wherein said plant or plant part is homozygous for the mutant allele.

6. The plant or plant part according claim 1, wherein said plant or plant part further comprises at least one copy of a mutant allele of a gene named CmAAP2B, said gene encodes a CmAAP2B protein of SEQ ID NO: 4 or a protein comprising at least 95% sequence identity to SEQ ID NO: 4.

7. A seed from which a plant or plant part according to claim 1 can be grown.

8. A fruit produced by the plant or plant part according to claim 1, wherein the fruit comprises the mutant allele in homozygous form.

9. The plant or plant part according to claim 1, wherein the plant part is a cell, a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther.

10. A vegetatively propagated plant propagated from the plant or plant part according to claim 9.

11. A method of melon fruit production, said method comprising growing the plant or plant part according to claim 1 comprising the mutant CmAAP2A allele in homozygous form, said method optionally comprising a reduced treatment with fungicides compared to a susceptible control plant, and harvesting the fruits produced by said plants.

12. A method for generating a melon plant comprising a mutant allele of a gene named CmAAP2A, said gene encodes a CmAAP2A protein of SEQ ID NO: 1 or a protein comprising at least 95% sequence identity to SEQ ID NO: 1, said method comprising:

a) providing a population of mutant melon plants, b) determining if a plant of the mutant population of step a) has a mutation in an allele of a CmAAP2A protein-encoding gene, c) selecting a plant comprising a mutation in an allele of a CmAAP2A protein-encoding gene, d) selfing the plant selected in step c) to generate a plant comprising the mutant allele in homozygous form, and optionally e) determining if the plant of step c) or d) is less susceptible to *P. cubensis* than a non-mutated plant.

13. A method for determining whether a melon plant or plant part of the species *Cucumis melo* comprises at least one copy of a mutant allele of a gene named CmAAP2A, said gene encodes a CmAAP2A protein of SEQ ID NO: 1 or a protein comprising at least 95% sequence identity to SEQ ID NO: 1 and wherein the expression of said mutant allele is knocked out or wherein said mutant allele encodes a mutant protein comprising a mutation in the conserved Amino Acid Transporter Domain at amino acid 20 to 453 of SEQ ID NO: 1, or in an Amino Acid Transporter Domain comprising at least 95° % sequence identity to amino acids 20 to 453 of SEQ ID NO: 1, said method comprising providing a melon plant or plant part of the species *Cucumis melo* comprising said at least one copy of a mutant allele of a gene named CmAAP2A generated by chemical mutagenesis or radiation mutagenesis; analyzing the CmAAP2A DNA, RNA or protein of the plant or plant part, to determine if the CmAAP2A gene expression is knocked out as compared to the wild type plant or plant part, or to determine if the CmAAP2A gene encodes a mutant protein comprising a mutation in the conserved Amino Acid Transporter Domain at amino acids 20 to 450 of SEQ ID NO: 1, or in the Amino Acid Transporter Domain comprising at least 95% sequence identity to amino acids 20 to 453 of SEQ ID NO: 1.

14. The method according to claim 12, wherein the population of mutant plants is generated by chemical mutagenesis, radiation mutagenesis, tissue culture or or progeny thereof obtained by selfing, to ensure that mutations are in homozygous form.

15. The plant or plant part according to claim 1, wherein said mutant allele is an allele generated by a targeted genome editing technique.

16. The plant or plant part according to claim 1, wherein the mutant allele encodes the CmAAP2A protein of SEQ ID NO: 1 comprising a W25STOP mutation.

17. The method according to claim 12, wherein the mutant allele is a mutant allele generated by a targeted genome editing technique.

18. A method for transferring a mutant cmaap2a allele from a wild melon plant into a cultivated melon plant, said method comprising a) introgressing a mutant allele of a gene named CmAAP2A, said gene encodes a CmAAP2A protein of SEQ ID NO: 1 or a protein comprising at least 95% sequence identity to SEQ ID NO: 1, from a wild melon plant into cultivated melon, and b) determining the effect of the mutant allele on the susceptibility to *Pseudoperonospora cubensis* in a cultivated melon plant of step a) which comprises the mutant allele in homozygous form.

19. The method according to claim 18, wherein the cultivated melon plant is susceptible to *P. cubensis*.

20. The plant or plant part according to claim 1, wherein said plant or plant part is homozygous for the mutant allele and further comprises at least one copy of a mutant allele of a gene named CmAAP2B, said gene encodes a CmAAP2B protein of SEQ ID NO: 4 or a protein comprising at least 95% sequence identity to SEQ ID NO: 4.

21. A seed from which the plant or plant part according to claim 20 can be grown.

* * * * *

SEQUENCE LISTING

<160> NUMBER OF SEQ ID NOS: 19

<210> SEQ ID NO 1
<211> LENGTH: 466
<212> TYPE: PRT
<213> ORGANISM: artificial
<220> FEATURE:
<223> OTHER INFORMATION: Melon AAP2A protein
<220> FEATURE:
<221> NAME/KEY: Exon1 encoded
<222> LOCATION: (1)..(21)
<220> FEATURE:
<221> NAME/KEY: AA_trans
<222> LOCATION: (20)..(453)
<220> FEATURE:
<221> NAME/KEY: Exon2 encoded
<222> LOCATION: (22)..(99)
<220> FEATURE:
<221> NAME/KEY: Exon3 encoded
<222> LOCATION: (100)..(131)
<220> FEATURE:
<221> NAME/KEY: Exon4  encoded
<222> LOCATION: (132)..(201)
<220> FEATURE:
<221> NAME/KEY: Exon5 encoded
<222> LOCATION: (202)..(248)
<220> FEATURE:
<221> NAME/KEY: Exon6 encoded
<222> LOCATION: (249)..(466)

<400> SEQUENCE: 1

```
Met Ala Val Leu Pro Val Asn Asp Ser Ala Ser Leu Asp Asp Asp Gly
1               5                   10                  15

His Pro Lys Arg Thr Gly Thr Phe Trp Thr Ala Ser Ala His Ile Ile
            20                  25                  30

Thr Thr Val Ile Gly Ser Gly Val Leu Ser Leu Ala Trp Ala Ile Ala
        35                  40                  45

Gln Leu Gly Trp Ile Val Gly Pro Ser Val Met Leu Leu Phe Ala Phe
    50                  55                  60

Ile Gly Tyr Tyr Thr Ser Cys Leu Leu Ala Asp Cys Tyr Arg Ser Gly
65                  70                  75                  80

Asp Pro Leu Asn Gly Lys Arg Asn His Thr Tyr Met His Ala Val Arg
                85                  90                  95

Ser Leu Leu Gly Glu Ala His Met Val Ala Cys Gly Val Met Gln Asn
            100                 105                 110

Ile Asn Leu Ile Gly Ile Thr Ile Gly Tyr Thr Ile Ala Ser Ser Ile
        115                 120                 125

Ser Met Met Ala Ile Lys Arg Ser Asn Cys Phe His Ser Ser Gly Gly
    130                 135                 140

Lys Asn Pro Cys His Ile Ser Ser Asn Pro Phe Met Val Ser Phe Gly
145                 150                 155                 160

Val Leu Glu Ile Ile Leu Ser Gln Ile Pro Asn Phe Asp Gln Ile Trp
                165                 170                 175

Trp Leu Ser Thr Leu Ala Ala Ile Met Ser Phe Thr Tyr Ser Phe Ile
            180                 185                 190

Gly Leu Ser Leu Gly Ile Ala Lys Val Ala Glu Ser Gly Arg Phe Lys
        195                 200                 205

Gly Thr Ile Ser Gly Val Ser Val Gly Thr Ile Ser Lys Thr Glu Lys
    210                 215                 220

Lys Leu Arg Ser Phe Gln Ala Leu Gly Asp Ile Ala Phe Ala Tyr Ser
225                 230                 235                 240

Phe Ala Ile Val Leu Ile Glu Ile Gln Asp Thr Ile Lys Cys Pro Pro
```

```
                245                 250                 255

Ser Glu Ala Lys Thr Met Lys Lys Ala Thr Thr Phe Ser Ile Ile Leu
            260                 265                 270

Thr Thr Leu Phe Tyr Leu Leu Cys Gly Cys Met Gly Tyr Ala Ala Phe
        275                 280                 285

Gly Asn Asn Ala Pro Gly Asn Leu Leu Thr Gly Phe Gly Phe Tyr Asn
    290                 295                 300

Pro Phe Trp Leu Ile Asp Ile Ala Asn Val Ala Ile Val Val His Leu
305                 310                 315                 320

Val Gly Ala Tyr Gln Val Leu Ser Gln Pro Ile Phe Ala Phe Val Glu
                325                 330                 335

Lys Lys Ala Ala Gln Ala Trp Pro Asp Ser Pro Phe Ile Asn Lys Asp
            340                 345                 350

Tyr Lys Leu Ser Ile Ser Ser Ser Arg Leu Tyr Asn Ile Asn Leu Phe
        355                 360                 365

Arg Leu Phe Trp Arg Thr Leu Phe Val Cys Phe Thr Thr Thr Ile Ala
    370                 375                 380

Met Leu Ile Pro Phe Phe Asn Asp Ile Val Gly Ile Ile Gly Ala Leu
385                 390                 395                 400

Gln Phe Trp Pro Leu Thr Val Tyr Phe Pro Ile Gln Met Tyr Ile Val
                405                 410                 415

Gln Lys Lys Ile Pro Gln Trp Ser Val Lys Trp Ile Cys Val Gln Thr
            420                 425                 430

Met Ser Val Gly Cys Leu Leu Val Ser Leu Ala Ala Ala Val Gly Ser
        435                 440                 445

Ile Ser Gly Val Met Leu Asp Leu Lys Val Tyr Lys Pro Phe Lys Thr
    450                 455                 460

Met Tyr
465


<210> SEQ ID NO 2
<211> LENGTH: 466
<212> TYPE: PRT
<213> ORGANISM: artificial
<220> FEATURE:
<223> OTHER INFORMATION: Watermelon AAP2A protein
<220> FEATURE:
<221> NAME/KEY: Exon1 encoded
<222> LOCATION: (1)..(21)
<220> FEATURE:
<221> NAME/KEY: Aa_trans
<222> LOCATION: (20)..(453)
<220> FEATURE:
<221> NAME/KEY: Exon2 encoded
<222> LOCATION: (22)..(99)
<220> FEATURE:
<221> NAME/KEY: Exon3 encoded
<222> LOCATION: (100)..(131)
<220> FEATURE:
<221> NAME/KEY: Exon4 encoded
<222> LOCATION: (132)..(201)
<220> FEATURE:
<221> NAME/KEY: Exon5 encoded
<222> LOCATION: (202)..(248)
<220> FEATURE:
<221> NAME/KEY: Exon6 encoded
<222> LOCATION: (249)..(466)

<400> SEQUENCE: 2

Met Ala Val Leu Pro Phe Ser Asp Ser Ala Ile Phe Asp Asp Asp Gly
1               5                   10                  15

Arg Pro Lys Arg Thr Gly Thr Phe Trp Thr Ala Ser Ala His Ile Ile
```

-continued

```
            20                  25                  30

Thr Thr Val Ile Gly Ser Gly Val Leu Ser Leu Ala Trp Ala Ile Ala
        35                  40                  45

Gln Leu Gly Trp Ile Ala Gly Pro Ser Val Met Leu Leu Phe Ala Phe
    50                  55                  60

Ile Gly Tyr Tyr Thr Ser Cys Leu Leu Ala Asp Cys Tyr Arg Ser Gly
65                  70                  75                  80

Asp Pro Val Asn Gly Lys Arg Asn His Thr Tyr Met His Ala Val Arg
                85                  90                  95

Ser Leu Leu Gly Glu Ala His Met Val Ala Cys Gly Val Met Gln Tyr
            100                 105                 110

Ile Asn Leu Ile Gly Ile Thr Ile Gly Tyr Thr Ile Ala Ser Ser Ile
        115                 120                 125

Ser Met Met Ala Ile Lys Arg Ser Asn Cys Phe His Ser Ser Gly Gly
    130                 135                 140

Lys Asn Pro Cys His Ile Ser Ser Asn Pro Phe Met Leu Cys Phe Gly
145                 150                 155                 160

Ile Val Glu Ile Ile Leu Ser Gln Ile Pro Asn Phe Asp Gln Ile Trp
                165                 170                 175

Trp Leu Ser Thr Val Ala Ala Ile Met Ser Phe Thr Tyr Ser Thr Ile
            180                 185                 190

Gly Leu Ser Leu Gly Ile Ala Lys Val Ala Glu Ser Gly Ser Phe Lys
        195                 200                 205

Gly Thr Leu Ser Gly Val Ser Val Gly Ser Ile Thr Arg Thr Glu Lys
    210                 215                 220

Lys Trp Arg Ser Phe Gln Ala Leu Gly Asp Ile Ala Phe Ala Tyr Ser
225                 230                 235                 240

Phe Ala Ile Val Leu Ile Glu Ile Gln Asp Thr Ile Arg Cys Pro Pro
                245                 250                 255

Ser Glu Ala Lys Thr Met Lys Lys Ala Thr Gly Phe Ser Ile Ile Leu
            260                 265                 270

Thr Thr Leu Phe Tyr Leu Leu Cys Gly Cys Met Gly Tyr Ala Ala Phe
        275                 280                 285

Gly Asn Asn Ala Pro Gly Asn Leu Leu Thr Gly Phe Gly Phe Tyr Asn
    290                 295                 300

Pro Phe Trp Leu Leu Asp Ile Ala Asn Val Ala Ile Val Val His Leu
305                 310                 315                 320

Val Gly Ala Tyr Gln Val Leu Ser Gln Pro Val Phe Ala Phe Val Glu
                325                 330                 335

Lys Lys Ala Ala Leu Ala Trp Pro Asp Ser Pro Phe Ile Thr Lys Asp
            340                 345                 350

Tyr Lys Leu Ser Ile Ser Ser Ser Arg Ser Tyr Asn Ile Asn Leu Phe
        355                 360                 365

Arg Leu Val Trp Arg Ser Leu Phe Val Cys Phe Thr Thr Ile Ile Ala
    370                 375                 380

Met Leu Ile Pro Phe Phe Asn Asp Ile Val Gly Ile Ile Gly Ala Leu
385                 390                 395                 400

Gln Phe Trp Pro Leu Thr Val Tyr Phe Pro Val Gln Met Tyr Met Val
                405                 410                 415

Gln Lys Lys Val Pro Lys Trp Ser Val Lys Trp Ile Tyr Val Gln Thr
            420                 425                 430

Ile Ser Met Gly Cys Leu Leu Val Ser Leu Ala Ala Ala Val Gly Ser
        435                 440                 445
```

```
Ile Asn Gly Val Met Leu Asp Leu Lys Val Tyr Lys Pro Phe Lys Thr
    450                 455                 460

Met Tyr
465


<210> SEQ ID NO 3
<211> LENGTH: 466
<212> TYPE: PRT
<213> ORGANISM: artificial
<220> FEATURE:
<223> OTHER INFORMATION: Bottle Gourd AAP2A protein
<220> FEATURE:
<221> NAME/KEY: Aa_trans
<222> LOCATION: (20)..(453)

<400> SEQUENCE: 3

Met Ala Val Leu Pro Ile Asn Asp Ser Ala Ser Phe Asp Asp Asp Gly
1               5                   10                  15

Arg Pro Lys Arg Thr Gly Thr Phe Trp Thr Ala Ser Ala His Ile Ile
            20                  25                  30

Thr Thr Val Ile Gly Ser Gly Val Leu Ser Leu Ala Trp Ala Ile Ala
        35                  40                  45

Gln Leu Gly Trp Ile Ala Gly Pro Ser Val Met Leu Leu Phe Ala Phe
    50                  55                  60

Ile Gly Tyr Tyr Thr Ser Cys Phe Leu Ala Asp Cys Tyr Arg Ser Gly
65                  70                  75                  80

Asp Pro Val Asn Gly Lys Arg Asn His Thr Tyr Met His Ala Val Arg
                85                  90                  95

Ser Leu Leu Gly Glu Ala His Met Val Ala Cys Gly Val Met Gln Asn
            100                 105                 110

Ile Asn Leu Ile Gly Ile Thr Ile Gly Tyr Thr Ile Ala Ser Ser Ile
        115                 120                 125

Ser Met Met Ala Ile Lys Arg Ser Asn Cys Phe His Arg Ser Gly Gly
    130                 135                 140

Lys Asn Pro Cys His Ile Ser Ser Asn Pro Phe Met Leu Ser Phe Gly
145                 150                 155                 160

Ile Val Glu Ile Ile Leu Ser Gln Ile Pro Asn Phe Asp Gln Ile Trp
                165                 170                 175

Trp Leu Ser Ile Val Ala Ala Ile Met Ser Phe Thr Tyr Ser Thr Ile
            180                 185                 190

Gly Leu Ser Leu Gly Ile Ala Lys Val Ala Glu Ser Gly Ser Val Lys
        195                 200                 205

Gly Thr Leu Ser Gly Ile Ser Val Gly Ser Ile Thr Pro Thr Glu Lys
    210                 215                 220

Lys Trp Arg Ser Phe Gln Ala Leu Gly Asp Ile Ala Phe Ala Tyr Ser
225                 230                 235                 240

Phe Ala Ile Val Leu Ile Glu Ile Gln Asp Thr Ile Arg Cys Pro Pro
                245                 250                 255

Ser Glu Ala Lys Thr Met Lys Lys Ala Thr Gly Phe Ser Ile Ile Leu
            260                 265                 270

Thr Thr Leu Phe Tyr Leu Leu Cys Gly Cys Thr Gly Tyr Ala Ala Phe
        275                 280                 285

Gly Asn Asn Ala Pro Gly Asn Leu Leu Thr Gly Phe Gly Phe Tyr Asn
    290                 295                 300

Pro Phe Trp Leu Leu Asp Ile Ala Asn Val Ala Ile Val Phe His Leu
305                 310                 315                 320
```

Val Gly Ala Tyr Gln Val Leu Ser Gln Pro Val Phe Ala Phe Val Glu
325 330 335

Lys Lys Ala Ala Gln Ala Trp Pro Asp Ser Ala Phe Ile Thr Lys Asp
340 345 350

Tyr Lys Leu Ser Leu Ser Ser Ser Arg Ser Tyr Asn Ile Asn Leu Phe
355 360 365

Arg Leu Ile Trp Arg Ser Leu Phe Val Cys Phe Thr Thr Ile Val Ala
370 375 380

Met Leu Ile Pro Phe Phe Asn Asp Ile Val Gly Ile Ile Gly Ala Leu
385 390 395 400

Gln Phe Trp Pro Leu Thr Val Tyr Phe Pro Val Gln Met Tyr Ile Val
405 410 415

Gln Lys Lys Ile Pro Lys Trp Ser Val Lys Trp Ile Tyr Val Gln Ile
420 425 430

Met Ser Met Gly Cys Leu Leu Val Ser Leu Ala Ala Ala Val Gly Ser
435 440 445

Ile Asn Gly Val Met Leu Asp Leu Lys Val Tyr Lys Pro Phe Lys Thr
450 455 460

Met Tyr
465

<210> SEQ ID NO 4
<211> LENGTH: 466
<212> TYPE: PRT
<213> ORGANISM: artificial
<220> FEATURE:
<223> OTHER INFORMATION: Melon AAP2B protein
<220> FEATURE:
<221> NAME/KEY: Aa_trans
<222> LOCATION: (20)..(453)

<400> SEQUENCE: 4

Met Ala Val Leu Pro Val Asn Asp Ser Ala Ser Phe Asp Asp Asp Gly
1 5 10 15

Arg Pro Lys Arg Thr Gly Thr Phe Trp Thr Ala Ser Ala His Ile Ile
20 25 30

Thr Ala Val Ile Gly Ser Gly Val Leu Ser Leu Ala Trp Ala Ile Ala
35 40 45

Gln Leu Gly Trp Ile Ala Gly Pro Ser Val Met Leu Leu Phe Ser Phe
50 55 60

Ile Gly Tyr Tyr Thr Ser Cys Leu Leu Ala Asp Cys Tyr Arg Ser Gly
65 70 75 80

Asp Pro Val Ser Gly Lys Arg Asn Pro Thr Tyr Met His Ala Val Arg
85 90 95

Ser Leu Leu Gly Glu Thr His Met Val Ala Cys Gly Ile Met Gln Tyr
100 105 110

Ile Asn Leu Ile Gly Ile Thr Ile Gly Tyr Thr Ile Ala Ser Ser Ile
115 120 125

Ser Met Met Ala Ile Lys Arg Ser Asn Cys Phe His Ser Ser Gly Gly
130 135 140

Lys Asn Pro Cys His Ile Ser Ser Asn Pro Phe Met Leu Ser Phe Gly
145 150 155 160

Ile Val Glu Ile Ile Leu Ser Gln Ile Pro Asn Phe Asp Gln Ile Trp
165 170 175

Trp Leu Ser Ile Val Ala Ala Ile Met Ser Phe Thr Tyr Ser Ser Ile
180 185 190

Gly Leu Thr Leu Gly Ile Ala Lys Val Ala Glu Ser Gly Val Phe Lys
195 200 205

Gly Thr Leu Ser Gly Ile Thr Val Gly Thr Val Thr Gln Ser Glu Lys
210 215 220

Ile Trp Arg Ser Phe Gln Ala Leu Gly Asp Ile Ala Phe Ala Tyr Ser
225 230 235 240

Phe Ala Ile Val Leu Ile Glu Val Gln Asp Thr Ile Arg Cys Pro Pro
245 250 255

Ser Glu Ala Lys Thr Met Lys Lys Ala Ala Gly Phe Ser Ile Thr Leu
260 265 270

Thr Thr Ile Phe Tyr Ile Leu Cys Gly Cys Met Gly Tyr Ala Ala Phe
275 280 285

Gly Asn Thr Ala Pro Gly Asn Leu Leu Thr Gly Phe Gly Phe Tyr Asn
290 295 300

Pro Phe Trp Leu Leu Asp Ile Ala Asn Val Ser Ile Val Val His Leu
305 310 315 320

Val Gly Ala Tyr Gln Val Phe Ser Gln Pro Val Tyr Ala Phe Val Glu
325 330 335

Lys Lys Val Val Gln Thr Trp Pro Asp Thr Pro Phe Phe Thr Lys Glu
340 345 350

Tyr Lys Leu Ser Leu Phe Ser Ser Arg Phe Tyr Asn Ile Asn Leu Phe
355 360 365

Arg Leu Val Trp Arg Thr Leu Phe Val Cys Phe Thr Thr Ile Val Ala
370 375 380

Met Leu Leu Pro Phe Phe Asn Asp Ile Val Gly Ile Ile Gly Ala Leu
385 390 395 400

Gln Phe Trp Pro Met Thr Val Tyr Phe Pro Val Gln Met Tyr Val Val
405 410 415

Gln Lys Lys Val Pro Lys Trp Ser Val Lys Trp Ile Cys Val Gln Thr
420 425 430

Met Ser Met Gly Cys Leu Leu Ile Ser Leu Ala Ala Ala Val Gly Ser
435 440 445

Ile Ser Gly Val Met Leu Asp Leu Lys Val Tyr Lys Pro Phe Lys Thr
450 455 460

Met Tyr
465

<210> SEQ ID NO 5
<211> LENGTH: 466
<212> TYPE: PRT
<213> ORGANISM: artificial
<220> FEATURE:
<223> OTHER INFORMATION: Watermelon AAP2B protein
<220> FEATURE:
<221> NAME/KEY: Aa_trans
<222> LOCATION: (20)..(453)

<400> SEQUENCE: 5

Met Ala Val Leu Pro Ile Asn Asp Ser Ala Ser Phe Asp Asp Asp Gly
1 5 10 15

Arg Pro Lys Arg Thr Gly Thr Phe Trp Thr Ala Ser Ala His Ile Ile
20 25 30

Thr Ala Val Ile Gly Ser Gly Val Leu Ser Leu Ala Trp Ala Ile Ala
35 40 45

Gln Leu Gly Trp Ile Ala Gly Pro Phe Val Met Leu Leu Phe Ala Phe
50 55 60

```
Ile Gly Tyr Tyr Thr Ser Cys Leu Leu Ala Asp Cys Tyr Arg Ser Gly
65                  70                  75                  80

Asp Pro Val Asn Gly Lys Arg Asn His Thr Tyr Met His Ala Val Arg
                85                  90                  95

Ser Leu Leu Gly Glu Ala His Met Val Ala Cys Gly Val Met Gln Tyr
            100                 105                 110

Ile Asn Leu Ile Gly Ile Thr Ile Gly Tyr Thr Ile Ala Ser Ser Ile
        115                 120                 125

Ser Met Met Ala Ile Lys Arg Ser Asn Cys Phe His Ser Ser Gly Gly
    130                 135                 140

Lys Asn Pro Cys His Ile Ser Ser Asn Pro Phe Met Leu Cys Phe Gly
145                 150                 155                 160

Ile Val Glu Ile Ile Leu Ser Gln Ile Pro Asn Phe Asp Gln Ile Trp
                165                 170                 175

Trp Leu Ser Thr Val Ala Ala Ile Met Ser Phe Thr Tyr Ser Thr Ile
            180                 185                 190

Gly Leu Ser Leu Gly Ile Ala Lys Val Ala Glu Ser Gly Ser Phe Lys
        195                 200                 205

Gly Thr Leu Ser Val Ile Ser Val Gly Thr Ile Thr Gln Thr Glu Lys
    210                 215                 220

Ile Trp Arg Ser Phe Gln Ala Leu Gly Asp Ile Ala Phe Ala Tyr Ser
225                 230                 235                 240

Phe Ala Ile Val Leu Ile Glu Val Gln Asp Thr Ile Thr Cys Pro Pro
                245                 250                 255

Ser Glu Ala Lys Thr Met Lys Lys Ala Thr Gly Phe Ser Ile Ala Leu
            260                 265                 270

Thr Thr Val Phe Tyr Leu Leu Cys Gly Ser Met Gly Tyr Ala Ala Phe
        275                 280                 285

Gly Asn Thr Ala Pro Gly Asn Leu Leu Thr Gly Phe Gly Phe Tyr Asn
    290                 295                 300

Pro Phe Trp Leu Leu Asp Ile Ala Asn Ile Ala Ile Val Ile His Leu
305                 310                 315                 320

Val Gly Ala Tyr Gln Val Phe Ser Gln Pro Val Phe Ala Phe Val Glu
                325                 330                 335

Lys Lys Ala Thr Gln Ala Trp Pro Asp Ser Ala Val Ile Thr Lys Asp
            340                 345                 350

His Lys Leu Ser Leu Phe Ser Ser His Ser Tyr Asn Ile Asn Leu Phe
        355                 360                 365

Arg Leu Val Trp Arg Ser Leu Phe Val Cys Phe Thr Thr Ile Val Ala
    370                 375                 380

Met Leu Leu Pro Phe Phe Asn Asp Ile Val Gly Ile Ile Gly Ala Leu
385                 390                 395                 400

Gln Phe Trp Pro Leu Thr Val Tyr Phe Pro Val Gln Met Tyr Ile Val
                405                 410                 415

Gln Lys Lys Val Pro Lys Trp Ser Val Lys Trp Ile Cys Val Gln Thr
            420                 425                 430

Met Ser Met Gly Cys Leu Leu Ile Ser Leu Ala Ala Val Val Gly Ser
        435                 440                 445

Val Asn Gly Val Met Leu Asp Leu Lys Val Tyr Lys Pro Phe Lys Thr
    450                 455                 460

Met Tyr
465
```

<210> SEQ ID NO 6
<211> LENGTH: 466
<212> TYPE: PRT
<213> ORGANISM: artificial
<220> FEATURE:
<223> OTHER INFORMATION: Bottle Gourd AAP2B protein
<220> FEATURE:
<221> NAME/KEY: Aa_trans
<222> LOCATION: (20)..(453)

<400> SEQUENCE: 6

```
Met Ala Val Leu Pro Ile Asn Asp Ser Ala Ser Phe Asp Asp Asp Gly
1               5                   10                  15

Arg Pro Lys Arg Thr Gly Thr Phe Trp Thr Ala Ser Ala His Ile Ile
            20                  25                  30

Thr Ala Val Ile Gly Ser Gly Val Leu Ser Leu Ala Trp Ala Ile Ala
        35                  40                  45

Gln Leu Gly Trp Val Ala Gly Pro Phe Val Met Leu Leu Phe Ala Phe
    50                  55                  60

Ile Gly Tyr Tyr Thr Ser Cys Leu Leu Ala Asp Cys Tyr Arg Ser Gly
65                  70                  75                  80

Asp Pro Val Ser Gly Lys Arg Asn Tyr Thr Tyr Met His Ala Val Arg
                85                  90                  95

Ser Leu Leu Gly Glu Ala His Met Val Ala Cys Gly Val Met Gln His
            100                 105                 110

Ile Asn Leu Ile Gly Ile Thr Ile Gly Tyr Thr Ile Ala Ser Ser Ile
        115                 120                 125

Ser Met Met Ala Ile Lys Arg Ser Asn Cys Phe His Ser Ser Gly Gly
    130                 135                 140

Lys Asn Pro Cys His Ile Ser Ser Asn Pro Phe Met Leu Ser Phe Gly
145                 150                 155                 160

Ile Val Glu Ile Ile Leu Ser Gln Ile Pro Asn Phe Asp Gln Ile Trp
                165                 170                 175

Trp Leu Ser Ile Val Ala Ala Ile Met Ser Phe Thr Tyr Ser Thr Ile
            180                 185                 190

Gly Leu Ser Leu Gly Ile Ala Lys Val Ala Glu Ser Gly Ser Phe Lys
        195                 200                 205

Gly Thr Leu Ser Gly Val Ser Val Gly Thr Ile Asn Glu Thr Glu Lys
    210                 215                 220

Ile Trp Arg Ser Phe Gln Ala Leu Gly Asp Ile Ala Phe Ala Tyr Ser
225                 230                 235                 240

Phe Ala Ile Val Leu Ile Glu Val Gln Asp Thr Ile Arg Cys Pro Pro
                245                 250                 255

Ser Glu Ala Lys Thr Met Lys Lys Ala Thr Gly Phe Ser Ile Thr Leu
            260                 265                 270

Thr Thr Ile Phe Tyr Met Leu Cys Gly Thr Met Gly Tyr Ala Ala Phe
        275                 280                 285

Gly Asn Thr Ala Pro Gly Asn Leu Leu Thr Gly Phe Gly Phe Tyr Asn
    290                 295                 300

Pro Phe Trp Leu Leu Asp Ile Ala Asn Val Ala Ile Val Val His Leu
305                 310                 315                 320

Val Gly Ala Tyr Gln Val Phe Ser Gln Pro Val Tyr Ala Phe Val Glu
                325                 330                 335

Lys Lys Ala Ala Gln Ala Trp Pro Asp Ser Ala Phe Ile Thr Lys Asp
            340                 345                 350
```

-continued

Tyr Lys Leu Ser Leu Phe Ser Ser Arg Ser Tyr Asn Ile Asn Phe Phe
        355                 360                 365

Arg Leu Val Trp Arg Ser Leu Phe Val Cys Phe Thr Thr Ile Val Ala
    370                 375                 380

Met Leu Leu Pro Phe Phe Asn Asp Ile Val Gly Ile Ile Gly Ala Leu
385                 390                 395                 400

Gln Phe Trp Pro Leu Thr Val Tyr Phe Pro Val Gln Met Tyr Ile Val
                405                 410                 415

Gln Lys Lys Val Pro Lys Trp Ser Val Lys Trp Ile Cys Val Gln Thr
            420                 425                 430

Met Ser Met Gly Cys Leu Leu Ile Ser Leu Ala Ala Val Val Gly Ser
        435                 440                 445

Ile Asn Gly Val Met Leu Asp Leu Lys Val Tyr Lys Pro Phe Lys Thr
    450                 455                 460

Met Tyr
465

<210> SEQ ID NO 7
<211> LENGTH: 1401
<212> TYPE: DNA
<213> ORGANISM: artificial
<220> FEATURE:
<223> OTHER INFORMATION: Melon AAP2A cDNA

<400> SEQUENCE: 7
atggccgtac ttcccgtcaa cgactccgct agcttggacg atgatggaca cccaaaacga 60
accggtacgt tttggacggc aagtgctcac ataatcacta cggttattgg ttcgggtgtg 120
ttatcgttgg catgggcgat tgctcagcta gggtggattg tgggtccctc cgtcatgttg 180
ttgttcgcct tcatcggtta ctacacctca tgtttgctcg ccgactgcta tcgctccggt 240
gatcctctta atggcaagag aaaccatact tacatgcatg cagttcgctc cctccttggt 300
gaagctcata tggtggcatg tggagtaatg cagaacataa acttgatcgg aataacaatt 360
ggatatacga ttgcgtcgtc aatcagtatg atggcaatta aaaggtcaaa ttgctttcat 420
agtagtggtg gaaaaaatcc atgtcatatt tcaagcaacc cattcatggt gtcttttgga 480
gttcttgaaa taattctgtc tcaaattcca aattttgatc agatttggtg gctctctacg 540
ctggctgcta tcatgtcttt tacatattct ttcattggcc tttcccttgg aatagccaaa 600
gtggcagaaa gtgggagatt taaaggaaca attagtggag taagtgtggg aacaataagt 660
aaaaccgaaa aaaaattgag aagttttcaa gcacttgggg atattgcttt tgcttattct 720
tttgcaattg tacttattga aattcaggac acaataaaat gtccaccatc agaagcgaag 780
acaatgaaga aagcaacaac tttcagcatt atattgacca ccttattcta cctactatgc 840
ggatgcatgg gttatgcagc atttggcaac aatgccccag gcaatctctt aactggcttt 900
ggcttctaca atccctttttg gctcatcgac atagccaatg tcgccatcgt tgttcacctt 960
gtgggcgcct accaagtcct tagccaaccc atcttcgcct ttgtggagaa gaaggctgcc 1020
caagcatggc ccgactcacc cttcatcaat aaagactaca agctctctat ctcctcttct 1080
cgcttataca acatcaacct ctttcgactt ttttggagaa cccttttcgt ctgcttcacc 1140
accaccattg ctatgttaat ccctttcttc aacgacatcg ttggaattat tggggctctc 1200
caattctggc ccttaactgt ctattttcct attcagatgt atattgtcca gaaaaagata 1260
cctcaatgga gtgtcaagtg gatttgtgtt caaactatga gcgtcggatg ccttttggtc 1320
tctcttgctg ctgctgttgg ctctataagt ggtgtcatgc ttgatcttaa ggtttataag 1380
cctttcaaga caatgtattg a 1401

<210> SEQ ID NO 8
<211> LENGTH: 1401
<212> TYPE: DNA
<213> ORGANISM: artificial
<220> FEATURE:
<223> OTHER INFORMATION: Melon AAP2B cDNA

<400> SEQUENCE: 8
atggccgtgc ttcccgtcaa tgactccgct agctttgatg atgatggtcg ccccaaacga 60
accggtacgt tttggacggc aagtgctcat ataataactg cggtcattgg ttcgggggtg 120
ttgtcattgg catgggcgat tgcgcaactc ggatggatcg ctggtccttc agtgatgttg 180
ctgttttctt tcatcggtta ctatacctct tgtttgctcg ccgactgtta tcggtccggc 240
gacccggtca gtggcaagag aaaccccact tacatgcatg cagttcgctc cctccttggt 300
gaaacacaca tggtggcatg tggaataatg cagtacataa acctgatcgg aataacaatc 360
ggatatacaa ttgcatcgtc aatcagcatg atggcaatta aacggtcaaa ttgctttcat 420
agcagtggag gaaaaaatcc atgtcatatt tcaagcaatc cgttcatgtt gtccttcgga 480
attgtggaaa taattttatc tcaaattcca aatttgatc agatttggtg gctctccatt 540
gttgctgcta tcatgtcttt tacctattct tccattggcc ttacccttgg catagccaaa 600
gtcgcagaaa gtggggtttt taaaggaaca cttagtggaa taactgtggg aacagtaact 660
caaagtgaaa agatatggag aagtttccaa gcacttggcg atattgcttt tgcttattct 720
tttgcaattg tccttattga agttcaggac acaattagat gtccaccttc agaagcaaag 780
acaatgaaaa aagcagcagg attcagcatt acattaacca ccatattcta catactatgt 840
ggatgcatgg gctatgcagc ctttggcaac actgcccccg gtaacctttt aactggcttt 900
ggcttctaca accccttttg gctcctcgac atcgccaatg tctccattgt tgttcacctc 960
gttggtgcct accaagtctt tagccaaccc gtctatgcct ttgtagagaa gaaggtcgtc 1020
caaacatggc cagacacccc cttcttcacc aaagagtaca agctctctct cttctcctct 1080
cgcttctaca acatcaacct ctttcgactg gtatggagaa ctcttttcgt ctgcttcacc 1140
accatcgtcg caatgttgct ccctttcttc aacgacatcg ttgggatcat cggggcactt 1200
caattttggc cgatgaccgt ctattttcca gtccagatgt atgttgttca aaagaaggta 1260
cctaaatgga gtgtgaagtg gatttgtgtg caaacaatga gcatgggatg ccttttgatc 1320
tctcttgctg cagctgtggg ctctattagt ggtgtcatgc ttgatctcaa ggtttataag 1380
cctttcaaga caatgtattg a 1401

<210> SEQ ID NO 9
<211> LENGTH: 1401
<212> TYPE: DNA
<213> ORGANISM: artificial
<220> FEATURE:
<223> OTHER INFORMATION: Watermelon AAP2A cDNA

<400> SEQUENCE: 9
atggccgtgc ttcccttcag cgattccgct atcttcgacg atgatggacg cccaaaacga 60
accggtacgt tttggacggc aagtgctcac ataatcacta ccgtgattgg ttcgggtgtg 120
ttatcgttag cgtgggcgat cgctcagctc gggtggatcg caggtccctc cgtgatgttg 180
ttgttcgcct tcatcggtta ctacacctcc tgtttgctcg ccgactgcta tcgctccggc 240

```
gacccagtta atggcaagag gaaccacact tacatgcatg cagttcgctc cctccttggt    300
gaagctcata tggtggcatg tggagtaatg caatacataa acttgatcgg aataacaatc    360
ggatatacga ttgcatcctc aattagcatg atggcgatta aacggtcaaa ttgctttcat    420
agtagtgggg gaaaaaatcc atgtcatatt tcaagcaatc cattcatgtt gtgttttgga    480
attgttgaaa taattctttc tcaaattcca aattttgatc agatttggtg gctctccaca    540
gtggctgcta ttatgtcttt tacttattct actattggcc ttagccttgg aatagccaaa    600
gttgcagaaa gtgggagttt taaaggaaca cttagtggag taagtgtggg atcaataact    660
cgaaccgaaa agaaatggag aagtttccaa gcacttggag atattgcttt tgcttattct    720
tttgcaattg tccttattga aattcaggac acaataagat gtccaccatc agaagcgaag    780
acaatgaaga aagcaacagg gttcagcatt atattgacca ccttatttta cttactatgc    840
ggatgcatgg gctatgcagc ctttggcaac aatgccccag gcaacctctt aactggcttt    900
ggcttctaca atcccttctg gctcctcgac atcgccaatg ttgccatcgt cgtccacctc    960
gtgggtgcct accaagtcct tagccagcct gtctttgcct ttgttgagaa gaaggctgcc   1020
ctagcatggc ccgactcacc cttcatcacc aaggactaca agctctccat ctcctcttcc   1080
cgttcctaca acatcaacct ctttcgactc gtttggagat ccctttttcgt ttgcttcacc  1140
accattattg ccatgttgat ccctttcttc aacgacatcg ttgggattat cggggccctc   1200
caattttggc ccttgactgt ctattttcct gttcagatgt atatggttca gaagaaggta   1260
cctaaatgga gtgtcaagtg gatttatgtt caaactataa gcatgggatg ccttttggtc   1320
tctcttgctg ctgctgtggg ctctattaat ggtgtcatgc ttgatcttaa ggtttataag   1380
cctttcaaga caatgtattg a                                             1401
```

<210> SEQ ID NO 10
<211> LENGTH: 1401
<212> TYPE: DNA
<213> ORGANISM: artificial
<220> FEATURE:
<223> OTHER INFORMATION: Watermelon AAP2B cDNA

<400> SEQUENCE: 10

```
atggctgtgc ttcccatcaa cgactctgcg agctttgacg atgatggtcg ccccaaacga     60
accggtacgt tttggacggc aagtgctcac ataatcacgg cggtgatcgg ttcaggtgtg    120
ttatcgttag cgtgggcaat tgctcagctc ggatggatcg cgggtccctt tgtgatgttg    180
ttgttcgcct tcatcggtta ctacacctcc tgtttgctcg ccgactgcta tcgctccggc    240
gacccagtta atggcaagag aaaccacact tacatgcatg cagttcgctc cctccttggt    300
gaagctcata tggtggcatg tggagtaatg caatacataa acttgatcgg aataacaatc    360
ggatatacga ttgcatcctc aattagcatg atggcgatta aacggtcaaa ttgctttcat    420
agtagtgggg gaaaaaatcc atgtcatatt tcaagcaatc cattcatgtt gtgttttgga    480
attgttgaaa taattctttc tcaaattcca aattttgatc agatttggtg gctctccaca    540
gtggctgcta ttatgtcttt tacttattct actattggcc ttagccttgg aatagccaaa    600
gttgcagaaa gtgggagttt taaaggaaca cttagtgtaa taagtgtggg aacaattact    660
caaactgaaa agatatggag aagtttccaa gcacttggag atattgcttt tgcttattct    720
tttgcaattg tccttattga agttcaggac acaataacat gcccaccctc agaagcaaag    780
acaatgaaga aagcaacagg attcagcatt gcattgacca ccgtattcta cttgctatgt    840
ggatccatgg gctatgcagc ctttggcaac actgccccag gtaacctctt aactggtttt    900
```

```
ggcttctaca accccttttg gctccttgac attgccaaca ttgccattgt catccacctc    960

gttggtgcct accaagtctt cagtcaaccc gtctttgcct tcgtcgagaa gaaggctacc   1020

caagcatggc ccgactcggc ggttatcacc aaagaccaca agctctccct cttctcctcc   1080

cactcctaca acatcaacct ctttcgactc gtttggagat cccttttcgt ttgcttcacc   1140

accatcgttg ccatgttgct ccctttcttc aacgacatcg tcgggattat cggggccctc   1200

caattttggc cgttgaccgt ttattttcct gtccagatgt atattgttca aaagaaggta   1260

cctaaatgga gtgtcaagtg gatttgtgtt caaactatga gcatgggatg ccttttgatc   1320

tctcttgctg cggttgtggg ctctgttaat ggtgtcatgc ttgaccttaa ggtgtataag   1380

cctttcaaga caatgtattg a                                             1401
```

<210> SEQ ID NO 11
<211> LENGTH: 1401
<212> TYPE: DNA
<213> ORGANISM: artificial
<220> FEATURE:
<223> OTHER INFORMATION: Bottle Gourd AAP2A cDNA

<400> SEQUENCE: 11

```
atggccgtgc ttcccatcaa cgactctgct agcttcgacg atgatggacg cccaaaacga     60

accggtacgt tttggacggc aagtgctcac ataatcacta cggtgattgg ttctggtgtg    120

ttatcgttag catgggcgat cgctcagctc gggtggatcg ccggtccctc cgtgatgttg    180

ttgttcgcct tcatcggtta ctacacctcc tgttttctcg ctgactgcta tcgctccggc    240

gatccggtta atgggaagag aaaccacact tacatgcatg cagttcgctc cctccttggg    300

gaagctcata tggtggcatg tggagtaatg cagaacataa acttgatcgg aataacaatc    360

ggatacacga ttgcgtcgtc aattagcatg atggcgatta aacggtcaaa ttgctttcat    420

agaagtgggg gaaaaaatcc atgtcatatt tcaagcaatc cattcatgtt gtcttttgga    480

attgtggaaa taattctgtc tcaaattcca aattttgatc agatttggtg gctctccata    540

gttgctgcta tcatgtcttt tacttattct accattggcc tttcccttgg aatagccaaa    600

gttgcagaga gtgggagtgt taaaggaaca cttagtggaa taagtgtggg atcaataact    660

ccaaccgaaa agaaatggag aagtttccaa gcacttggcg atattgcttt tgcttattct    720

tttgcaattg tccttattga aattcaggat acaataagat gtccaccatc agaagcgaag    780

acaatgaaga aagcgacagg gttcagcatt atattgacca ccttattcta cttactatgc    840

ggatgcacgg gctatgcagc ctttggcaac aatgccccag gcaacctctt aactggcttt    900

ggcttctaca atccctttttg gctcctcgac atcgccaatg ttgccatcgt cttccacctc    960

gtgggcgcct accaagtcct tagtcaaccc gtctttgcct ttgttgagaa gaaggctgcc   1020

caagcatggc ctgactcggc cttcatcacc aaagactaca agctctccct ctcctcttcc   1080

cgctcctaca acatcaacct ctttcgactc atatggagat cccttttcgt ctgcttcacc   1140

accatcgttg ccatgttgat ccctttcttc aacgacatcg tcgggattat cggggccctc   1200

caattctggc ccctgactgt ctattttcct gttcagatgt atattgttca gaagaagata   1260

cctaaatgga gtgtcaagtg gatttatgtt caaattatga gcatgggatg ccttttggtc   1320

tctcttgctg ctgctgtggg ctctattaat ggtgtcatgc ttgatcttaa ggtttataag   1380

cctttcaaga caatgtattg a                                             1401
```

<210> SEQ ID NO 12

<211> LENGTH: 1401
<212> TYPE: DNA
<213> ORGANISM: artificial
<220> FEATURE:
<223> OTHER INFORMATION: Bottle Gourd AAP2B cDNA

<400> SEQUENCE: 12

```
atggccgtgc ttcccatcaa cgactccgca agcttcgacg atgatggccg ccccaaacga      60
actggtacgt tttggacggc aagtgctcat ataatcaccg ccgtgattgg ttcgggtgtg     120
ttatcgttgg catgggcgat tgctcagctc ggatgggttg ccggtccttt cgtgatgttg     180
ttgttcgctt tcatcggtta ctacacctcc tgtttgctcg ccgactgcta tcgctccggc     240
gatccggtta gtggcaagag aaactacact tacatgcatg cagttcggtc cctccttggt     300
gaagctcata tggtggcatg tggagtaatg cagcacataa acttgattgg aataacaatc     360
ggatatacaa ttgcgtcgtc aatcagcatg atggcgatta aacggtcaaa ttgctttcac     420
agcagtggag gaaaaaatcc atgtcatatt tcaagcaatc cattcatgtt gtcttttgga     480
attgtggaaa taattctgtc tcaaattcca aattttgatc agatttggtg gctctccata     540
gttgctgcta tcatgtcttt tacttattct accattggcc tttctcttgg aatagccaaa     600
gttgcagaaa gtgggagttt taaaggaaca cttagtggag taagtgtggg aacaattaat     660
gaaactgaaa agatatggag aagtttccaa gcacttggag atattgcttt tgcttattct     720
tttgcaattg tccttattga agttcaggac acgatcagat gcccaccatc agaagcaaag     780
acaatgaaga aagcaacagg attcagcatt acattgacca ccatattcta catgctatgt     840
ggaaccatgg gctatgcagc ctttggcaac actgccccag gcaacctctt gactggcttt     900
ggcttctaca accccttttg gctcctcgac atcgccaacg tcgccattgt cgttcacctc     960
gtcggtgcct accaagtctt cagccaaccc gtctatgcct tcgtcgagaa gaaggctgcc    1020
caagcatggc ccgactcagc gttcatcacc aaagactaca agctctccct cttctcctct    1080
cgctcctaca acatcaactt ctttcgcctc gtttggagat cccttttcgt ttgcttcacc    1140
accatcgttg ccatgttgct ccctttcttc aacgacattg tcggaattat cggggccctc    1200
caattttggc cgttgaccgt ctattttcct gtccaaatgt acattgttca gaagaaggta    1260
cctaaatgga gtgtcaagtg gatttgtgtt caaactatga gcatgggatg ccttttgatc    1320
tctcttgctg ctgttgtggg ctcaattaat ggtgtcatgc ttgatcttaa ggtatataag    1380
cctttcaaga caatgtactg a                                              1401
```

<210> SEQ ID NO 13
<211> LENGTH: 465
<212> TYPE: PRT
<213> ORGANISM: artificial
<220> FEATURE:
<223> OTHER INFORMATION: Bitter Gourd AAP protein

<400> SEQUENCE: 13

```
Met Ala Met Leu Pro Ile Asn Asp Ser Ala Ile Leu Asp Asp Asp Gly
1               5                   10                  15

Arg Leu Lys Arg Thr Gly Thr Phe Trp Thr Ala Ser Ala His Ile Ile
            20                  25                  30

Thr Ala Val Ile Gly Ser Gly Val Leu Ser Leu Ala Trp Ala Ile Ala
        35                  40                  45

Gln Leu Gly Trp Val Ala Gly Pro Ala Val Met Leu Leu Phe Ala Phe
    50                  55                  60

Ile Gly Tyr Tyr Thr Ser Cys Leu Leu Ala Asp Cys Tyr Arg Ser Gly
```

```
65                  70                  75                  80

Asp Pro Ile Asn Gly Lys Arg Asn Tyr Thr Tyr Met His Ala Val Arg
                85                  90                  95

Ser Leu Leu Gly Gly Ala Gln Thr Thr Ala Cys Gly Ile Met Gln Tyr
            100                 105                 110

Met Asn Leu Ile Gly Ile Ala Ile Gly Tyr Thr Ile Ala Ser Ser Ile
        115                 120                 125

Ser Met Met Ala Ile Lys Arg Ser Asn Cys Phe His Ser Ser Gly Gly
    130                 135                 140

Lys Asn Pro Cys His Met Ser Ser Asn Pro Phe Met Ile Ser Phe Gly
145                 150                 155                 160

Val Met Glu Ile Phe Leu Ser Gln Ile Pro Asp Phe Asp Gln Ile Trp
                165                 170                 175

Trp Leu Ser Thr Val Ala Ala Ile Met Ser Phe Thr Tyr Ser Thr Ile
            180                 185                 190

Gly Leu Gly Leu Gly Ile Ala Lys Val Ala Glu Ser Gly Ser Phe Lys
        195                 200                 205

Gly Thr Leu Ser Gly Ile Gly Val Gly Thr Val Thr Gln Ser Gln Lys
    210                 215                 220

Ile Trp Arg Thr Phe Gln Ala Leu Gly Asp Ile Ala Phe Ala Tyr Ser
225                 230                 235                 240

Phe Ser Ile Ile Leu Ile Glu Ile Gln Asp Thr Ile Arg Cys Pro Pro
                245                 250                 255

Ser Glu Ala Lys Thr Met Lys Lys Ala Thr Gly Leu Ser Ile Ala Val
            260                 265                 270

Thr Thr Thr Phe Tyr Leu Leu Cys Gly Cys Met Gly Tyr Ala Ala Phe
        275                 280                 285

Gly Asn Ser Ala Pro Gly Asn Leu Leu Thr Gly Phe Gly Phe Tyr Asn
    290                 295                 300

Pro Phe Trp Leu Leu Asp Ile Ala Asn Val Ala Ile Val Val His Leu
305                 310                 315                 320

Val Gly Ala Tyr Gln Val Phe Cys Gln Pro Val Phe Ala Phe Val Glu
                325                 330                 335

Lys Lys Ala Ala Gln Ala Trp Pro Asp Ser Thr Phe Ile Thr Lys Glu
            340                 345                 350

His Lys Leu Ser Leu Phe Arg Arg Ser Tyr Asn Val Asn Met Phe Arg
        355                 360                 365

Leu Val Trp Arg Ser Leu Phe Val Cys Phe Thr Thr Val Val Ala Met
    370                 375                 380

Leu Leu Pro Phe Phe Asn Asp Val Val Gly Ile Ile Gly Ala Leu Gln
385                 390                 395                 400

Phe Trp Pro Leu Thr Val Tyr Phe Pro Val Gln Met Tyr Ile Val Gln
                405                 410                 415

Lys Lys Ile Pro Lys Trp Ser Val Lys Trp Val Cys Val Gln Thr Met
            420                 425                 430

Ser Met Gly Cys Leu Leu Ile Ser Val Ala Ala Ala Val Gly Ser Val
        435                 440                 445

Ile Gly Val Met Leu Asp Leu Lys Val Tyr Lys Pro Phe Lys Thr Arg
    450                 455                 460

Tyr
465
```

<210> SEQ ID NO 14

<211> LENGTH: 466
<212> TYPE: PRT
<213> ORGANISM: artificial
<220> FEATURE:
<223> OTHER INFORMATION: C. pepo AAP2A protein

<400> SEQUENCE: 14

```
Met Ala Val Leu Pro Ile Asn Asp Ala Ala Ser Phe Asp Asp Asp Gly
1               5                   10                  15

Arg Pro Lys Arg Thr Gly Thr Phe Trp Thr Ala Ser Ala His Ile Ile
            20                  25                  30

Thr Ala Val Ile Gly Ser Gly Val Leu Ser Leu Ala Trp Ala Ile Ala
        35                  40                  45

Gln Leu Gly Trp Val Ala Gly Pro Ser Val Met Leu Leu Phe Ala Phe
    50                  55                  60

Ile Gly Tyr Tyr Thr Ser Cys Leu Leu Ala Asp Cys Tyr Arg Ser Ser
65                  70                  75                  80

Asp Pro Val Asn Gly Lys Arg Asn Tyr Thr Tyr Met His Ala Val Arg
                85                  90                  95

Ser Leu Leu Gly Arg Ser Gln Thr Thr Ala Cys Gly Val Leu Gln Tyr
            100                 105                 110

Val Asn Leu Ile Gly Ile Ser Ile Gly Tyr Thr Ile Ala Ser Ala Ile
        115                 120                 125

Ser Met Met Ala Val Lys Arg Ser Asn Cys Phe His Ser Ser Gly Gly
    130                 135                 140

Lys Asn Pro Cys His Met Ser Ser Asn Pro Phe Met Val Ser Phe Gly
145                 150                 155                 160

Val Met Glu Ile Ile Leu Ser Gln Ile Pro Asp Phe Asp Gln Ile Trp
                165                 170                 175

Trp Leu Ser Ser Val Ala Ala Val Met Ser Phe Thr Tyr Ser Thr Ile
            180                 185                 190

Gly Leu Gly Leu Gly Ile Ala Lys Val Ala Glu Thr Gly Ser Phe Lys
        195                 200                 205

Gly Thr Val Ser Gly Ile Ser Val Gly Thr Ile Asn Gln Ser Gln Lys
    210                 215                 220

Ile Trp Arg Thr Phe Gln Ala Leu Gly Asp Ile Ala Phe Ala Tyr Ser
225                 230                 235                 240

Phe Ser Ile Ile Leu Ile Glu Ile Gln Asp Thr Ile Arg Cys Pro Pro
                245                 250                 255

Ser Glu Ala Lys Thr Met Lys Lys Ala Thr Gly Phe Ser Ile Ala Leu
            260                 265                 270

Thr Thr Ile Phe Tyr Met Leu Cys Gly Cys Met Gly Tyr Ala Ala Phe
        275                 280                 285

Gly Asn Asp Ala Pro Gly Asn Leu Leu Thr Gly Phe Gly Phe Tyr Asn
    290                 295                 300

Pro Phe Trp Leu Leu Asp Ile Ala Asn Ile Ala Ile Val Val His Leu
305                 310                 315                 320

Val Gly Ala Tyr Gln Val Phe Ser Gln Pro Val Phe Ala Phe Val Glu
                325                 330                 335

Lys Lys Ala Ala Gln Ala Trp Pro Asp Ser Pro Phe Ile Thr Lys His
            340                 345                 350

His Lys Leu Ser Ile Ser Ser Ser Arg Ser Tyr Asn Val Asn Leu Phe
        355                 360                 365

Arg Leu Val Trp Arg Ser Leu Phe Val Cys Phe Thr Thr Val Val Ala
    370                 375                 380
```

```
Met Leu Leu Pro Phe Phe Asn Asp Val Val Gly Ile Ile Gly Ala Leu
385                 390                 395                 400

Gln Phe Trp Pro Leu Thr Val Tyr Phe Pro Val Gln Met Tyr Ile Val
                405                 410                 415

Gln Lys Lys Ile Pro Lys Trp Ser Leu Lys Trp Val Cys Val Gln Thr
            420                 425                 430

Met Ser Met Gly Cys Leu Leu Ile Ser Phe Ala Ala Val Val Gly Ser
        435                 440                 445

Val Ile Gly Val Met Leu Asp Leu Lys Val Tyr Lys Pro Phe Lys Thr
    450                 455                 460

Thr Tyr
465


<210> SEQ ID NO 15
<211> LENGTH: 458
<212> TYPE: PRT
<213> ORGANISM: artificial
<220> FEATURE:
<223> OTHER INFORMATION: C. pepo AAP2B protein

<400> SEQUENCE: 15

Met Ala Val Leu Pro Ile Asn Asp Ser Ser Ser Ser Asp Asp Asp Gly
1               5                   10                  15

Arg Pro Lys Arg Thr Gly Thr Phe Trp Thr Ala Ser Ala His Ile Ile
            20                  25                  30

Thr Ala Val Ile Gly Ser Gly Val Leu Ser Leu Ala Trp Ala Ile Ala
        35                  40                  45

Gln Leu Gly Trp Ile Ala Gly Pro Ile Val Met Leu Leu Phe Ala Phe
    50                  55                  60

Ile Ser Tyr Tyr Thr Ser Cys Leu Leu Thr Asp Cys Tyr Arg Ser Asn
65                  70                  75                  80

Asp Ser Val Asn Ala Lys Arg Asn Tyr Thr Tyr Met His Ala Val Arg
                85                  90                  95

Ser Phe Leu Gly Arg Gly Gln Thr Val Val Cys Gly Val Ile Gln Tyr
            100                 105                 110

Met Asp Leu Ile Gly Val Ala Ile Gly Tyr Thr Ile Ala Ser Ser Ile
        115                 120                 125

Ser Met Met Ala Val Lys Arg Ser Asn Cys Phe His Lys Ser Gly Gly
    130                 135                 140

Lys Ser Pro Cys Arg Met Ser Ser Asn Pro Phe Met Val Ser Phe Gly
145                 150                 155                 160

Val Val Glu Ile Ile Leu Ser Gln Ile Pro Lys Phe Asp Gln Ile Trp
                165                 170                 175

Trp Leu Ser Thr Val Ala Ala Ile Met Ser Phe Thr Tyr Ser Thr Ile
            180                 185                 190

Gly Leu Ala Leu Gly Ile Ala Lys Val Ala Glu Asn Gly Ser Phe Lys
        195                 200                 205

Gly Thr Val Thr Glu Thr Gln Lys Ile Trp Arg Thr Phe Gln Ala Leu
    210                 215                 220

Gly Asp Ile Ala Phe Ala Tyr Ser Phe Ser Val Ile Leu Ile Glu Ile
225                 230                 235                 240

Gln Asp Thr Ile Arg Cys Pro Pro Ser Glu Ala Lys Thr Met Lys Lys
                245                 250                 255

Ala Ser Gly Phe Ser Ile Ala Val Thr Thr Ile Phe Tyr Leu Leu Cys
            260                 265                 270
```

```
Gly Cys Met Gly Tyr Ala Ala Phe Gly Asn Asn Ala Pro Gly Asn Leu
        275                 280                 285

Leu Thr Gly Phe Gly Phe Tyr Asn Pro Tyr Trp Leu Leu Asp Ile Ala
    290                 295                 300

Asn Val Ala Ile Val Val His Leu Val Gly Ala Tyr Gln Val Phe Cys
305                 310                 315                 320

Gln Pro Val Phe Ala Phe Val Glu Lys Thr Ala Ala Gln Thr Trp Pro
                325                 330                 335

Asp Ser Ala Phe Ile Thr Lys His Tyr Arg Leu Ser Leu Ser Ser Ser
            340                 345                 350

Arg Ser Tyr Asn Ile Asn Phe Phe Arg Leu Val Trp Arg Thr Leu Phe
        355                 360                 365

Val Cys Phe Thr Thr Val Val Ala Met Leu Leu Pro Phe Phe Asn Asp
    370                 375                 380

Ile Val Gly Ile Met Gly Ala Phe Gln Phe Trp Pro Leu Ser Val Tyr
385                 390                 395                 400

Phe Pro Val Gln Met Tyr Ile Val Gln Lys Lys Ile Ala Lys Trp Ser
                405                 410                 415

Val Lys Trp Val Cys Val Gln Thr Met Ser Met Gly Cys Leu Leu Ile
            420                 425                 430

Ser Ile Ala Ala Gly Val Gly Ser Leu Ile Gly Val Val Leu Asp Leu
        435                 440                 445

Lys Val Tyr Lys Pro Phe Ile Thr Arg Tyr
    450                 455
```

<210> SEQ ID NO 16
<211> LENGTH: 1398
<212> TYPE: DNA
<213> ORGANISM: artificial
<220> FEATURE:
<223> OTHER INFORMATION: Bitter Gourd AAP cDNA

<400> SEQUENCE: 16

```
atggccatgc ttccgatcaa cgactctgcc attctcgacg acgatggccg cctcaaacgg     60

accggtactt tttggactgc gagtgcccat ataatcaccg cggtgatcgg ttcaggcgtg    120

ctatcgttag catgggcgat cgcgcagctc ggatgggttg ccggtccggc ggttatgctg    180

ctctttgcct tcattggcta ctacacctct tgtttgctcg ccgactgcta ccgctccggc    240

gatccaatca acggcaagag aaactacacc tacatgcacg cggtccgctc cctcctcggc    300

ggagctcaga cgacggcgtg cggtataatg cagtacatga acttgatcgg gatcgcgatc    360

gggtacacga tcgcgtcgtc aatcagcatg atggcgatca aacggtcgaa ttgtttccac    420

agcagcgggg ggaagaatcc atgtcatatg tcaagcaatc cgttcatgat ttcttttgga    480

gtaatggaaa tatttctgtc tcagattcct gattttgatc agatttggtg gctctctacg    540

gtggctgcta tcatgtcttt tacttattcc accattggcc ttggccttgg aatcgccaaa    600

gttgcagaaa gtgggagttt taaaggaaca ttgagtggca taggtgtggg aacagtgact    660

cagagccaaa agatatggag aactttccaa gcacttggcg atatcgcttt tgcctattct    720

ttttcaatca tccttattga aattcaggac accatccgat gcccaccatc agaagcaaag    780

acaatgaaga aagccacagg tctcagcata gccgtgacca caactttcta cttactgtgc    840

ggctgcatgg gctacgccgc attcggcaac agcgcgccgg gaaacctcct caccgggttc    900

gggttctaca accccttctg gctccttgac atcgccaacg ttgcgatcgt cgtccacctc    960
```

gtcggtgcct accaagtctt ctgccagccc gtcttcgcct ttgtcgagaa gaaggctgcc 1020
caggcatggc cagactcgac cttcatcaca aaggagcaca agctgtccct cttccgccgc 1080
tcatacaacg tcaacatgtt ccgactcgta tggagatccc tctttgtctg cttcaccacc 1140
gtcgtggcga tgctgcttcc tttcttcaac gacgtcgtcg ggatcatcgg ggcgctgcag 1200
ttctggccct tgacagtgta ttttccagtg cagatgtata ttgttcagaa gaagatacca 1260
aagtggagtg tgaagtgggt ttgtgtgcaa accatgagca tgggctgcct tttgatttcc 1320
gttgctgcgg ctgtgggatc tgttattggt gtcatgctcg atctcaaggt ttataagcct 1380
tttaagacac gttattga 1398

<210> SEQ ID NO 17
<211> LENGTH: 1401
<212> TYPE: DNA
<213> ORGANISM: artificial
<220> FEATURE:
<223> OTHER INFORMATION: C. pepo AAP2A cDNA

<400> SEQUENCE: 17
atggccgtgc ttcccatcaa cgatgccgct agcttcgacg acgatggccg ccccaaaaga 60
accggtacgt tttggacagc aagcgctcac ataatcacag ccgtcatcgg ttcaggtgtg 120
ttatcattag catgggcaat cgctcaactc ggatgggtcg ctggtccctc cgtgatgttg 180
ctatttgcct tcatcggcta ctacacttct tgtttgctcg ccgattgcta tcgctccagt 240
gacccagtga atggaaagag aaactacact tacatgcatg cagttcgctc ccttctcggt 300
agaagtcaga caacagcatg tggagtactt caatacgtga acctaatcgg aatatcgatt 360
ggatatacga ttgcgtcggc gatcagcatg atggcggtta aacggtcaaa ttgctttcat 420
agtagtggag ggaagaatcc atgtcatatg tcaagcaatc cattcatggt gtcttttgga 480
gtaatggaaa taattttgtc tcaaattcct gattttgatc agatttggtg gctctcttca 540
gtggctgctg tcatgtcttt tacctattcc accattggcc ttggccttgg aatagccaaa 600
gttgcagaaa cggggagttt taaagggacg gtgagtggaa taagtgtggg aacaataaat 660
caaagccaaa agatatggag aactttccaa gcacttggcg acatcgcttt tgcctattct 720
ttttcaatta tccttattga aattcaggac acaatcagat gcccaccctc ggaagcaaag 780
acaatgaaga aagcgacagg attcagcatt gcattgacca caatattcta catgctatgc 840
ggttgcatgg gctacgcagc ctttggcaac gacgccccag gcaacctctt gactggcttt 900
ggcttctaca acccattctg gctcctcgac atcgccaaca tcgccatcgt cgtccacctc 960
gttggcgcat accaagtctt ctctcagcct gtctttgctt tcgtcgagaa gaaagccgcc 1020
caagcatggc ccgactcccc cttcatcacc aaacaccaca agctctccat ctcttcctcc 1080
cgctcctaca atgtcaacct ctttcgactc gtttggagat ctcttttcgt ctgcttcacc 1140
accgtcgtcg ctatgttgct ccccttcttc aacgacgtgg tcgggatcat tggggctctc 1200
caattctggc cattgaccgt gtattttcct gtccagatgt atattgttca gaagaagata 1260
cctaaatgga gtctcaagtg ggtttgtgtt caaaccatga gcatgggctg ccttttgatc 1320
tcctttgctg ctgttgtggg ctctgttatt ggtgtcatgc ttgatcttaa ggtttataag 1380
cctttcaaga caacgtattg a 1401

<210> SEQ ID NO 18
<211> LENGTH: 1377
<212> TYPE: DNA
<213> ORGANISM: artificial -continued
<220> FEATURE:
<223> OTHER INFORMATION: C. pepo AAP2B cDNA

<400> SEQUENCE: 18
atggccgtgc tcccgatcaa tgactcctcg agctccgatg atgatggtcg ccccaagcgg 60
actggtacgt tttggacagc aagtgctcat ataatcacag ccgtaattgg ttcgggtgtg 120
ttatcgttag catgggcgat cgctcagctc ggatggattg ccggtcccat cgtgatgctc 180
ctatttgcct tcataagtta ctatacctct tgtttgctca ctgattgcta tcgctccaac 240
gactcagtta acgccaagag aaactatact tacatgcatg cagtccgctc cttcctaggc 300
agaggtcaaa cagtagtatg tggagtaata caatacatgg acttgattgg agtcgcaatc 360
ggatatacaa tcgcgtcatc gatcagcatg atggcggtta aacggtcaaa ttgcttccac 420
aaaagtgggg gaaagagtcc atgtcgtatg tcaagcaatc catttatggt atcatttgga 480
gttgtggaga taattttgtc tcaaattcca aaatttgacc aaatttggtg gctctccaca 540
gtggctgcta tcatgtcgtt tacatattca accattggcc ttgctcttgg gattgccaaa 600
gttgcagaaa atgggagttt taaaggaaca gtgactgaaa cccaaaagat ttggagaact 660
tttcaagcac ttggagatat tgcttttgcc tattcttttt cagttatcct tattgaaatt 720
caggacacaa tcagatgccc accatcagaa gcaaagacaa tgaagaaggc ctcaggattc 780
agcattgcag tgaccacaat cttctaccta ctttgtggat gcatgggcta tgcagccttt 840
ggcaacaacg ccccaggcaa cctcttgaca ggctttggct tctacaaccc gtattggctc 900
ctcgacatcg ccaacgtcgc catcgtcgtc catctcgtcg gcgcctacca agtcttctgt 960
cagcccgtct ttgccttcgt cgagaagacg gcagctcaaa catggcccga ttccgccttc 1020
atcaccaaac attacaggct ctccctctct tcctctcgct cgtacaatat caacttcttt 1080
cgacttgtat ggcgaaccct tttcgtgtgc ttcaccaccg tcgtcgccat gttgctcccg 1140
ttctttaacg acatcgtcgg gattatgggg gccttccaat tctggccgtt gtcggtctac 1200
tttccggttc agatgtatat tgttcagaag aagatagcta aatggagtgt gaagtgggta 1260
tgtgttcaaa ctatgagcat gggatgcctt ttgatatcca ttgctgctgg tgtgggctct 1320
cttattggtg ttgtgcttga tcttaaggtt tataagcctt tcatcacaag atattga 1377

<210> SEQ ID NO 19
<211> LENGTH: 466
<212> TYPE: PRT
<213> ORGANISM: Cucumis sativus

<400> SEQUENCE: 19

Met Ala Val Leu Pro Leu Asn Asp Ser Ser Ser Phe Asp Asp Asp Gly
1 5 10 15

His Pro Lys Arg Thr Gly Thr Leu Trp Thr Ala Ser Ala His Ile Ile
20 25 30

Thr Thr Val Ile Gly Ser Gly Val Leu Ser Leu Ala Trp Ala Ile Ala
35 40 45

Gln Leu Gly Trp Ile Val Gly Pro Ser Val Met Leu Leu Phe Ala Phe
50 55 60

Ile Gly His Tyr Thr Ser Cys Leu Leu Ala Asp Cys Tyr Arg Ser Gly
65 70 75 80

Asp Pro Leu Thr Gly Lys Arg Asn Pro Thr Tyr Met His Ala Val Arg
85 90 95

Ser Leu Leu Gly Glu Ala His Met Val Ala Cys Gly Val Met Gln Asn
100 105 110

-continued

```
Ile Asn Leu Met Gly Ile Thr Ile Gly Tyr Gln Ile Ala Ser Ser Ile
        115                 120                 125

Ser Met Met Ala Ile Lys Arg Ser Asn Cys Phe His Ser Ser Gly Gly
    130                 135                 140

Lys Asn Pro Cys His Ile Ser Ser Asn Pro Phe Met Met Ser Phe Gly
145                 150                 155                 160

Val Val Glu Ile Ile Leu Ser Gln Ile Pro Asn Phe Asp Gln Ile Trp
                165                 170                 175

Trp Leu Ser Thr Leu Ala Ala Ile Met Ser Phe Thr Tyr Ser Phe Ile
            180                 185                 190

Gly Leu Ser Leu Gly Ile Ala Lys Val Ala Glu Ser Gly Arg Phe Lys
        195                 200                 205

Gly Thr Ile Ser Gly Val Ser Val Gly Ser Ile Ser Lys Thr Glu Lys
    210                 215                 220

Lys Leu Arg Ser Phe Gln Ala Leu Gly Asp Ile Ala Phe Ala Tyr Ser
225                 230                 235                 240

Phe Ala Ile Val Leu Ile Glu Ile Gln Asp Thr Ile Lys Cys Pro Pro
                245                 250                 255

Ser Glu Ala Lys Thr Met Lys Lys Ala Thr Arg Phe Ser Ile Ile Leu
            260                 265                 270

Thr Thr Leu Phe Tyr Ile Leu Cys Gly Cys Ser Gly Tyr Ala Ala Phe
        275                 280                 285

Gly Asn Asn Ala Pro Gly Asn Leu Leu Thr Gly Phe Gly Phe Tyr Asn
    290                 295                 300

Pro Phe Trp Leu Ile Asp Ile Ala Asn Val Ala Ile Val Val His Leu
305                 310                 315                 320

Val Gly Ala Tyr Gln Val Leu Ser Gln Pro Ile Phe Ala Phe Val Glu
                325                 330                 335

Lys Lys Ala Ala Gln Ala Trp Pro Glu Ser Pro Phe Ile Thr Lys Glu
            340                 345                 350

Tyr Lys Leu Ser Ile Ser Ser Ser His Ser Tyr Asn Ile Asn Leu Phe
        355                 360                 365

Arg Leu Ile Trp Arg Ser Leu Phe Val Cys Phe Thr Thr Thr Ile Ala
    370                 375                 380

Met Leu Ile Pro Phe Phe Asn Asp Ile Val Gly Ile Ile Gly Ala Leu
385                 390                 395                 400

Gln Phe Trp Pro Leu Thr Val Tyr Phe Pro Ile Gln Met Tyr Ile Val
                405                 410                 415

Gln Lys Lys Ile Arg Gln Trp Ser Val Lys Trp Ile Cys Val Gln Thr
            420                 425                 430

Met Ser Met Gly Cys Leu Leu Val Ser Leu Ala Ala Ala Val Gly Ser
        435                 440                 445

Ile Ser Gly Val Met Leu Asp Leu Lys Val Tyr Lys Pro Phe Lys Thr
    450                 455                 460

Met Tyr
465
```